(12) United States Patent
Gupta et al.

(10) Patent No.: US 12,011,275 B2
(45) Date of Patent: *Jun. 18, 2024

(54) METHOD AND APPARATUS FOR WIDE-BAND PHASE GRADIENT SIGNAL ACQUISITION

(71) Applicant: Analytics For Life Inc., Toronto (CA)

(72) Inventors: Sunny Gupta, Belleville (CA); Don Crawford, Fernandina Beach, FL (US); Timothy William Fawcett Burton, Toronto (CA); Shyamlal Ramchandani, Kingston (CA); Kristine Canavan, Wayland, MA (US)

(73) Assignee: Analytics For Life, Inc., Toronto (CA)

( * ) Notice: Subject to any disclaimer, the term of this patent is extended or adjusted under 35 U.S.C. 154(b) by 544 days.

This patent is subject to a terminal disclaimer.

(21) Appl. No.: 17/150,511

(22) Filed: Jan. 15, 2021

(65) Prior Publication Data

US 2021/0128045 A1    May 6, 2021

Related U.S. Application Data

(63) Continuation of application No. 16/773,099, filed on Jan. 27, 2020, now Pat. No. 11,395,618, which is a
(Continued)

(51) Int. Cl.
*A61B 5/316* (2021.01)
*A61B 5/00* (2006.01)
(Continued)

(52) U.S. Cl.
CPC ............ *A61B 5/316* (2021.01); *A61B 5/0006* (2013.01); *A61B 5/14551* (2013.01); *A61B 5/30* (2021.01);
(Continued)

(58) Field of Classification Search
CPC ... A61B 5/316; A61B 5/0006; A61B 5/14551; A61B 5/30; A61B 5/282; A61B 5/301;
(Continued)

(56) References Cited

U.S. PATENT DOCUMENTS

| 4,800,495 A | * | 1/1989 | Smith ................ A61B 5/14551 600/323 |
|---|---|---|---|
| 4,940,060 A | | 7/1990 | Gu et al. |

(Continued)

FOREIGN PATENT DOCUMENTS

| CN | 86105980 A | 3/1988 |
|---|---|---|
| CN | 101579236 A | 11/2009 |

(Continued)

OTHER PUBLICATIONS

Asadi, F., et al., "Cardiac Arrhythmia Recognition with Robust Discrete Wavelet-Based and Geometrical Feature Extraction via Classifiers of SVM and MLP-BP and PNN Neural Networks," Computing in Cardiology, Issue 43, 2015, pp. 933-936.

(Continued)

*Primary Examiner* — Mallika D Fairchild
(74) *Attorney, Agent, or Firm* — Meunier Carlin & Curfman LLC

(57) ABSTRACT

The present disclosure facilitates capture of biosignal such as biopotential signals in microvolts, or sub-microvolts, resolutions that are at, or significantly below, the noise-floor of conventional electrocardiographic and biosignal acquisition instruments. In some embodiments, the exemplified system disclosed herein facilitates the acquisition and recording of wide-band phase gradient signals (e.g., wide-band cardiac phase gradient signals, wide-band cerebral phase gradient signals) that are simultaneously sampled, in some embodiments, having a temporal skew less than about 1 μs, and in other embodiments, having a temporal skew not (Continued)

more than about 10 femtoseconds. Notably, the exemplified system minimizes non-linear distortions (e.g., those that can be introduced via certain filters) in the acquired wide-band phase gradient signal so as to not affect the information therein.

22 Claims, 47 Drawing Sheets

Related U.S. Application Data continuation of application No. 15/248,838, filed on Aug. 26, 2016, now Pat. No. 10,542,897.

(60) Provisional application No. 62/354,668, filed on Jun. 24, 2016, provisional application No. 62/340,410, filed on May 23, 2016, provisional application No. 62/210,426, filed on Aug. 26, 2015, provisional application No. 62/210,427, filed on Aug. 26, 2015.

(51) Int. Cl.
| | |
|---|---|
| *A61B 5/1455* | (2006.01) |
| *A61B 5/282* | (2021.01) |
| *A61B 5/30* | (2021.01) |
| *A61B 5/301* | (2021.01) |
| *A61B 5/332* | (2021.01) |
| *A61B 5/369* | (2021.01) |

(52) U.S. Cl.
CPC ............ *A61B 5/282* (2021.01); *A61B 5/301* (2021.01); *A61B 5/332* (2021.01); *A61B 5/369* (2021.01); *A61B 5/7203* (2013.01); *A61B 5/7225* (2013.01); *A61B 5/725* (2013.01)

(58) Field of Classification Search
CPC ....... A61B 5/332; A61B 5/369; A61B 5/7203; A61B 5/225; A61B 5/725; A61B 5/308; A61B 5/14542; A61B 5/318; A61B 5/319
See application file for complete search history.

(56) References Cited

U.S. PATENT DOCUMENTS

| | | | |
|---|---|---|---|
| 5,020,540 | A | 6/1991 | Chamoun |
| 5,243,993 | A | 9/1993 | Alexander et al. |
| 5,823,957 | A | 10/1998 | Faupel et al. |
| 5,954,660 | A | 9/1999 | Legay et al. |
| 6,014,582 | A | 1/2000 | He |
| 8,521,266 | B2 | 8/2013 | Narayan et al. |
| 8,923,958 | B2 | 12/2014 | Gupta et al. |
| 9,289,150 | B1 | 3/2016 | Gupta et al. |
| 9,408,543 | B1 | 8/2016 | Gupta et al. |
| 9,597,021 | B1 | 3/2017 | Gupta et al. |
| 9,655,536 | B2 | 5/2017 | Gupta et al. |
| 9,737,229 | B1 | 8/2017 | Gupta et al. |
| 2001/0008953 | A1 | 7/2001 | Honda et al. |
| 2002/0029068 | A1* | 3/2002 | Lyster ................ A61N 1/3937 607/5 |
| 2003/0105403 | A1 | 6/2003 | Istvan et al. |
| 2006/0173364 | A1* | 8/2006 | Clancy .................. G16H 40/63 600/509 |
| 2006/0178706 | A1 | 8/2006 | Lisogurski et al. |
| 2013/0023781 | A1 | 1/2013 | Freeman et al. |
| 2013/0096394 | A1* | 4/2013 | Gupta .................. A61B 5/341 600/301 |
| 2013/0237793 | A1 | 9/2013 | Farrugia et al. |
| 2013/0303871 | A1 | 11/2013 | Brest van Kempen et al. |
| 2014/0023255 | A1 | 1/2014 | Lim et al. |
| 2014/0194758 | A1 | 7/2014 | Korenberg et al. |
| 2014/0375298 | A1 | 12/2014 | Garcia et al. |
| 2015/0133803 | A1 | 5/2015 | Gupta et al. |
| 2015/0216426 | A1 | 8/2015 | Burton et al. |
| 2015/0223743 | A1* | 8/2015 | Pathangay ............... A61B 5/18 600/509 |
| 2015/0374300 | A1* | 12/2015 | Najarian ................. G16Z 99/00 702/19 |
| 2016/0007862 | A1* | 1/2016 | Ku .......................... A61B 5/021 600/513 |
| 2016/0338629 | A1 | 11/2016 | Doerr |
| 2016/0378936 | A1 | 12/2016 | Burton et al. |
| 2018/0000371 | A1 | 1/2018 | Gupta et al. |
| 2018/0078146 | A1 | 3/2018 | Shadforth et al. |
| 2018/0249960 | A1 | 9/2018 | Gupta et al. |

FOREIGN PATENT DOCUMENTS

| | | |
|---|---|---|
| CN | 204428029 | 7/2015 |
| JP | 05-220121 | 8/1993 |
| JP | 2001-190510 | 7/2001 |
| JP | 2006-500964 | 1/2006 |
| JP | 2006-218304 | 8/2006 |
| JP | 2007-095968 | 4/2007 |
| JP | 2009-066203 | 4/2009 |
| JP | 2009-517117 | 4/2009 |
| JP | 2014502181 A | 1/2014 |
| JP | 2015-513413 | 5/2015 |
| WO | 2003/047427 | 6/2003 |
| WO | 2007/060609 | 5/2007 |
| WO | 2013/120014 | 8/2013 |
| WO | 2017/033164 | 3/2017 |

OTHER PUBLICATIONS

Ha, S., et al., "Integrated Circuits and Electrode Interfaces for Noninvasive Physiological Monitoring," IEEE Transactions on Biomedical Engineering, vol. 61, No. 5, 2014, pp. 1522-1537.

Hann, M., "Analog Fundamentals of the ECG Signal Chain," Texas Instruments, 2010, 87 pages.

Itu, L., et al., "A machine-learning approach for computation of fractional flow reserve from coronary computed tomography," Journal of Applied Physiology, vol. 121, No. 1, 2016, pp. 42-52.

Jobaggy, A., et al., "Biomedical Instrumentation," Typotex Kiado, Budapest University of Technology and Economics, Mar. 31, 2015, pp. 1-241.

Khan, M., et al., "Wavelet Based ECG Denoising Using Signal-Noise Residue Method," 5th International Conference on Bioinformatics and Biomedical Engineering, May 2011, 4 pages.

McKee, James J., et al., "Sigma-Delta Analogue-to-Digital Converters for ECG Signal Acquisition," Proceedings of 18th Annual International Conference of the IEEE Engineering in Medicine and Biology Society, Amsterdam, Netherlands, Oct. 31-Nov. 3, 1996, pp. 19-20.

Search Report, dated Feb. 6, 2019, received in connection with corresponding EP Patent Application No. 16838658.9.

International Preliminary Report on Patentability, dated Mar. 8, 2018, received in connection with corresponding International Patent Application No. PCT/IB2016/055125.

International Search Report and Written Opinion, dated Nov. 21, 2016, received in connection with corresponding International Patent Application No. PCT/IB2016/055125.

Office Action, dated Jan. 12, 2023, received in corresponding JP Patent Application No. 2022-010805 (and English translation).

Second Office Action, dated Jul. 5, 2022, received in related CN Patent Application No. 201880027446.X (and English translation).

Notice of Reasons for Rejection, dated May 31, 2022, received in corresponding JP Patent Application No. 2021116323 (and English translation).

Office Action, dated Mar. 24, 2022, received in related CA Patent Application No. 3,005,157.

Office Action, dated Oct. 7, 2022, received in related CA Patent Application No. 2,996,096.

Office Action, dated Jul. 28, 2023, received in related CA Patent Application No. 2,996,096.

Notification on Grant of the Patent, dated Nov. 4, 2022, received in related CN Patent Application No. 201880027446.X (and English translation).

(56) References Cited

OTHER PUBLICATIONS

Office Action, dated Feb. 22, 2022, received in related JP Application No. 2019-547503 (and English translation).

\* cited by examiner (CONT. 1)

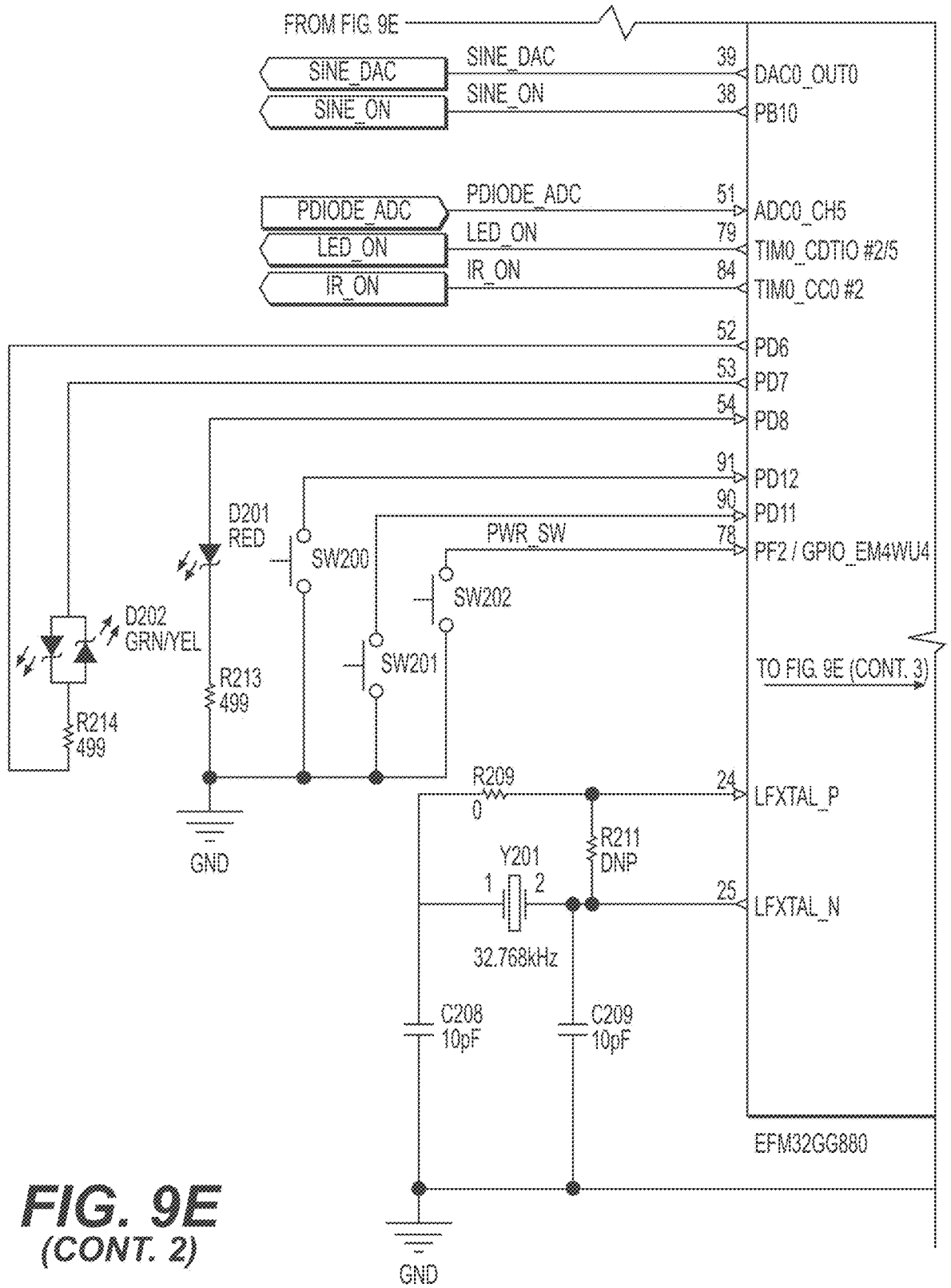
FIG. 9E (CONT. 2)

(CONT. 3)

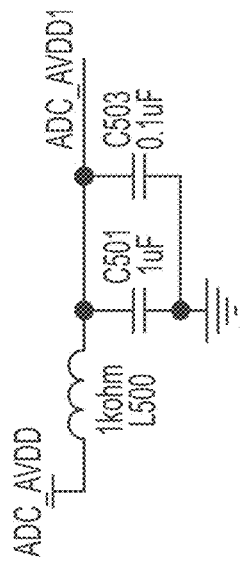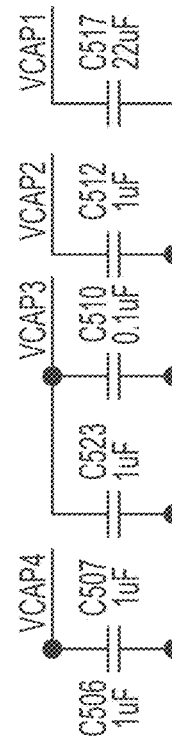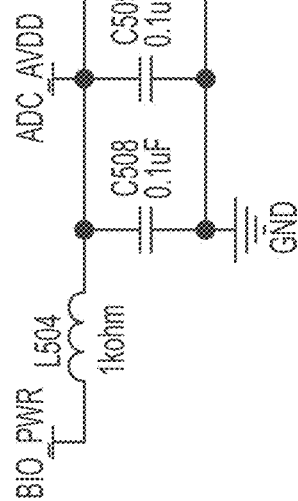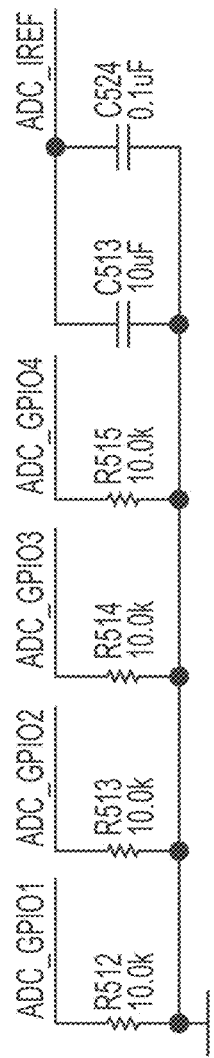
FIG. 9I
FIG. 9J
FIG. 9K

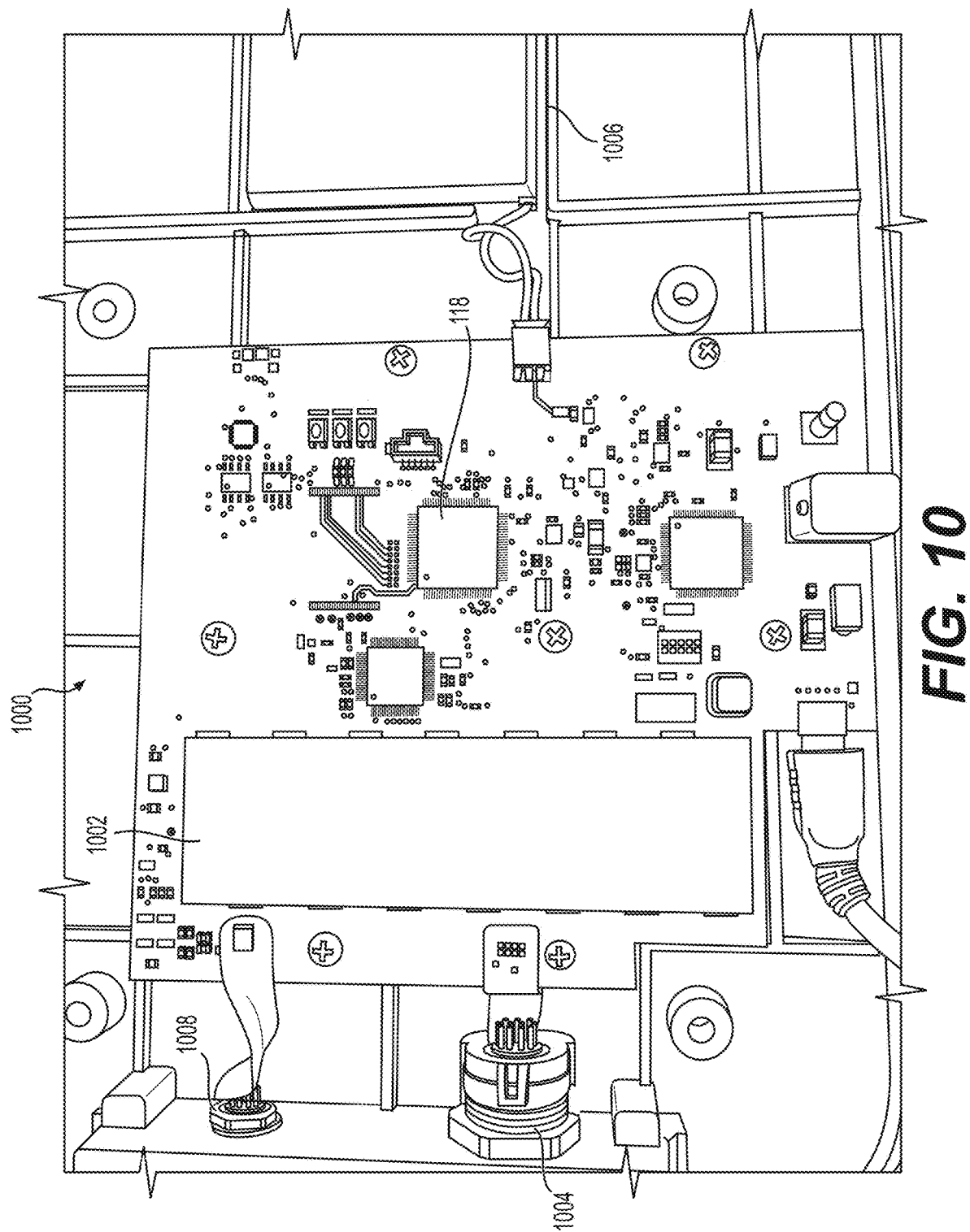

METHOD AND APPARATUS FOR WIDE-BAND PHASE GRADIENT SIGNAL ACQUISITION

CROSS-REFERENCE TO RELATED APPLICATIONS

This is a continuation application of U.S. patent application Ser. No. 16/773,099, titled "Method and Apparatus for Wide-Band Phase Gradient Signal Acquisition," filed Jan. 27, 2020, which is a continuation application of U.S. patent application Ser. No. 15/248,838, "Method and Apparatus for Wide-Band Phase Gradient Signal Acquisition," filed Aug. 26, 2016, now U.S. Pat. No. 10,542,897, which claims priority to, and the benefit of, U.S. Provisional Application Ser. No. 62/210,426, titled "Biosignal Acquisition Device," filed Aug. 26, 2015; U.S. Provisional Application Ser. No. 62/210,427, titled "Method for Biosignal Acquisition, Analysis and Data Presentation," filed Aug. 26, 2015; U.S. Provisional Patent Application Ser. No. 62/340,410, titled "Method and System for Collecting Phase Signals for Phase Space Tomography Analysis", filed May 23, 2016; and U.S. Provisional Application Ser. No. 62/354,668, "Method and System for Phase Space Analysis to Determine Arterial Flow Characteristics," filed Jun. 24, 2016, each of which is incorporated by reference herein in its entirety.

TECHNICAL FIELD

The present disclosure generally relates to a biosignal acquisition apparatus that acquires wide-band phase gradient signals that are used to non-invasively estimate functions of the body, such as heart functions, as well as to pinpoint and distinguish disease.

BACKGROUND

Conventional electrocardiographic instruments are configured to acquire and record biosignals such as biopotential signals relating to electrical activities of the heart. It is conventionally accepted that a large fraction of the total signal collected by such instruments is considered devoid of biological information. However, hidden within the full spectrum of physiologic signals emitted from the human body are information that can be used to pinpoint and distinguish disease.

Because these information can be captured in physiologic signals having signal power comparable to, or lower than, the noise floor of conventional electrocardiographic instruments, such information are difficult to extract, or not discernible, from the measured signals of these instruments. In some instances, the signal of interests has an order of magnitude of a few micro-Volts, and in other instances, even smaller. At such levels, interference from external energy sources such as man-made radiofrequency transmission and those that occur naturally as well as those from internal circuitries of the measurement instrument itself can affect the acquisition and recording of such information.

What are needed are devices, systems and methods that overcome challenges in the present art, some of which are described above.

SUMMARY

The present disclosure facilitates capture of biosignal such as biopotential signals in micro-Volts, or sub-micro-Volts, resolutions that are at, or significantly below, the noise-floor of conventional electrocardiographic and biosignal acquisition instruments. In some embodiments, the exemplified system disclosed herein facilitates the acquisition and recording of wide-band phase gradient signals (e.g., wide-band cardiac phase gradient signals, wide-band cerebral phase gradient signals) that are simultaneously sampled, in some embodiments, having a temporal skew among the channels of less than about 1 µs, and in other embodiments, having a temporal skew not more than 10 femtoseconds. Notably, the exemplified system minimizes non-linear distortions (e.g., those that can be introduced via certain filters such as phase distortions) in the acquired wide-band phase gradient signals so as to not affect the information therein that can non-deterministically affect analysis of the wide-band phase gradient signal in the phase space domain.

In an aspect, an apparatus (e.g., a BioSignal Acquisition Instrument (a "BSA instrument")) is disclosed. The apparatus includes two or more biosignal acquisition channels in which each biosignal acquisition channel comprises a gain amplifier configured to amplify biopotential signals received from an associated surface electrode placed on a patient (including mammals such as humans and test animals) to generate a wide-band phase gradient signal (e.g., wide-band cardiac gradient signal), wherein each biopotential signal is amplified without filtering that causes distortion in the generated wide-band cardiac phase gradient signal above about 1 kHz, wherein each output of the two or more biosignal acquisition channels feeds an analog-to-digital conversion circuit that simultaneously samples (e.g., having a temporal skew among the channels of less than about 1 µs or having a temporal skew not more than about 10 femtoseconds) each of the two or more biosignal acquisition channels (e.g., having at a sampling frequency above about 10 KHz, e.g., about 40 Khz, about 80 KHz, about 500 Khz, or higher) to generate a wide-band cardiac phase gradient signal data stream.

In some embodiments, the apparatus includes a potential biasing circuit that actively drives the patient to a varying potential (e.g., about $-1.5\ V_{AC\_rms}$) so as to shunt environmental noise currents flowing in the patient. In some embodiments, the varying potential has a value of about 2.0 $V_{AC\_rms}$, about 1.8 $V_{AC\_rms}$, about 1.6 $V_{AC\_rms}$, about 1.4 $V_{AC\_rms}$, about 1.2 $V_{AC\_rms}$, about 1.0 $V_{AC\_rms}$, about 0.8 $V_{AC\_rms}$, about 0.6 $V_{AC\_rms}$, about 0.4 $V_{AC\_rms}$, about 0.2 $V_{AC\_rms}$, about $-0.2\ V_{AC\_rms}$, about $-0.4\ V_{AC\_rms}$, about $-0.6\ V_{AC\_rms}$, about $-0.8\ V_{AC\_rms}$, about $-1.0 V_{AC\_rms}$, about $-1.2\ V_{AC\_rms}$, about $-1.4\ V_{AC\_rms}$, about $-1.6\ V_{AC\_rms}$, about $-1.8\ V_{AC\_rms}$, and about $-2.0\ V_{AC\_rms}$.

In some embodiments, the potential biasing circuit includes a waveform generator (e.g., a configurable waveform generator); and a drive circuit (e.g., a common mode amplifier) that couples to the waveform generator to actively drive the patient to an alternating potential (e.g., between about $-1.0$ VDC and about $-2.0$ VDC or between about $+1.0$ and about $+2.0$ VDC) so as to shunt environmental noise currents flowing in the patient.

In some embodiments, the potential biasing circuit actively drives the patient to an alternating potential having a minimum magnitude greater than a DC bias value associated with one or more of the surface electrodes placed on the patient (e.g., wherein the one or more surface electrodes have a half-cell potential).

In some embodiments, the apparatus includes a potential biasing circuit that actively drives the patient to a varying potential so as to shunt environmental noise currents flowing in the patient, wherein a substantial portion (e.g., greater than about 75%) of the varying potential is negative.

In some embodiments, the apparatus includes a potential biasing circuit that actively drives the patient to a constant potential so as to shunt environmental noise currents flowing in the patient.

In some embodiments, the apparatus includes a terminal block (e.g., for a given cable) comprising a plurality of connectors configured to couple a cable associated with a given surface electrode, wherein the cable comprises a shield layer that encapsulates one or more signal wires that carries a given biopotential signal received from the given surface electrode (e.g., wherein the shield layer does not terminate or connect to the surface electrode); and a noise-rejection circuit (e.g., a unity gain amplifier) having an input that receives the biopotential signal that is carried over the one or more signal wires and an output that couples to a connector of the plurality of connectors associated with the shield layer for the given cable so as to noise-reject interference over the cable by driving the biopotential signal received threat over the shield layer.

In some embodiments, the apparatus includes one or more terminal blocks each of which individually couples to a shield of a cable associated with a surface electrode; and a shield-equalizing circuit that injects a signal carried in the cable to the shield of the cable such that the injected signal approximately matches (e.g., within at least about 90%) the signal carried in the cable.

In some embodiments, the gain amplifier of each of the two or more biosignal acquisition channels directly couples to a terminal block (e.g., for a given cable) comprising a plurality of connectors, each of which couples a cable associated with a given surface electrode.

In some embodiments, each of the two or more biosignal acquisition channels comprises a low-pass anti-aliasing filter that filters below a Nyquist frequency of an operating sampling frequency of the analog-to-digital circuit (e.g., wherein the low-pass anti-aliasing filter filters at about 5 KHz for a 10 kSPS sampling rate).

In some embodiments, each of the two or more biosignal acquisition channels comprises a gain amplifier configured to amplify the received biopotential signal with a gain that provides a measurement resolution, with the analog-to-digital circuit, greater than about 0.3 µV per bit (e.g., wherein the analog-to-digital circuit provides a bit resolution of at least about 12 bits).

In some embodiments, the gain amplifier is powered by a single voltage supply (e.g., about +1.5 $V_{DC}$, about +3 $V_{DC}$, about +3.3 $V_{DC}$, about +5 $V_{D}C$, about +12 $V_{DC}$, and about +15 $V_{DC}$, about −1.5 $V_{DC}$, about −3 $V_{DC}$, about −3.3$V_{DC}$, about −5 $V_{DC}$, about −12 $V_{DC}$, and about −15 $V_{DC}$).

In some embodiments, the gain amplifier comprises an output that couples with a low-pass anti-aliasing filter that filters below a Nyquist frequency of an operating sampling frequency of the analog-to-digital circuit.

In some embodiments, the two or more biopotential channels comprises a number of channels selected from the group consisting of 2, 3, 4, 5, 6, 7, 8, 9, 10, 11, and 12 (e.g., wherein the number of cables and surface electrodes corresponds to the number of channels plus one, e.g., a common mode reference cable and surface electrode).

In some embodiments, the analog-to-digital circuit of each biosignal acquisition channel is configured to sample a wide-band cardiac phase gradient signal over a pre-defined voltage range of at least about 5 milli-Volt (mV) at a resolution of less than about 2 micro-Volt (µV) per bit and at a rate greater than about 5000 Hertz, wherein the two or more biosignal acquisition channel are simultaneously sampled with a temporal skew between channels less than 1 micro-seconds (µs), and wherein each biosignal acquisition channel comprises a signal-to-noise ratio of greater than about 15 dB (e.g., greater than 20 dB).

In some embodiments, the apparatus includes a sine wave generator that injects current (e.g., a fixed frequency sine wave, e.g., having a frequency between about 1 KHz and about 3 KHz) into the patient for thoracic impedance measurement.

In some embodiments, outputs of the sine wave generator are coupled to two or more surface electrodes associated with two of the biosignal acquisition channels.

In some embodiments, the drive circuit is coupled, at an output thereof, to a defibrillation protection circuit comprising a switching element that does not add thermal noise or avalanche noise to the signal path of the drive circuit. In some embodiments, the defibrillation protection circuit further comprises a shunt inductor coupled to a shunt resister of the one or more shunt resisters. In some embodiments, the defibrillation protection circuit includes a fast air gap relay that adds little, or no, distortions to the connected signal path and that can survive multiple defibrillator shocks with little, or no, degradation.

In some embodiments, each biosignal acquisition channel comprises a gain amplifier circuit (e.g., a gain amplifier circuit board or flex circuit) that directly couples to given surface electrode within an electrode housing.

In some embodiments, each gain amplifier circuit associated with a given electrode housing feeds a corresponding analog-to-digital circuit located in a second housing, the second housing being connected to the given electrode housing via a cable.

In another aspect, a system is disclosed, wherein the system includes two or more biosignal acquisition channels, each biosignal acquisition channel comprising a gain amplifier configured to amplify biopotential signals received from a corresponding surface electrode placed on a patient to generate a wide-band cardiac phase gradient signal, wherein each biopotential signal is amplified without filtering that causes distortions in the generated wide-band cardiac phase gradient signal above about 1 kHz; and two or more analog-to-digital circuits, each corresponding to the two or more biosignal acquisition channels, wherein each output of the two or more biosignal acquisition channels feeds a corresponding analog-to-digital circuit of the two or more analog-to-digital circuits, and wherein the two or more analog-to-digital circuits simultaneously sample (e.g., having a temporal skew less than about 1 µs) the two or more biosignal acquisition channels (e.g., having at a sampling frequency above about 10 KHz, e.g., about 40 KHz, about 80 KHz, about 500 KHz, or higher) to generate two or more wide-band cardiac phase gradient signal data streams each associated with a given a wide-band cardiac phase gradient signal.

In another aspect, a method is disclosed of generating wide-band cardiac phase gradient signal data. The method includes amplifying (e.g., a gain amplifier circuit), biopotential signals received from a plurality of surface electrodes each placed on a patient to generate a wide-band cardiac phase gradient signal for each of the received biopotential signals, wherein each biopotential signal is amplified without filtering that causes distortions in the generated wide-band cardiac phase gradient signal above about 1 kHz; and simultaneously sampling (e.g., AD converters), at a sampling frequency greater than about 50 KHz, each of the amplified wide-band cardiac phase gradient signals to generate wide-band cardiac phase gradient signal data streams, wherein the amplified wide-band cardiac phase gradient signals are simultaneous sampled so as to have a temporal skew among each of the amplified wide-band cardiac phase gradient signals less than about 1 μs.

In another aspect, a system is disclosed wherein the system is configured to prevent self-interference from communication hardware associated with a biopotential acquisition subsystem that captures wide-band cardiac phase gradient signal data. The system includes the biopotential acquisition subsystem comprising two or more biosignal acquisition channels, each biosignal acquisition channel comprising a gain amplifier configured to amplify biopotential signals having a signal level less than about 5 mV received from a corresponding surface electrode placed on a patient to generate a wide-band cardiac phase gradient signal; and a wireless communication subsystem comprising an antenna and a transceiver, the transceiver being configured to transmit, via the antenna, data stream associated with the wide-band cardiac phase gradient signal to a remote computing device, wherein the wireless communication subsystem is configured to disable transmission of electromagnetic radiation over the antenna when the biopotential acquisition subsystem is acquiring the wide-band cardiac phase gradient signal, and wherein the wireless communication subsystem is configured to enable transmission of electromagnetic radiation immediately following acquisition of the wide-band cardiac phase gradient signal by the biopotential acquisition subsystem.

In some embodiments, the wireless communication subsystem comprises a transmitter selected from the group consisting of a Wi-Fi transmitter, a cellular data service transmitter (e.g., a Global System for Mobile Communication (GSM) transmitter, a Universal Mobile Telecommunications System (UMTS) transmitter, a 3G network transmitter, a 4G network transmitter), a mobile satellite communication service transmitter, and a Short-range point-to-point communication transmitter (e.g., a Bluetooth transmitter or a Wireless USB transmitter).

BRIEF DESCRIPTION OF DRAWINGS

FIGS. 9A, 9B, 9C, 9D, 9E, 9F, 9G, 9H, 9I, 9J, 9K, 9L, 9M, 9N, 9O, 9P, 9Q, 9R, 9S, 9T, 9U, and 9V, are circuit diagrams of a wide-band cardiac phase gradient signal acquisition system in accordance with an illustrative embodiment.

FIG. 10 is a photograph of an example biosignal acquisition ("BSA") board that includes the wide-band cardiac phase gradient signal acquisition system of FIG. 9 in accordance with an embodiment.

FIG. 12, comprising

FIG. 13, comprising

FIG. 15, comprising

FIG. 16, comprising

FIG. 17, comprising

FIG. 19, comprising

DETAILED DESCRIPTION

Figure 1:
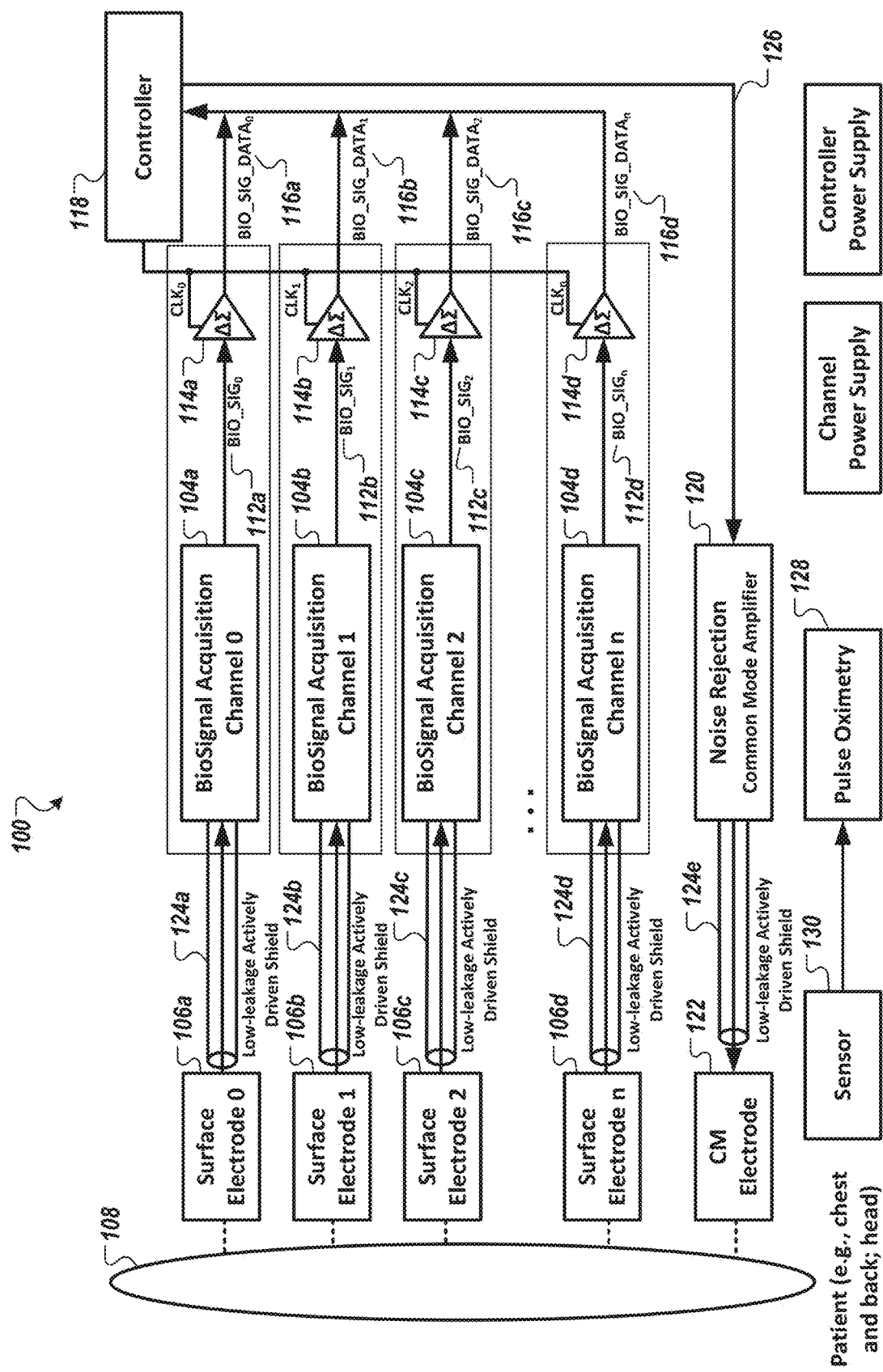
FIG. 1 is a diagram of an example apparatus configured to acquire wide-band cardiac phase gradient signals in accordance with an embodiment.

The components in the drawings are not necessarily to scale relative to each other and like reference numerals designate corresponding parts throughout the several views.

FIG. 1 is a diagram of an example apparatus 100 configured to acquire wide-band cardiac phase gradient signals in accordance with an embodiment. As shown in FIG. 1, the apparatus 100 includes a number of biosignal acquisition channels 104 (e.g., channels 1 to 12 and shown as "biosignal acquisition channel 0" 104a, "biosignal acquisition channel 1" 104b, "biosignal acquisition channel 2" 104c, and "biosignal acquisition channel n" 104d) that is operatively coupled to a corresponding surface electrode 106 (shown as surface electrodes 106a, 106b, 106c, and 106d) to acquire wide-band cardiac phase gradient signals from a patient's chest and/or back 108. In some embodiments, the biosignal acquisition channels 104 are configured to acquire wide-band phase gradient signals (e.g., wide-band cerebral phase gradient signal) at various locations, for example, from a patient's head. In other embodiments, wide-band phase gradient signals are acquired from other areas of the body, e.g., in proximity to certain organs.

Referring still to FIG. 1, each biosignal acquisition channel 104 includes one or more amplifier circuits 110 (not shown—see FIG. 4) that amplifies biopotential signals received thereto to generate an amplified biopotential signal 112 (shown as "BIO_SIG$_0$" 112a, "BIO_SIG$_1$" 112b, "BIO_SIG$_2$" 112c, and "BIO_SIG$_n$" 112d) corresponding to wide-band cardiac phase gradient signal having little or no non-linear distortions introduced into the signal path.

Example of such non-linear distortions includes phase distortions that may affect the signal at different frequencies which can distort the wide-band cardiac phase gradient signal in the phase space domain. In addition, non-linear distortions includes variability in the signal paths among the different acquisition channels.

As shown in FIG. 1, the biosignal acquisition channels 104 are coupled to a corresponding analog-to-digital conversion circuit 114 (shown as circuits 114a, 114b, 114c, 114d) that are simultaneously sampled such that a temporal skew among each of the sampled signal is less than about 1 μs (e.g., not more than about 10 femtoseconds), to convert the amplified biopotential signal 112 to time-series data 116 (shown as "BIO_SIG_DATA$_0$" 116a, "BIO_SIG_DATA$_1$" 116b, "BIO_SIG_DATA$_2$" 116c, and "BIO_SIG_DATA$_n$" 116d) associated with the wide-band cardiac phase gradient signal and that are received by a controller 118 for subsequent analysis (e.g., in phase space domain).

The controller 118 manages the acquisition and recording of the biosignal from the patient and manages the transmission of recorded information (including, e.g., biosignals, instrument identification, and patient identification) to a remote data storage location. In some embodiments, the controller 118 manages the acquisition and recording of the biosignal from the patient and interfaces with a computing device to transmit recorded information (including, e.g., biosignals, instrument identification, and patient identification) to a remote data storage location. In some embodiments, the processing is used to determine cardiac performance, including but not limited to, predicting Ejection Fraction (in percentage), assessing ischemic burden, and/or detecting coronary artery disease, from the wide-band cardiac phase gradient signals generated from the acquired biopotential signals. In some embodiments, the controller 118 manages the acquisition and recording of the biosignal from the patient and manages the processing, e.g., locally or remotely, of the biosignal to present results on a graphical user interface operatively connected to the controller.

In some embodiments, in addition to being used to collect the wide-band cardiac phase gradient signals 112, the surface electrodes 106 are also used to collect transthoracic impedance readings. The impedance readings, in some embodiments, are used to normalize the wide-band cardiac phase gradient signal data, e.g., for impedance, during the subsequent analysis.

In some embodiments, the system 100 includes a pulse oximeter circuit 128 that operates with a pulse oximeter (PO2) sensor 130 to collect oxygen saturation readings. The collected oxygen saturation readings may be used to augment the acquired wide-band cardiac phase gradient signal data. In some embodiments, data associated with oxygen saturation readings are collected concurrently with the acquisition of the wide-band cardiac phase gradient signal data. In other embodiments, data associated with oxygen saturation readings are independently collected. Other sensors or features may also be included.

Referring still to the embodiment of FIG. 1, each analog-to-digital conversion circuit 114 includes a high-speed sigma-delta converter that is sampled simultaneously to have a temporal skew of less than about 1 us (e.g., not more than about 10 fs (femtosecond)) with the other biosignal acquisition channels. The output of the analog-to-digital conversion circuit 114 is preferably a serial data stream that is provided to the controller 118, e.g., as a time series data stream. The controller 118, in some embodiments, is configured to aggregate the acquired data 116 (associated with a wide-band cardiac phase gradient signal) over a pre-defined period and transmit the collected data to a repository (e.g., a storage area network). In some embodiments, the acquired data 116 are transmitted as time series data in a file. In some embodiments, the file includes one or more, e.g., time series data, instrument identification data, instrument performance data, and/or patient identification data.

In other embodiments, the controller 118 is configured to store the acquired data 116, which is processed locally. In some embodiments, the acquired data is processed by the acquisition system to determine wide-band cardiac phase gradient signals for a given measurement, which is then transmitted as the collected data to the repository. Each time series data and wide-band cardiac phase gradient signal data sets may have a duration period between about 100 seconds and about 200 seconds.

The wide-band cardiac phase gradient signal data comprises a wide range of frequencies, in some embodiments, having a sampling greater than about 5 KHz (Kilo-Hertz). In some embodiments, the wide-band cardiac phase gradient signal data comprises a sampling frequency greater than about 10 KHz. In some embodiments, the wide-band cardiac phase gradient signal data comprises a sampling frequency greater than about 40 KHz. In some embodiments, the wide-band cardiac phase gradient signal data comprises a sampling frequency greater than about 80 KHz. In some embodiments, the wide-band cardiac phase gradient signal data comprises a sampling frequency greater than about 500 KHz. In various embodiments, the wide-band cardiac phase gradient signal data has little or no non-linear distortion within its range of sampled frequencies.

In addition, the wide-band cardiac phase gradient signal data has a range of at least about 5 mV (millivolt) at a resolution of less than about 2 μV (microvolt) per bit. In some embodiments, the wide-band cardiac phase gradient signal data has a resolution of about, or less than, ½ μV per bit.

Because ½ μV is below the thermal noise associated with most conventional circuitries, the system 100 includes several features to reduce interference from its own circuitries as well as from external energy sources such as radiofrequency transmissions.

Figure 2:
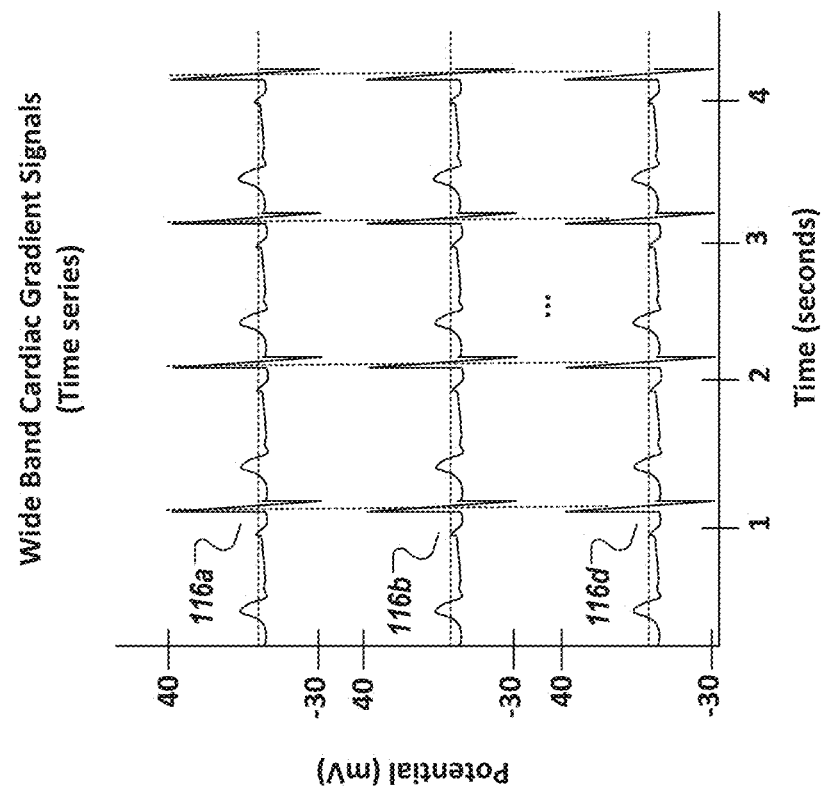
FIG. 2 is a diagram of a single biosignal acquisition channel in accordance with an illustrative embodiment.

FIG. 2 is a diagram of an example wide-band cardiac gradient signal data shown as a time series data, in accordance with an embodiment. The wide-band cardiac phase gradient signal data is generated as a differential of two or more of the acquired biopotential signals. In some embodiments, the patient is actively driven to a common mode potential and the acquired biopotential signal includes the common mode potential. In such embodiments, the wide-band cardiac gradient signal data is the remaining signal with the common-mode reference removed, e.g., via computation. As presented, the wide-band cardiac gradient signal data has been amplified and normalized with the common-mode reference removed. In other embodiments, the acquired biopotential signal is processed via hardware circuitry to remove or normalized the applied common mode potential.

Figure 3:
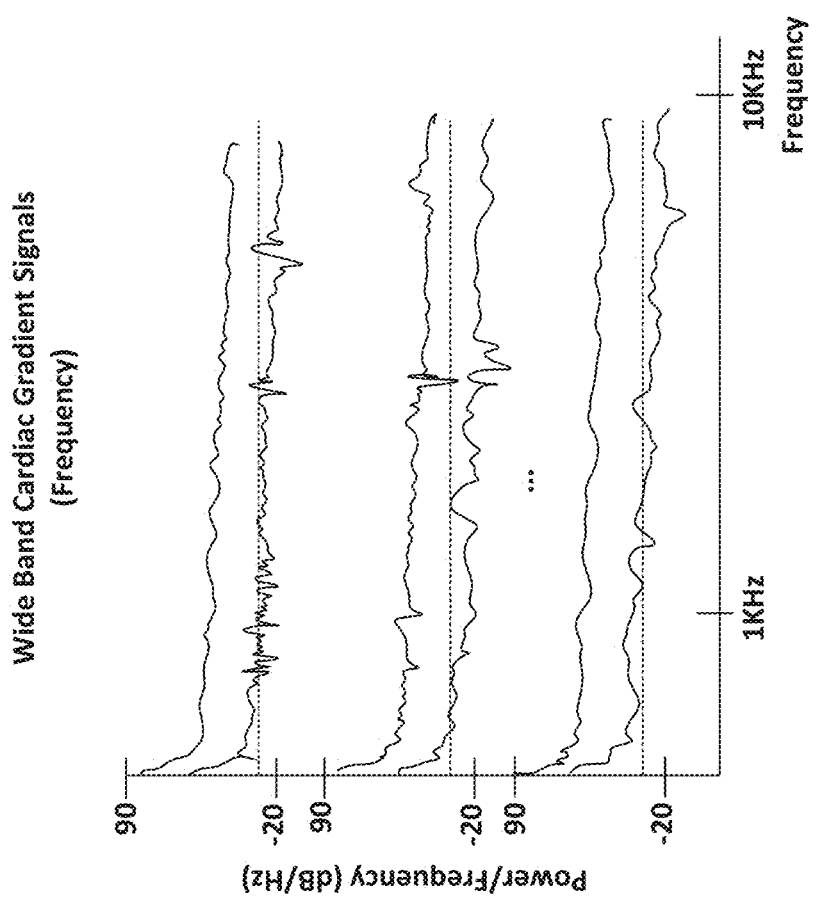
FIG. 3 is a diagram of the example wide-band cardiac gradient signal data of FIG. 2 shown in the frequency domain, in accordance with an embodiment.

FIG. 3 is a diagram of the example wide-band cardiac gradient signal data of FIG. 2 shown in the frequency domain, in accordance with an embodiment.

It is discovered that wide-band biopotential signals, having energy and frequency components beyond those of conventional electrocardiography (ECG) and traditionally perceived to be random noise, includes measurable data of the heart physiology that can be discriminated by genetic algorithms (and other machine learning algorithms) to assess regional flow characteristics of the heart, including an estimated value for stenosis an identification of ischemia, a fractional flow reserve (FFR) of specific arteries and branches thereof. Noise removal (e.g., by applying cleaning techniques to the data resulting in the same amount of data as prior to noise removal) is a fundamental step in signal processing. However, the exemplified method and system processes the entire obtained biopotential signals without any noise removal operations in the wide-band region of the signal. What has heretofore been perceived and/or classified as unwanted noise in the wide-band data is, in many cases, the signal of interest. Examples of noise removal that is not performed include, but not limited to, analog-based low-pass filters, band-pass filters, high-pass filters and well as digital-based filters such as FIR filters, Butterworth filters, Chebyshev filters, median filters, among others.

In addition to removing information of interest from the acquired wide-band signals, certain circuit elements can introduce non-linear distortions that can affect analysis in phase space of the wide-band phase gradient signals and are not included, or minimized, in the signal path of the exemplified system. For example, certain analog pass filters (e.g., analog-based low-pass filters, band-pass filters, high-pass filters and well as digital-based filters such as FIR filters, Butterworth filters, Chebyshev filters, median filters, among others, as discussed above) may introduce phase distortions which may result in non-linear group delays among the multiple acquisition channels or introduce frequency-dependent distortions in individual acquisition channels. In addition, certain circuit elements such as field-effect transistors (e.g., MOSFET) may introduce unnecessary capacitance and gate-field effect noise to the signal path. In addition, certain semiconductor and insulating materials with avalanche breakdown effects (e.g., in Zener diodes) may introduce avalanche noise to the signal path.

In some embodiments, the signal may be processed via phase linear operations to allow for analysis of specific aspects of the high-frequency wide-band data. In some embodiments, the signal may be processed via operations or circuitries that affect frequencies completely outside the band of interest. In some embodiments, these frequencies that are filtered are in the radiofrequency range or above.

As shown in FIG. 3, the wide-band cardiac gradient signal has a frequency component greater than about 1 kHz, which is significantly higher than convention electrocardiogram measurements. In some embodiments, the wide-band cardiac gradient signal has a frequency component up to about 4 kHz (e.g., about 0 Hz to about 4 kHz). In some embodiments, the wide-band cardiac gradient signal has a frequency component up to about 5 kHz (e.g., about 0 Hz to about 5 kHz). In some embodiments, the wide-band cardiac gradient signal has a frequency component up to 6 kHz (e.g., about 0 Hz to about 6 kHz). In some embodiments, the wide-band cardiac gradient signal has a frequency component up to about 7 kHz (e.g., about 0 Hz to about 7 kHz). In some embodiments, the wide-band cardiac gradient signal has a frequency component up to about 8 kHz (e.g., about 0 Hz to about 8 kHz). In some embodiments, the wide-band cardiac gradient signal has a frequency component up to 9 kHz (e.g., about 0 Hz to about 9 kHz). In some embodiments, the wide-band cardiac gradient signal has a frequency component up to 10 kHz (e.g., about 0 Hz to about 10 kHz). In some embodiments, the wide-band cardiac gradient signal has a frequency component up to 50 kHz (e.g., about 0 Hz to about 50 kHz).

Figure 4:
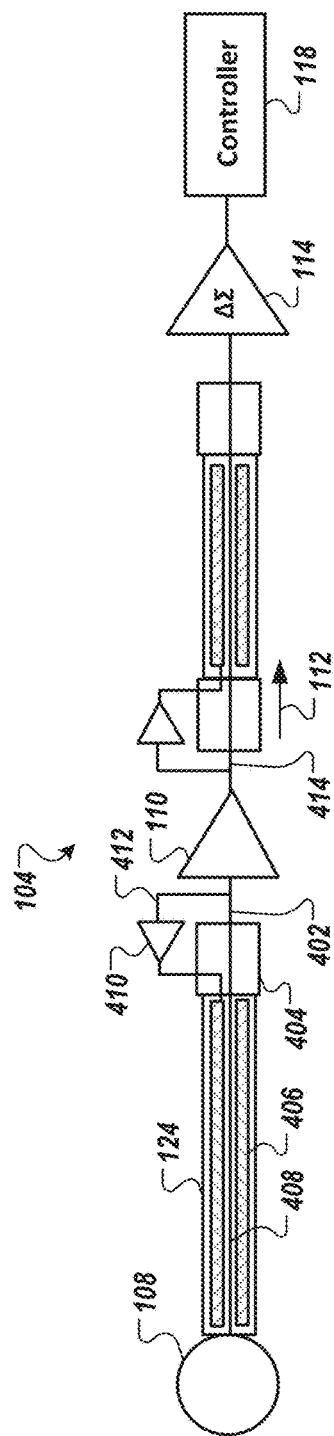
FIG. 4 is a detailed diagram of a biosignal acquisition channel of FIG. 1 in accordance with an illustrative embodiment.

FIG. 4 is a detailed diagram of a biosignal acquisition channel 104 in accordance with an illustrative embodiment. The biosignal acquisition channel 104 includes an operational amplifier 110 having an input 402 that directly couples to a terminal 404 to operatively couple to the surface electrode 106 such that little, or no, non-linear distortions (e.g., such as those discussed herein) are introduced into the signal path. To this end, active and passive filters are preferably not placed in the signal path to reduce distortions that they may be introduced during operation. The operational amplifier 110 preferably provides a gain greater than about 15 dB (decibel) to generate the wide-band phase gradient signal. In some embodiments, the operational amplifier 110 provides a gain greater than about 20 dB. The output 414 of the operational amplifier 110, in some embodiments, is coupled to the analog-to-digital conversion circuit 114 (e.g., sigma-delta ADC).

In some embodiments, each biosignal acquisition channel 104 electrically couples to a respective surface electrode 106 over a cable 124 (e.g., a co-axial cable and shown as cable 124a, 124b, 124c, and 124d) that employs an active noise reduction system. The active noise reduction system is used, in some embodiments, with the cable 124 between the surface electrode 108 and the operational amplifier 110 as well as with a cable 416 between the operational amplifier and the analog-to-digital conversion circuit 114 where such circuits are located on different circuit board.

As shown in FIG. 4, the biosignal acquisition channel 104 include an active noise reduction system that actively shields the signal-carrying conductor 408 in the cable 124 between the surface electrode 108 and the operational amplifier 110. The cable 124 includes a first conductor 408 (i.e., the signal-carrying conductor 408) that, in some embodiments, is a pair of twisted wires and a second conductive layer 406 that surrounds the conductor 408. The active noise reduction system includes a shield-equalizing circuit comprising an operational amplifier 410 that injects the signal carried in the conductor 408 to the shield 406 of the cable 124 such that the injected signal approximately matches (e.g., within at least about 90%) the signal carried in the cable. Put another way, the active noise reduction system drives the shield 406 to about the same electric potential as the conductor 408, which reduces the electrical leakage between the conductor 408 and the shield 406.

In some embodiments, the operational amplifier 410 is configured as a unity gain amplifier. The input 412 of the operational amplifier 410 is coupled to the input of the gain amplifier 110, which is also coupled to the terminal 404. The output 414 of the operational amplifier 410 is coupled to the conductive layer 406 of the cable 124.

Figure 5:
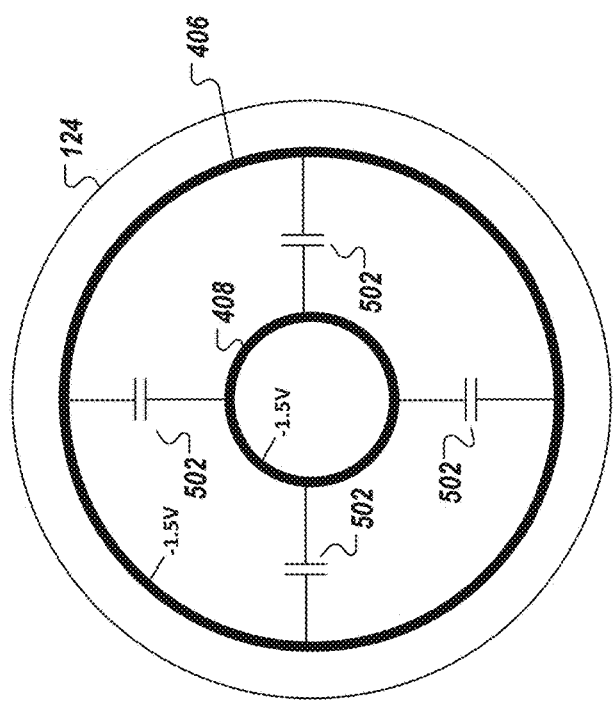
FIG. 5 is a diagram of a method of matching potential of a signal-carrying conductor and a shield-conductor in accordance with an embodiment.

FIG. 5 is a diagram illustrating operations of the shield-equalizing circuit in accordance with an illustrative embodiment. As shown in FIGS. 4 and 5, the shield conductor 406 of cable 124 surrounds the signal conductor 408 and is driven by the operational amplifier 410 to a potential that matches, or nearly matches, the signal conductor 408. For example, where the signal conductor 408 carries a potential of about −1.5V, the operational amplifier 410 drives the shield conductor 406 also to about −1.5V. Because the potential between the signal conductor 408 and shield conductor 406 matches, or nearly matches, the dielectric electric field between them is minimized. To this end, a perturbation introduced to the signal-conductor 408 by the shield-conductor 406 due to perturbation of the shield-conductor 406 from external interference is dampened.

Example Noise Rejection Subsystem

To improve the signal quality of the measured wide-band cardiac gradient signal 112, the exemplified system 100 (e.g., as shown in FIG. 1), in some embodiments, includes a noise rejection system 120 that eliminates, or reduces, environmental noise currents flowing in the patient's body that might interfere with the biopotential measurement. The noise rejection system 120 is configured to actively drive the patient's body to a potential that shunts environmental noise currents during normal operation. Environmental noise may be generated from a variety of environmental sources including nearby electronics, transmission devices, and local AC power systems, among others. Any or all of these sources may generate voltages at the measurement electrodes that can render a patient's biopotential un-measurable or reduce the resolution of the measurement.

As shown in FIG. 1, the noise rejection system 120 is operatively coupled to a surface electrode 122 that is in electrical contact (e.g., directly or via a conductive gel or paste) with a surface of the body 108. In some embodiments, the noise rejection system 120 actively drives the body 108 to a varying potential that varies between two negative potential values. It is found that driving the common mode potential of the body between two negative potential values facilitates the rejection of noise currents in the body while removing the need to use filters that may introduce non-linear distortions into the measured signals.

In some embodiments, a given surface electrode may be used in conjunction with gels or other coupling media or devices that can form a half-cell potential in the signal path when measuring the wide-band cardiac phase gradient signal. For example, silver chloride gel may introduce a 300 mV biased in the signal path. In some embodiments, the noise rejection system 120 actively drives the body 108 to a varying potential that varies between two negative potential values such that the magnitudes of negative potential values are greater than the expected half-cell potential DC bias value associated with the surface electrodes.

Referring still to FIG. 1, noise rejection system 120 is electrically coupled, via a cable 124e, to a common-mode electrode 122 that is placed on the body 108. In some embodiments, an active noise reduction system, e.g., similar to that used in the biosignal acquisition, is used to actively shield the signal-carrying conductor in the cable 124e between the common-mode surface electrode 122 and the noise rejection system 120. In other embodiments, a passive shield is used in which the shield-conductor of the cable 124e is coupled to the ground plane of the system 100.

The noise rejection system 120, in some embodiments, includes a waveform generator and an operational amplifier. In some embodiments, the waveform generator is a fixed-frequency oscillator. In other embodiments, the waveform generator is a microcontroller that is electronically programmable to generate an analog output that can vary in frequency and amplitude range, e.g., based on control signals outputted from the controller 118. In FIG. 1, the noise rejection system 120 is shown operatively coupled to the controller 118 via control line 126.

In some embodiments, the noise rejection system 120 actively drives the body 108 to a varying potential that varies between a negative potential value and a positive potential value.

In some embodiments, the noise reduction system 120 actively drives the body 108 to a varying potential that varies between two positive potential values.

In other embodiments, the noise reduction system 120 actively drives the body to a constant potential (e.g., a value between about $-1.5$ $V_{DC}$ and about $+1.5$ $V_{DC}$ or a value between about $-3.0$ $V_{DC}$ and about $+3$ $V_{DC}$).

Example BSA System

Figure 6:
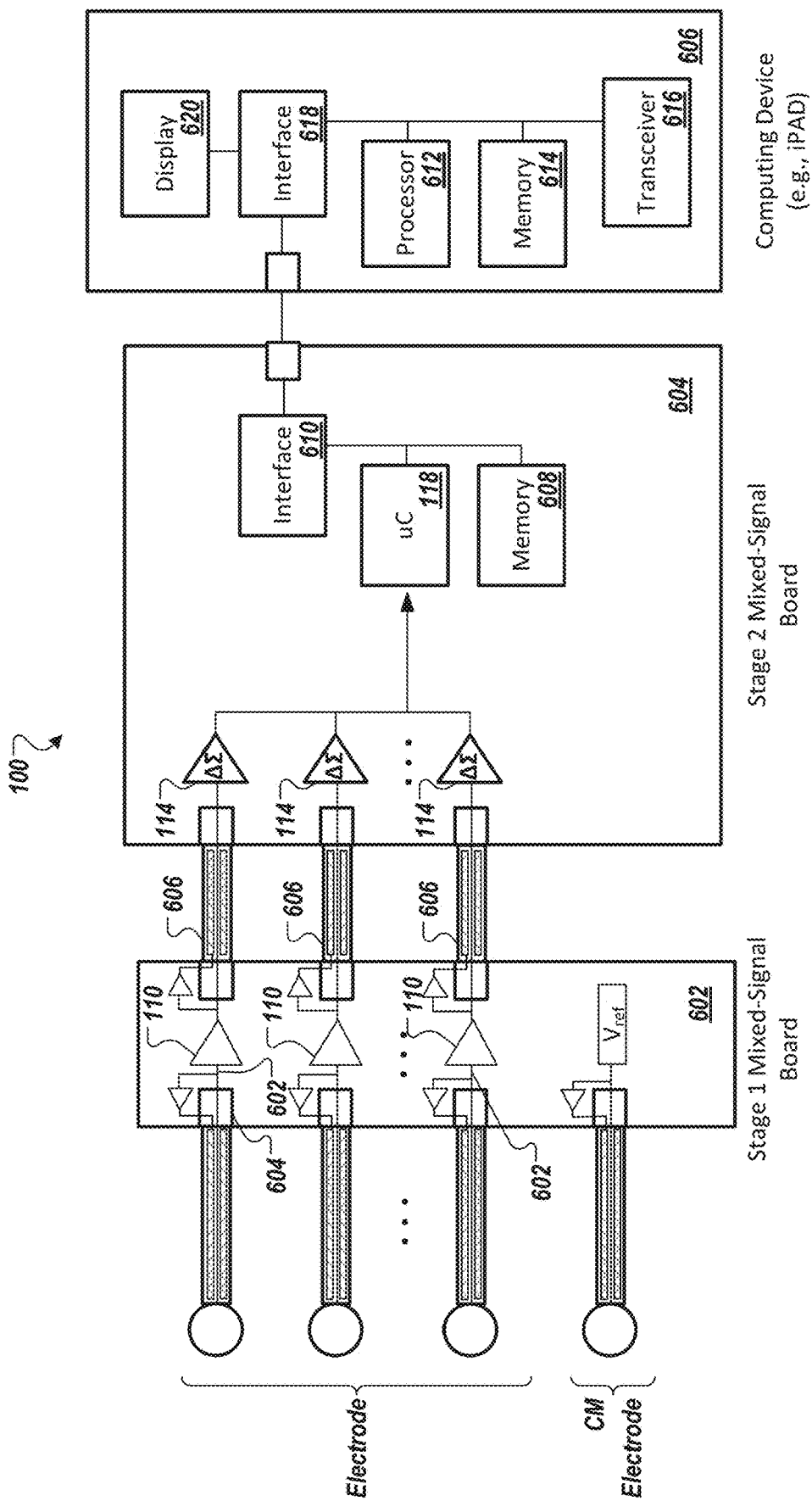
FIG. 6 is a diagram of an example system in accordance with an illustrative embodiment.

FIG. 6 is a diagram of an example system 100 in accordance with an illustrative embodiment. As shown in FIG. 6, the system 100 includes a first stage mixed-signal board 602 that includes the biosignal acquisition channel 104 as described in relation to FIG. 1. The first stage mixed-signal board 602 is operatively coupled to a second stage mixed-signal board 604 over one or more cables 606 that carries the amplified biopotential signals 112. The second stage mixed-signal board 604 includes the analog-to-digital conversion circuit 114 and a microcontroller 118, as described in relation to FIG. 1. The second stage mixed-signal board 604 communicates to a third stage controller board 606 that provides communication and interface functionality.

As shown in FIG. 6, the second stage mixed-signal board 604 includes memory 608 and interface circuit 610. The memory 608 locally stores the acquired biopotential signal data 116 associated with the wide-band cardiac phase gradient signal data for a given measurement prior to the data 116 being sent to the third stage controller board 606 to be transmitted to remote storage. The interface circuit 610, in some embodiments, includes communication isolation circuitries such as optical isolators and other isolation circuitries such as, but not limited to, for power and ground. The third stage controller board 606 includes a processor 612, a memory 614, a communication transceiver 616, and an interface circuit 618 that, collectively, is configured to operate with the second stage mix-signal board 604 to offload the wide-band cardiac phase gradient signal data 116 acquired thereat to transmit, e.g., via wireless communication to remote storage (e.g., repositories in the cloud). In some embodiments, the third stage controller board 606 is configured to analyze the wide-band cardiac phase gradient signal data acquired thereat and present outputs of the analysis at a graphical user interface associated therewith. In some embodiments, the third stage controller board 606 is a part of a custom computing device. In other embodiments, the third stage controller board 606 a part of a general computing device.

Integrated Surface Electrode and Amplifier

In another aspect, a wide-band cardiac phase gradient signal acquisition system that includes integrated surface electrodes and amplifier circuits is disclosed. By positioning the amplifier circuit closer to the point of signal acquisition at the surface electrode, higher signal quality can be attained because the signal path between the surface electrode and the amplifier circuit in which interference may be introduced is reduced, if not removed.

Figure 7:
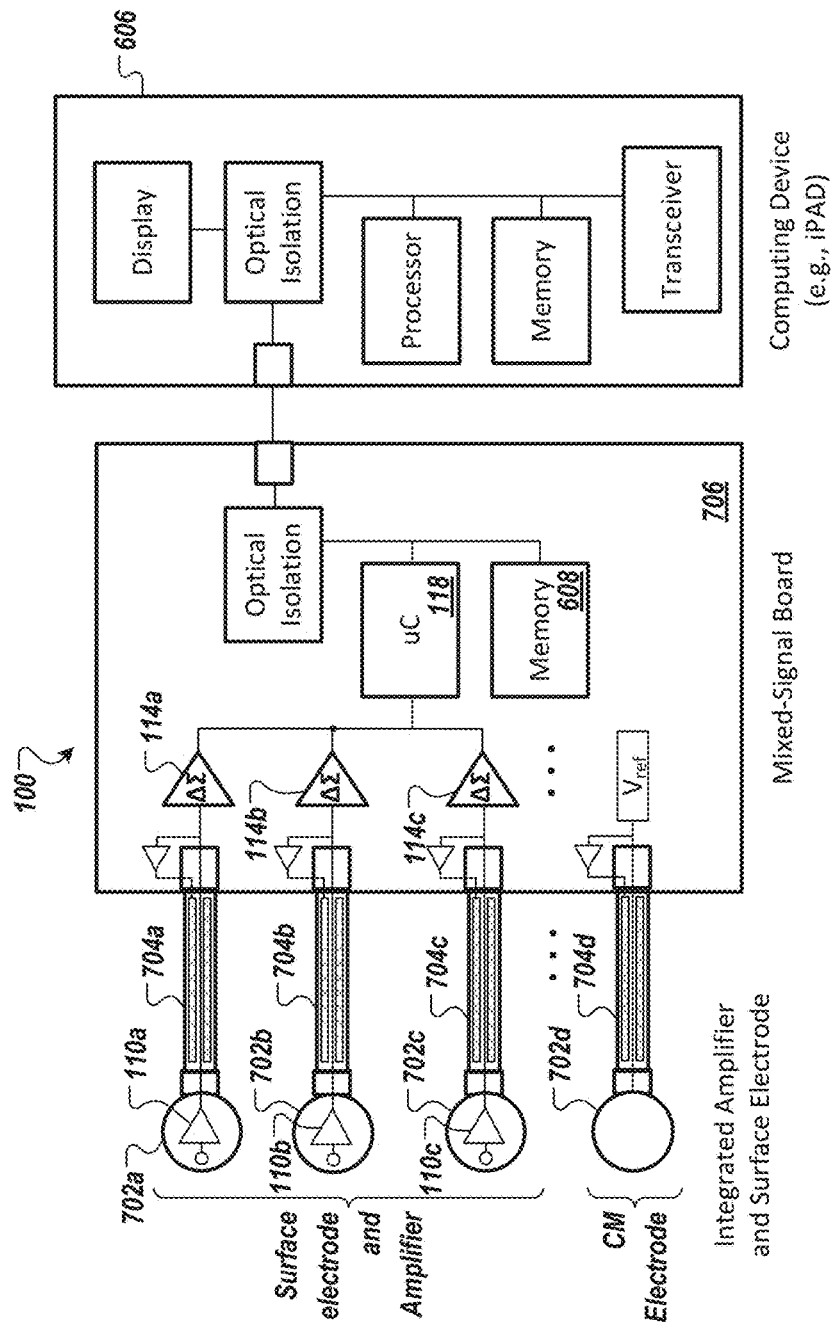
FIGS. 7 and 8 are diagrams of a wide-band cardiac phase gradient signal acquisition system with integrated surface electrode and amplifier circuit in accordance with an illustrative embodiment.
Figure 8:
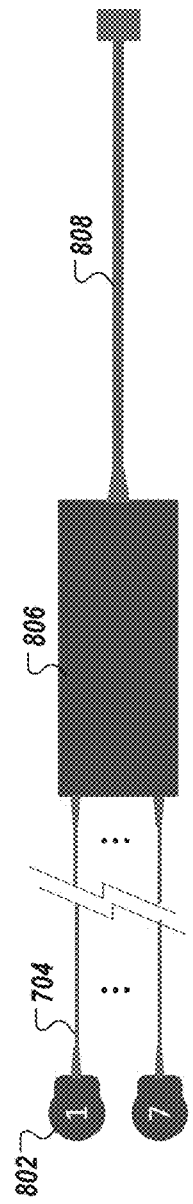

FIGS. 7 and 8 are diagrams of a wide-band cardiac phase gradient signal acquisition system 100 with an integrated surface electrode and amplifier circuit in accordance with an illustrative embodiment. As shown in FIG. 7, the operational amplifier 110 (shown as amplifier 110a, 110b, and 110c) is positioned on a circuit board or flexible circuit that is housed within surface electrode housing 702 (shown as surface electrode housing elements 702a, 702b, and 702c). In some embodiments, inputs 402 (see, e.g., FIG. 4) of the operational amplifier 110 directly couples to a conductive pad of the surface electrode that contacts the patient's body 108. The output 412 (see, e.g., FIG. 4) of the operational amplifier 110 is coupled, via cable 704 (shown as cables 704a, 704b, 704c), to the analog-to-digital conversion circuit 114 (shown as ADC circuits 114a, 114b, and 114c).

In some embodiments, an active noise reduction system, e.g., similar to that described in relation to FIG. 1, is used to actively shield the signal-carrying conductor in the cable 704 between the operational amplifier 110 and the analog-to-digital conversion circuit 114. In other embodiments, a passive shield is used in which the shield-conductor of the cable 704a-704c is coupled to the ground plane of the system 100.

As further shown in FIG. 7, the analog-to-digital conversion circuit 114 is positioned on a mixed-signal board 706 that also includes the microcontroller 118 and memory 608 that, collectively, aggregates the acquired biopotential signal data associated with the wide-band cardiac phase gradient signal and provides the data to a control board 606 to offload to remote storage.

As shown in FIG. 8, the integrated surface electrodes and amplifier circuits, as shown and described in relation to FIG. 7, are positioned and encapsulated in a snap button housing 802 for a given acquisition channel. In some embodiments, the snap button housing 802 is about ¾ inch in diameter. In other embodiments, snap button housing 802 may have different diameters. The output 804 of the amplifier circuit, in some embodiments, is a differential analog output signal that is coupled to a second housing 806 that encapsulates a mixed-signal circuit board that includes the analog-to-digital conversion circuit 114. The cable 704 between the snap button housing 802 and the second housing 806 is about 4 feet long, in some embodiments, and includes 4 conductors, including a first pair of twisted conductors for power and a second pair of twisted conductor to carry the analog output signal of the amplifier circuit. The second housing 806 may measure about 1 inch by 2.5 inch in dimensions, in some embodiments. The output of the second housing 806 is a second cable 808 that connects to a computing device. The second cable is about 2 feet long, in some embodiments, and includes 4 conductors including a power conductor, a ground conductor, and high speed digital conductors for the data lines. It should be appreciated that other dimensions of the various housing and lengths of the various cables may be used.

Example BioSignal Acquisition Circuit

Figure 9A:
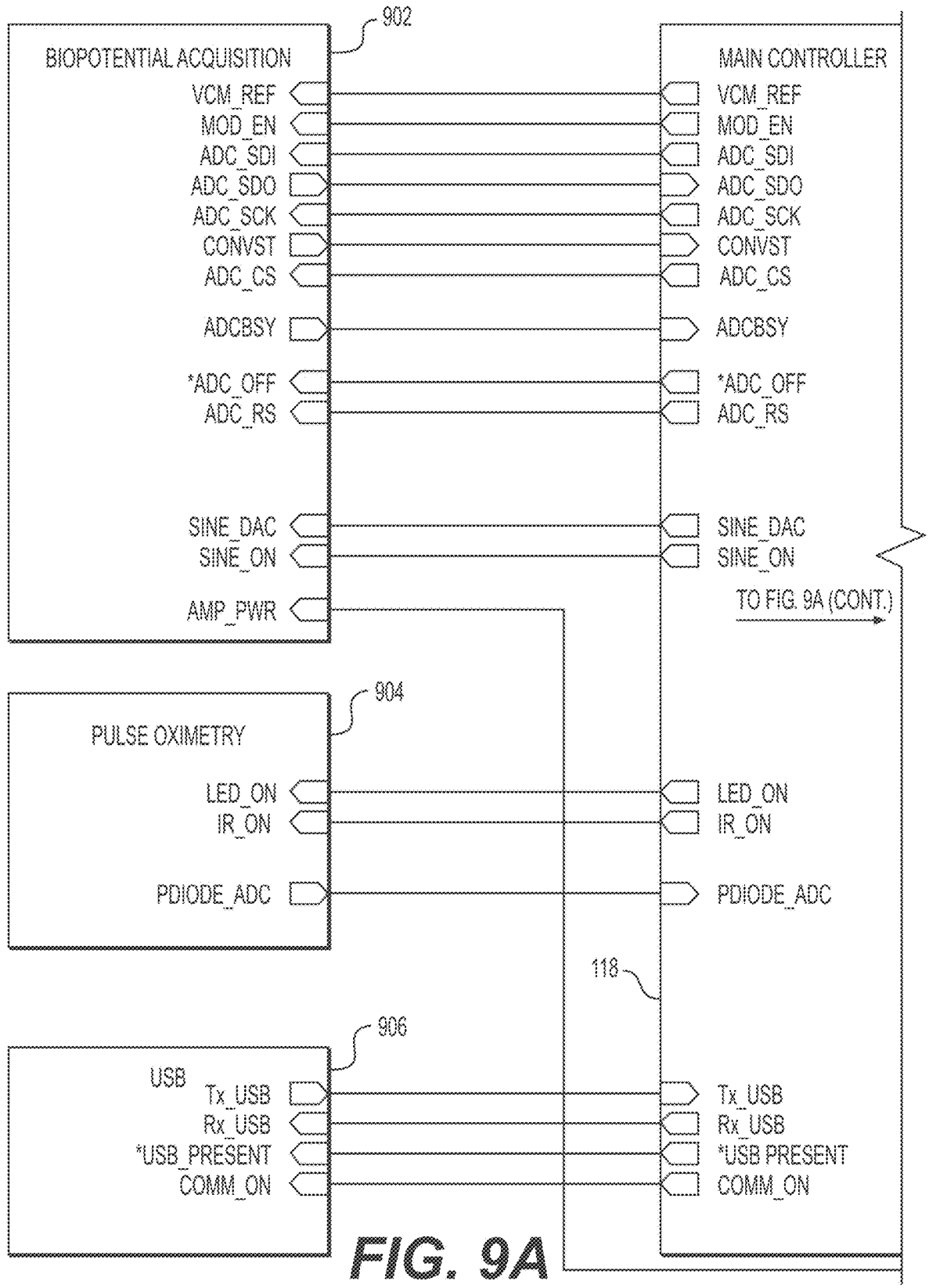
FIGS. 9A-9V, comprising
Figure 9A:
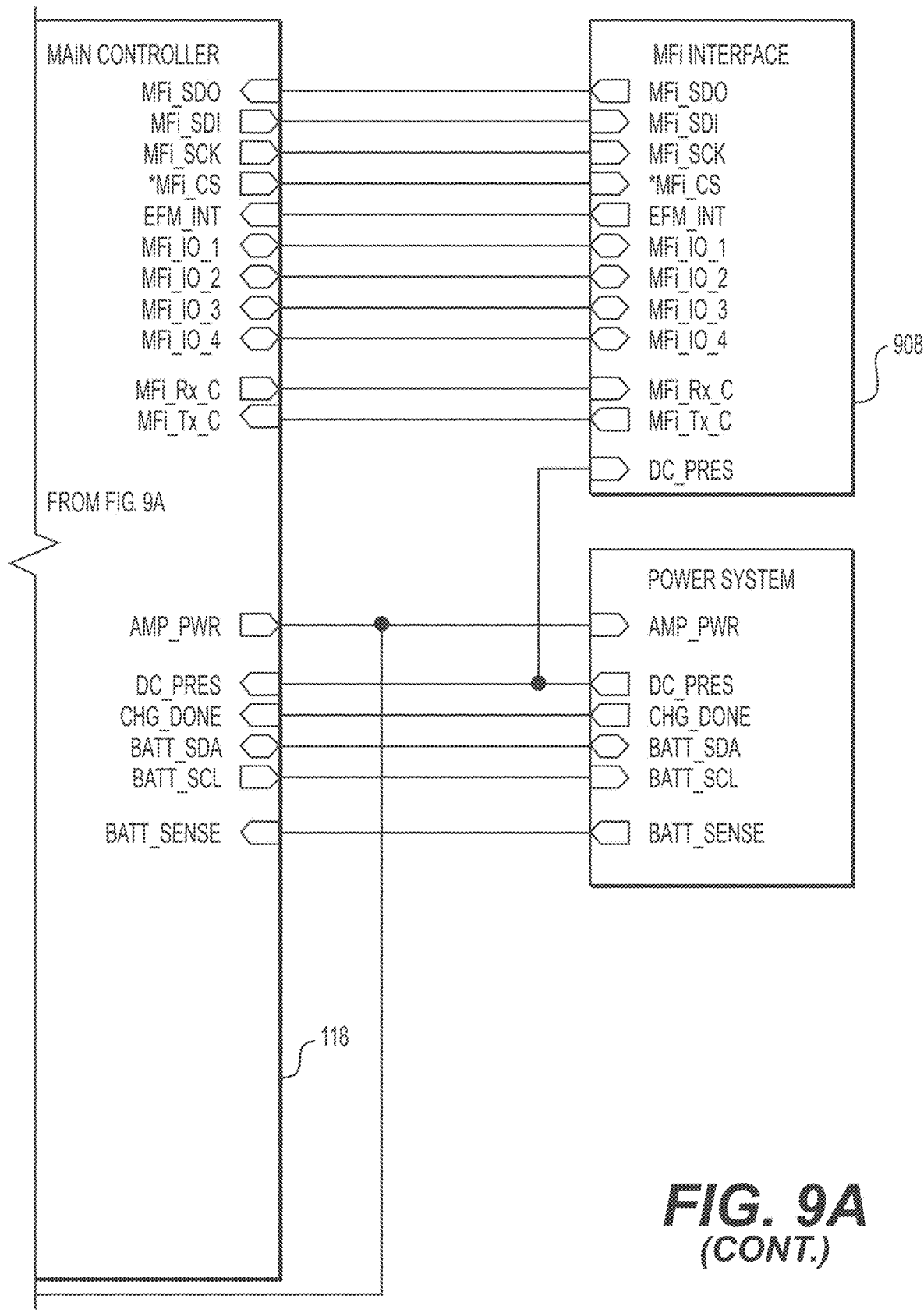
Figure 9B:
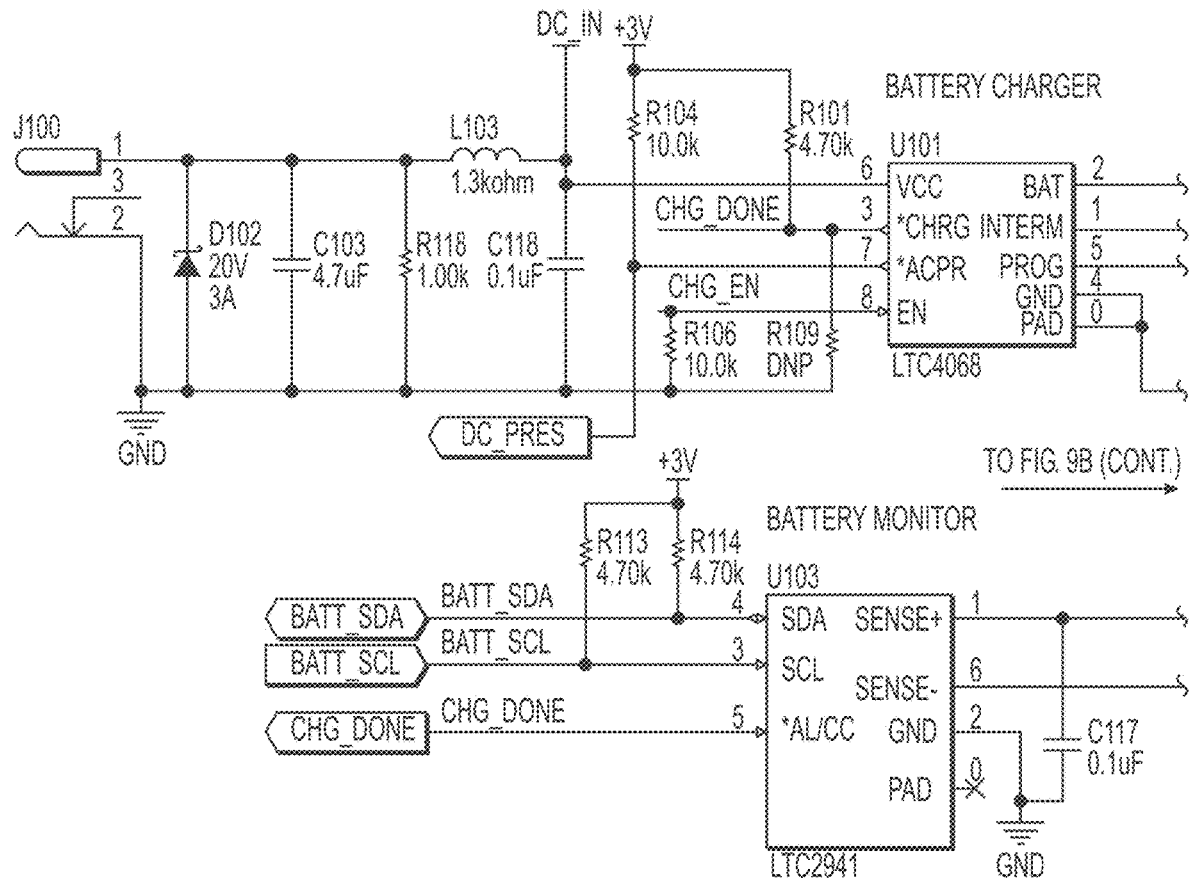
Figure 9B:
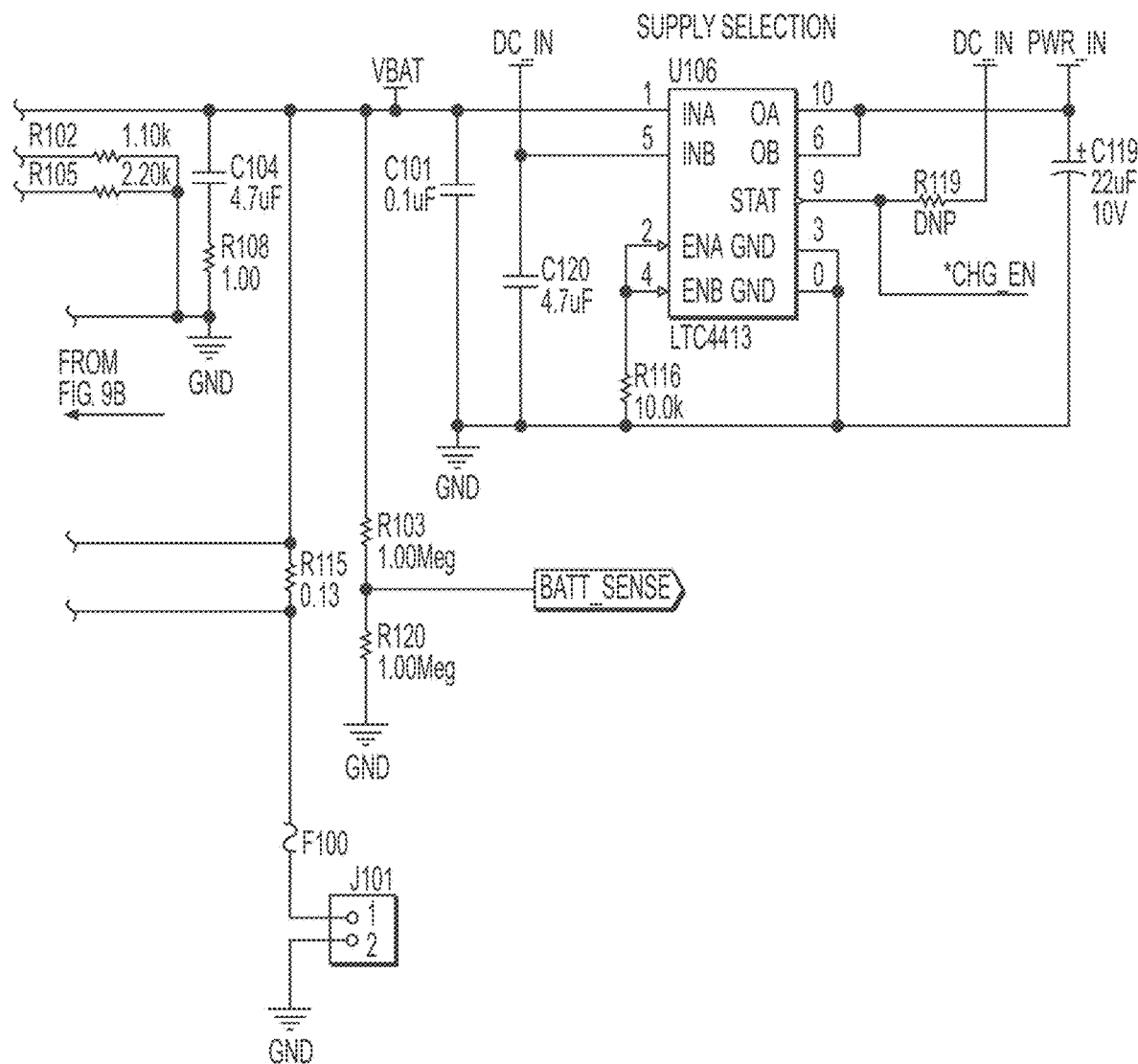
Figure 9C:
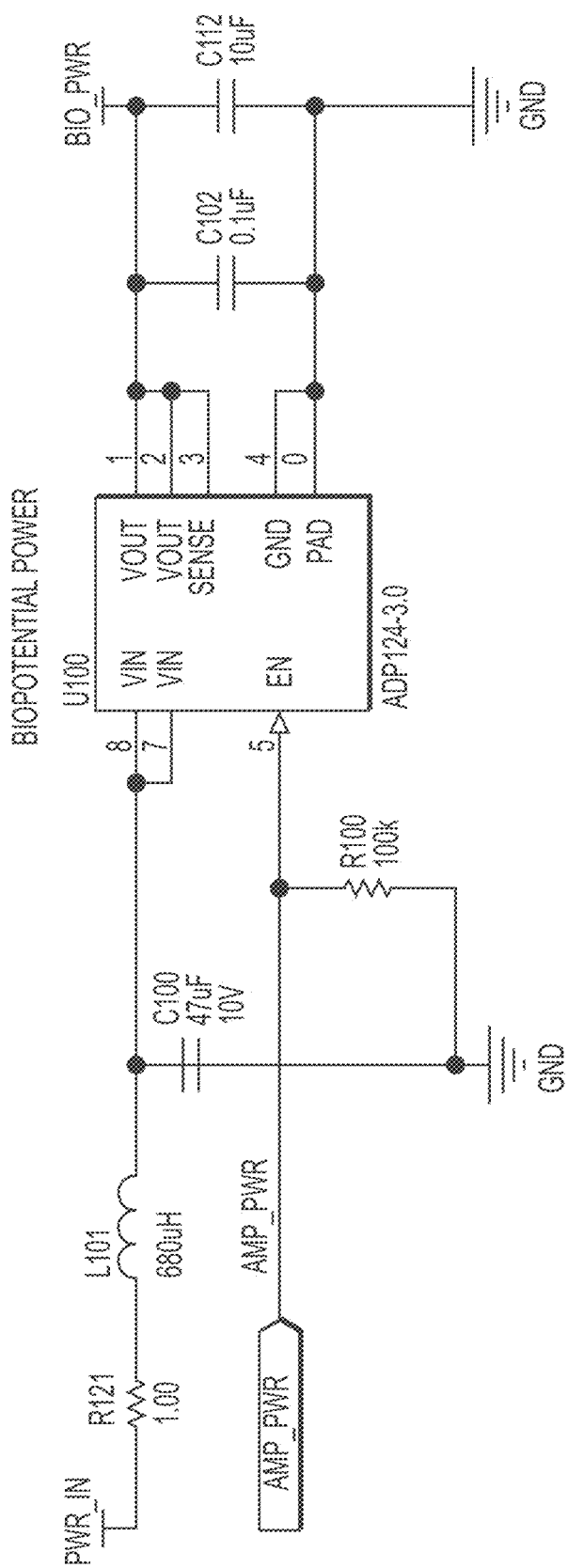
Figure 9D:
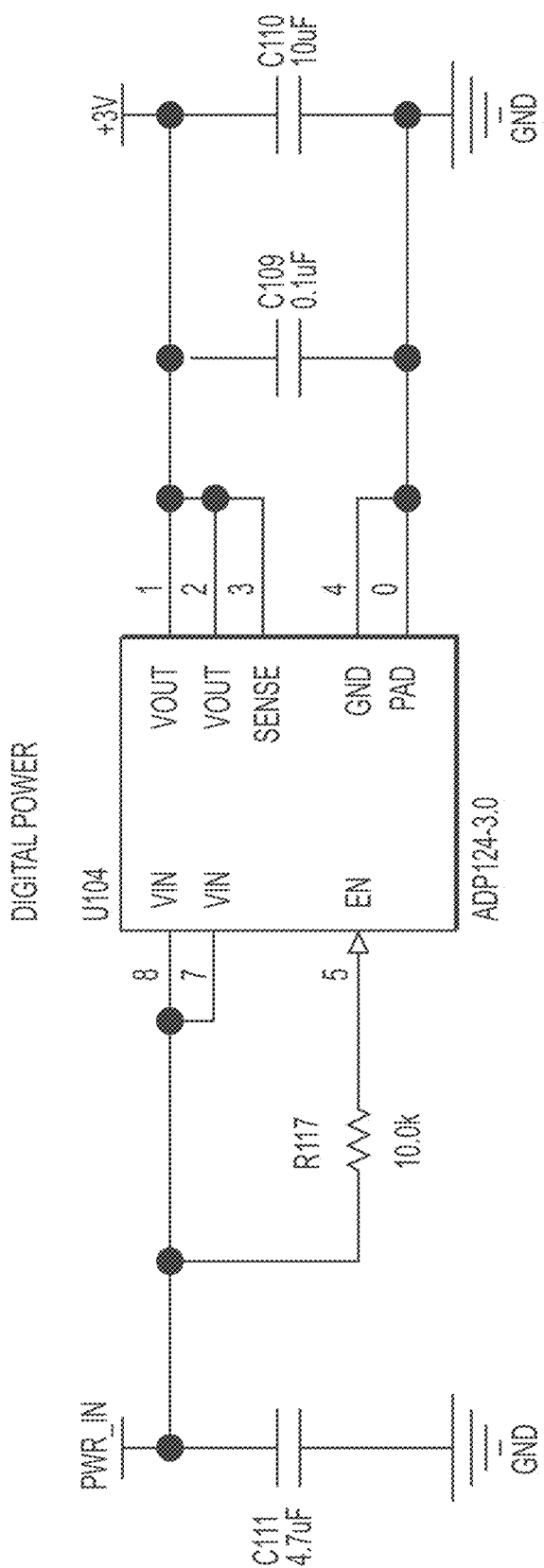
Figure 9E:
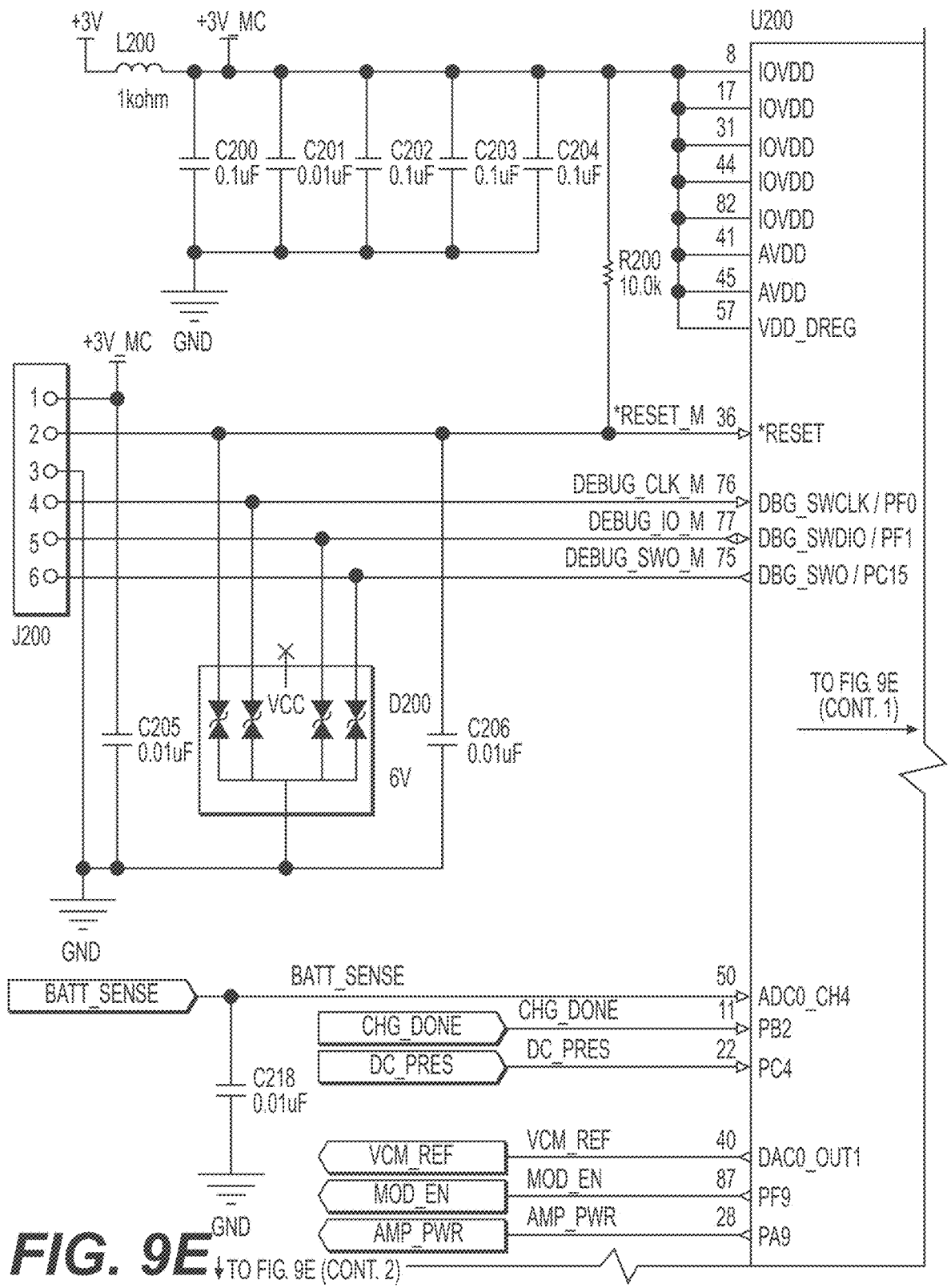
Figure 9E:
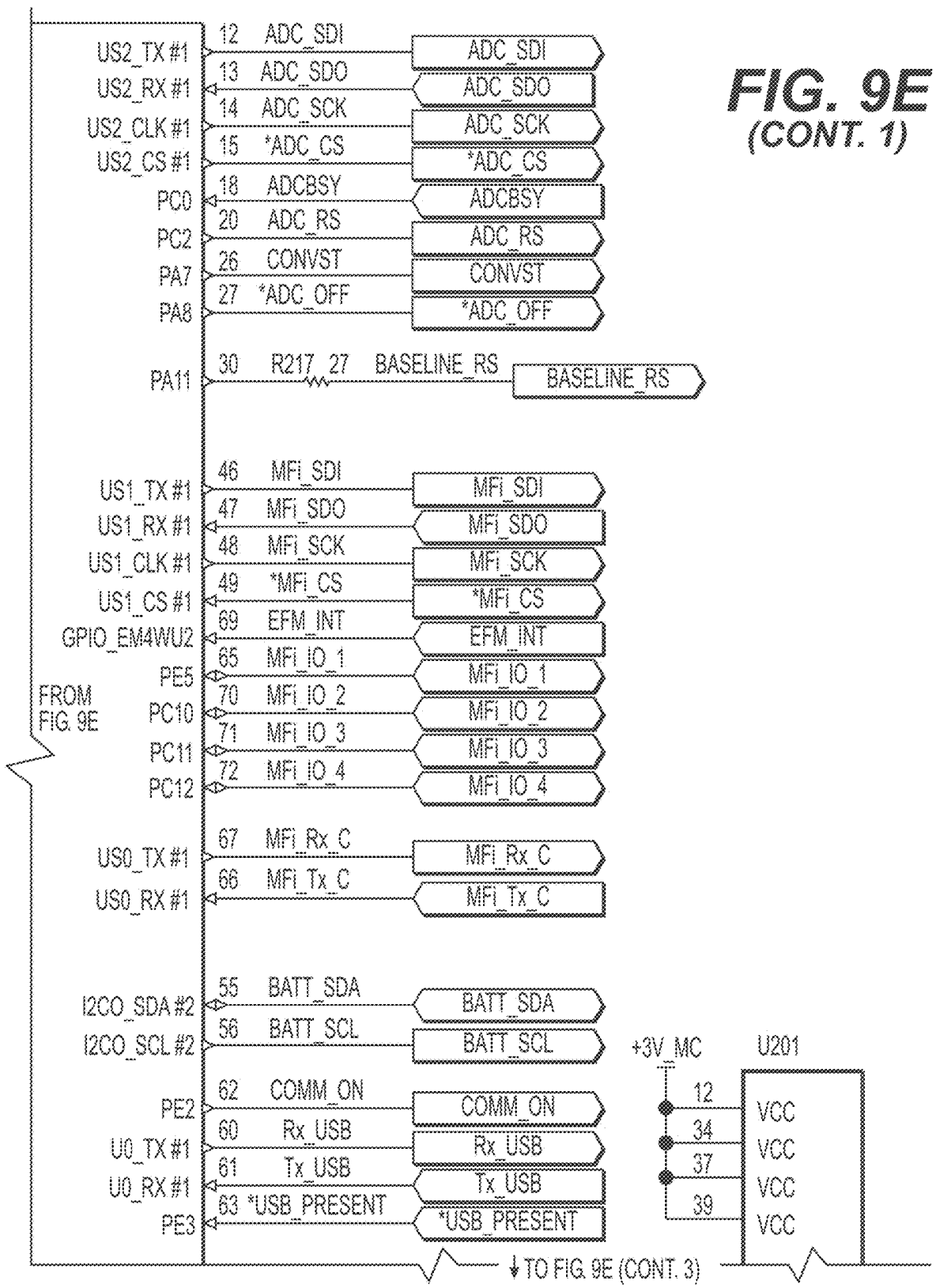
Figure 9E:
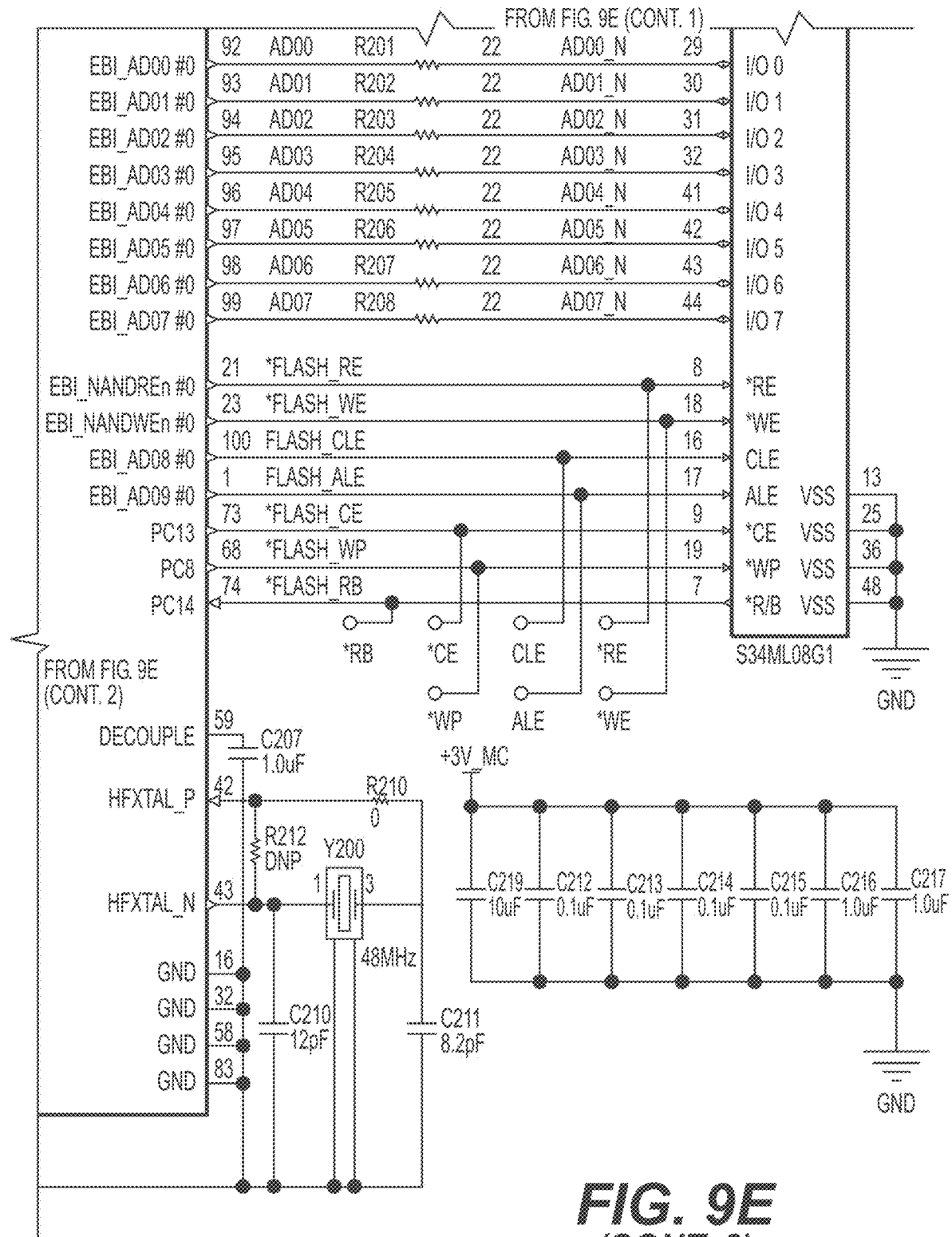
Figure 9F:
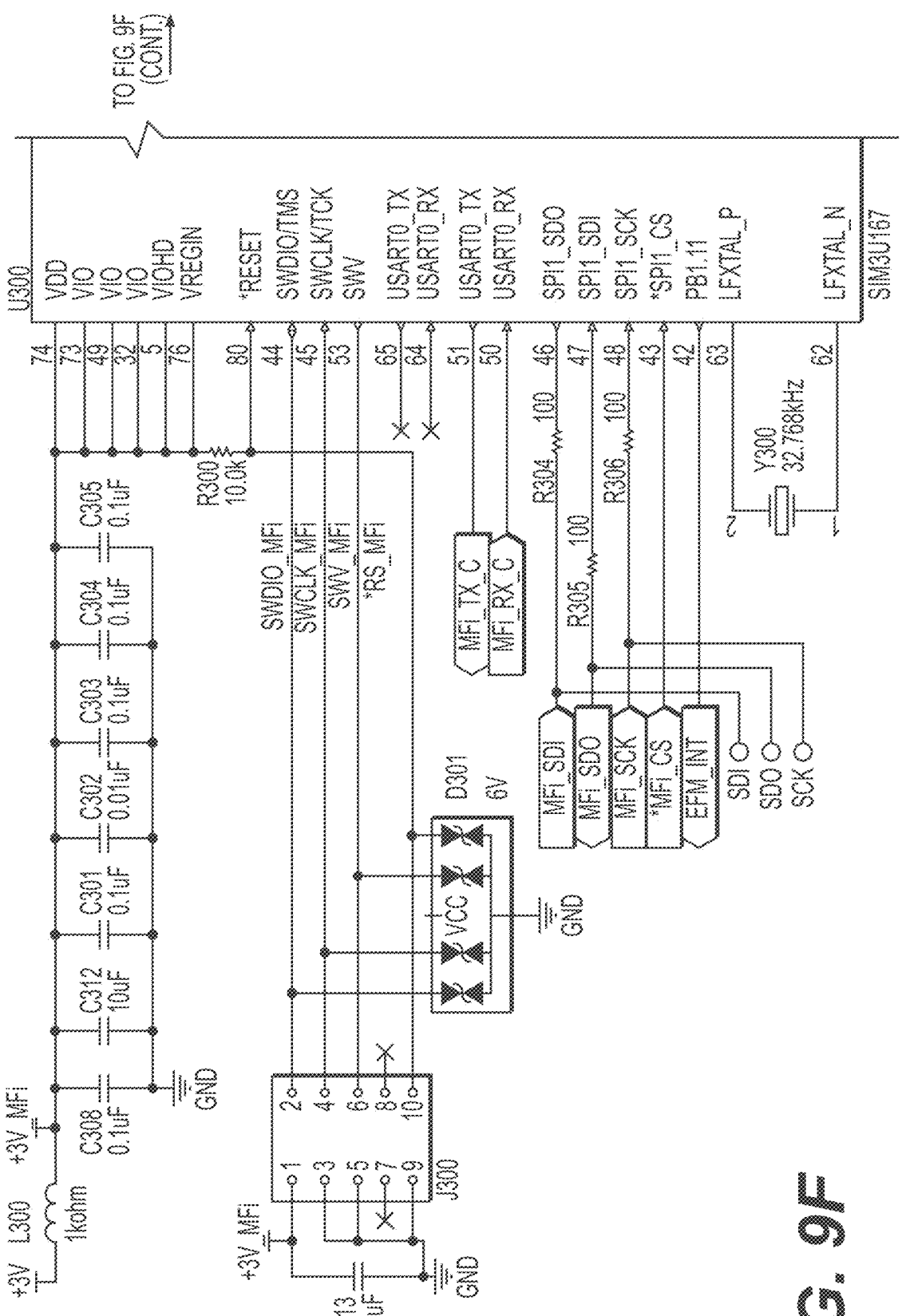
Figure 9F:
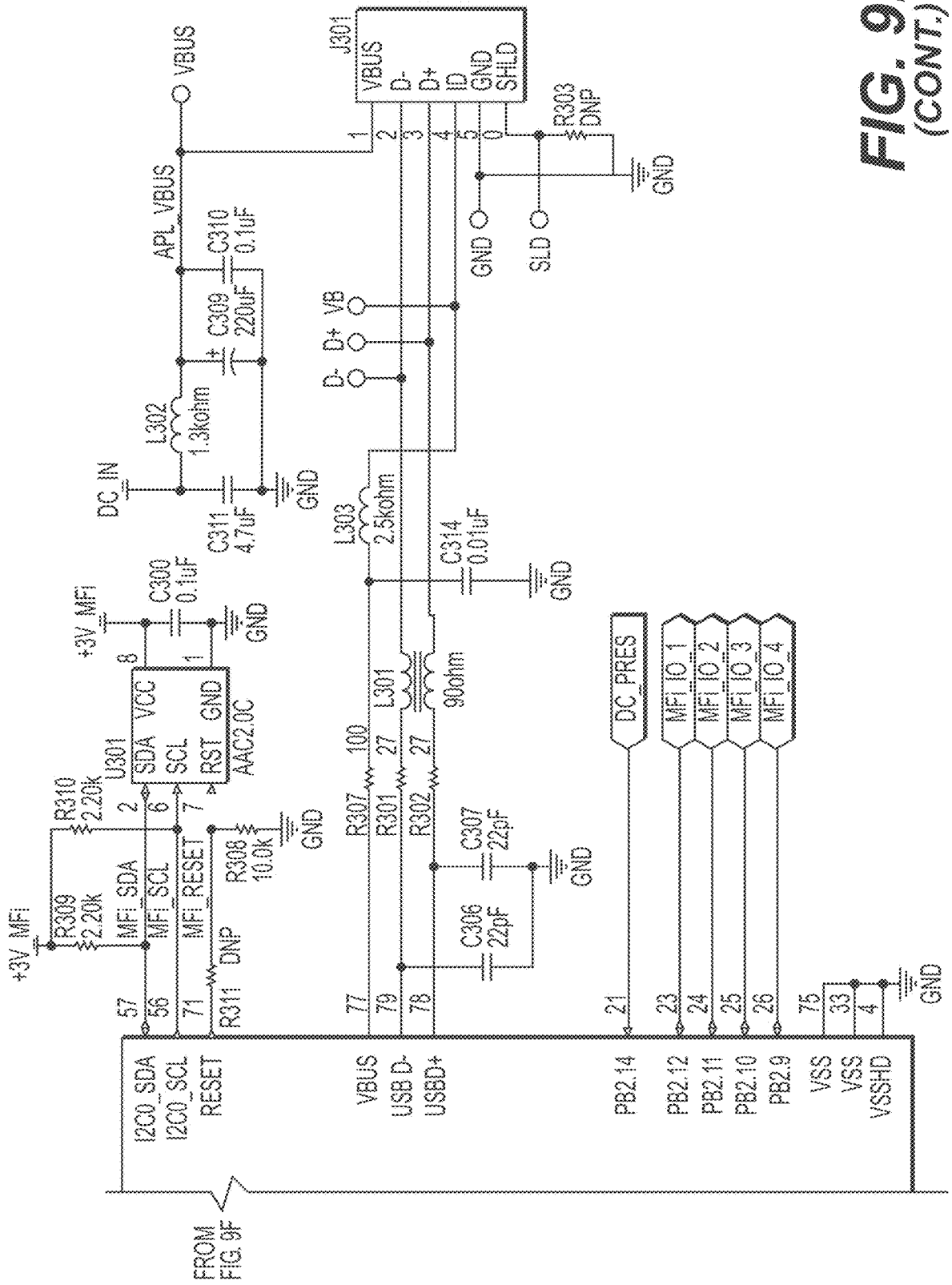
Figure 9G:
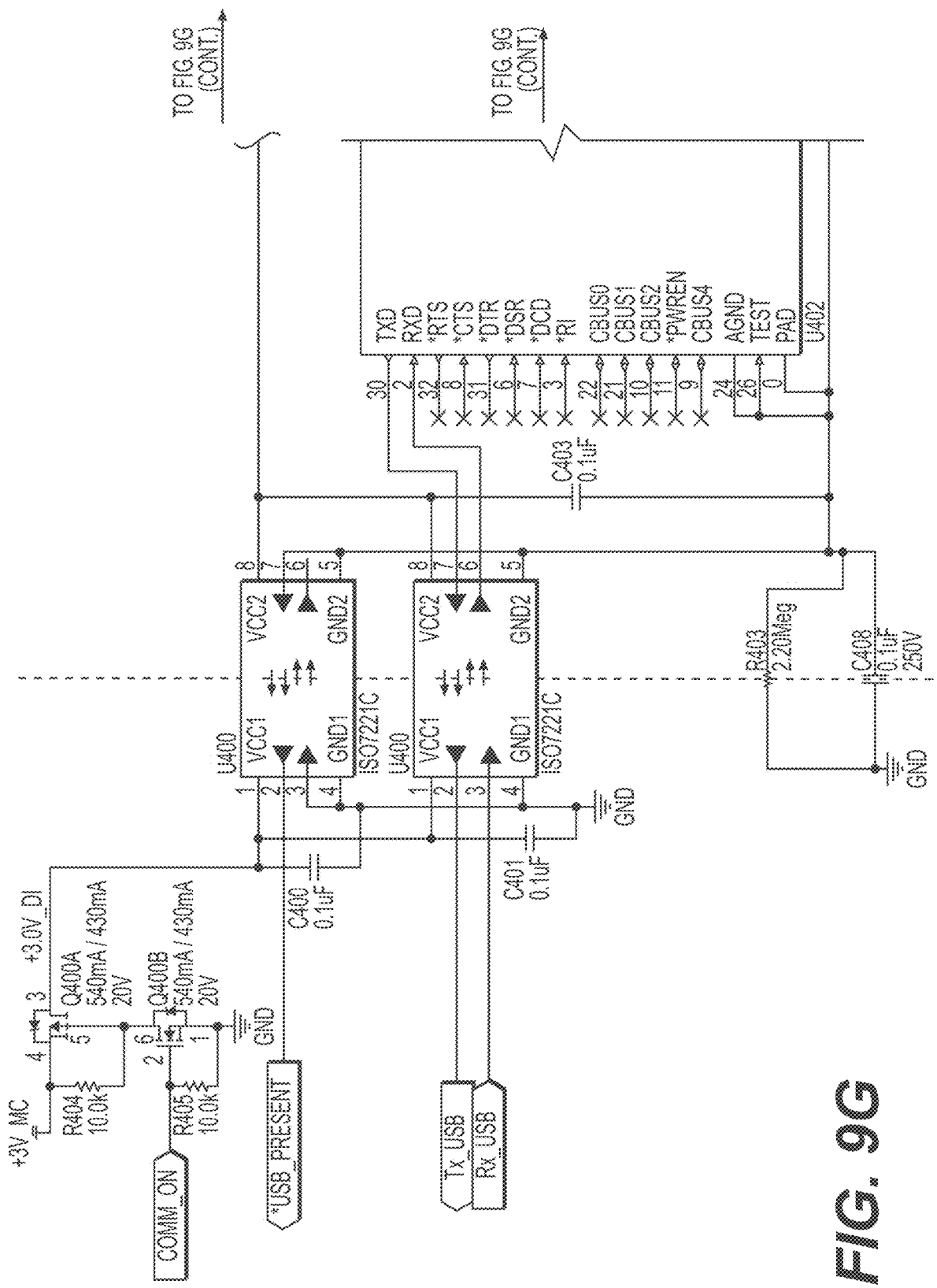
Figure 9G:
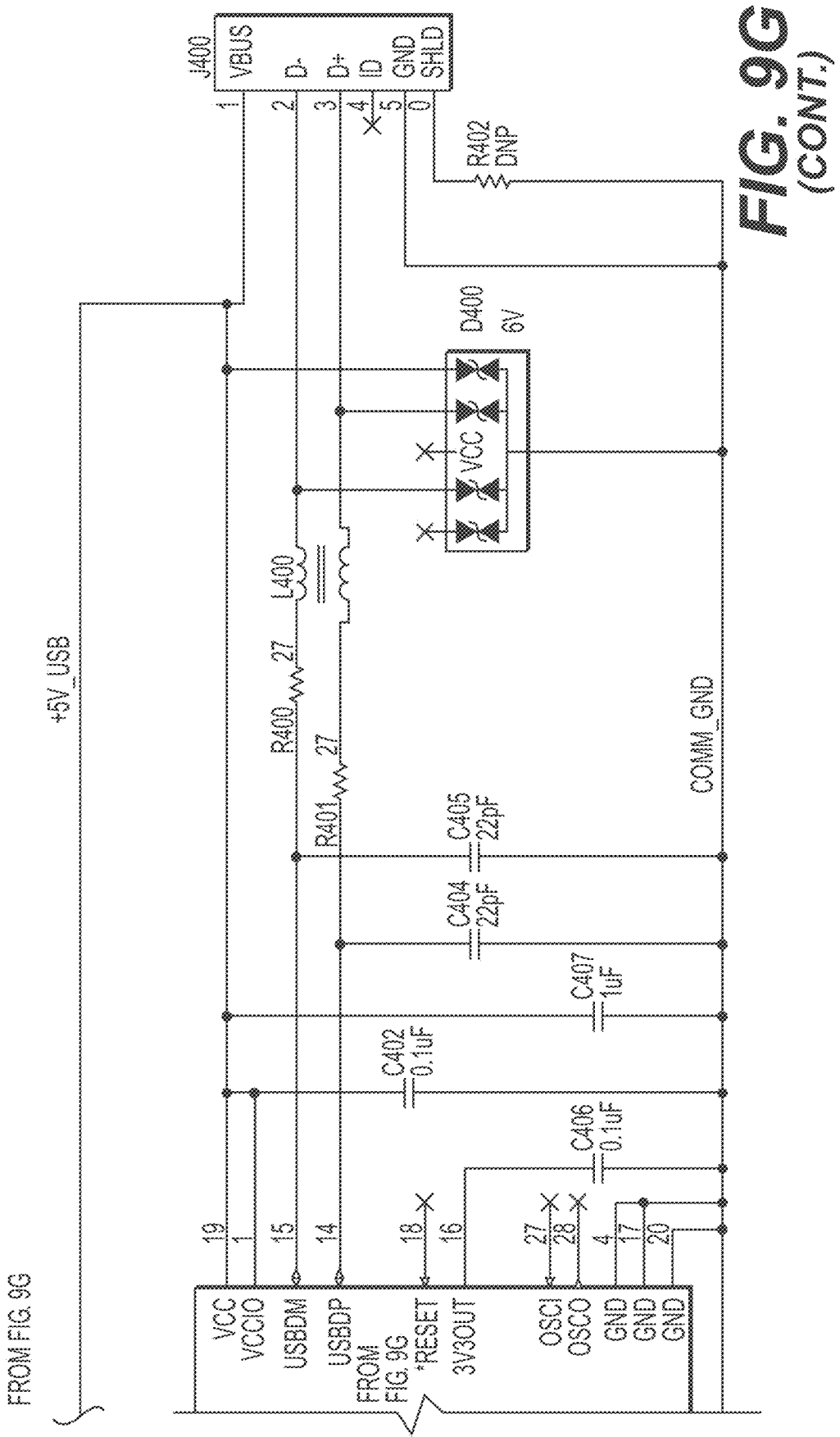
Figure 9H:
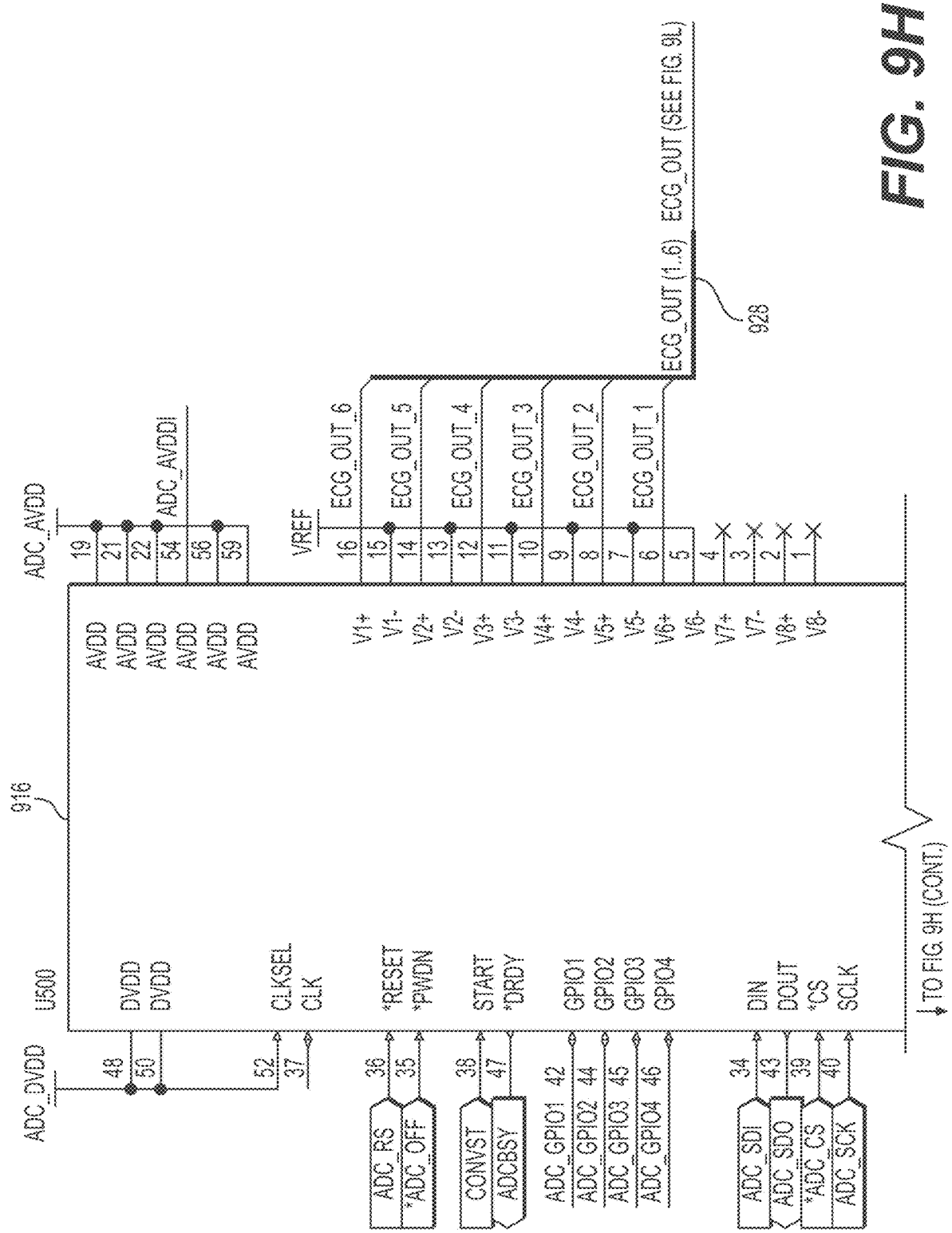
Figure 9H:
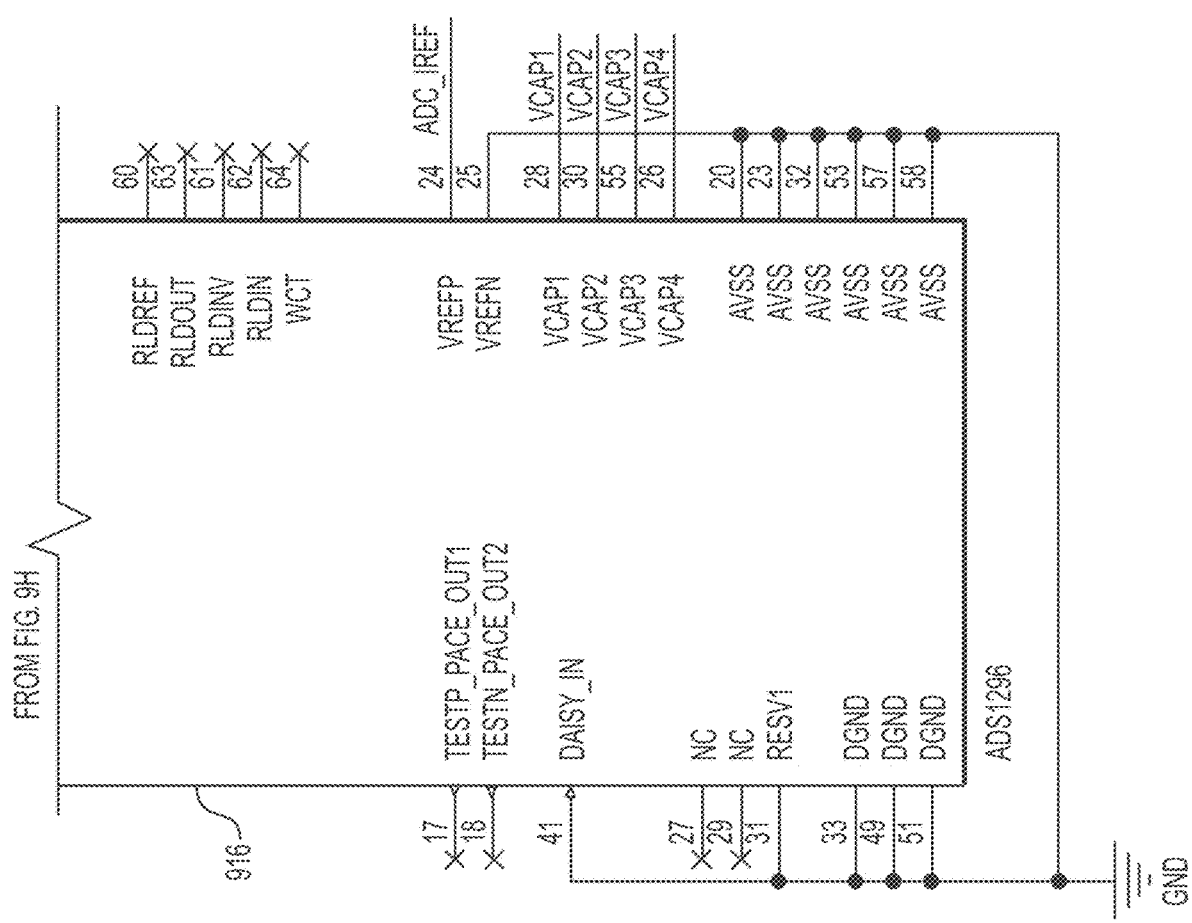
Figure 9L:
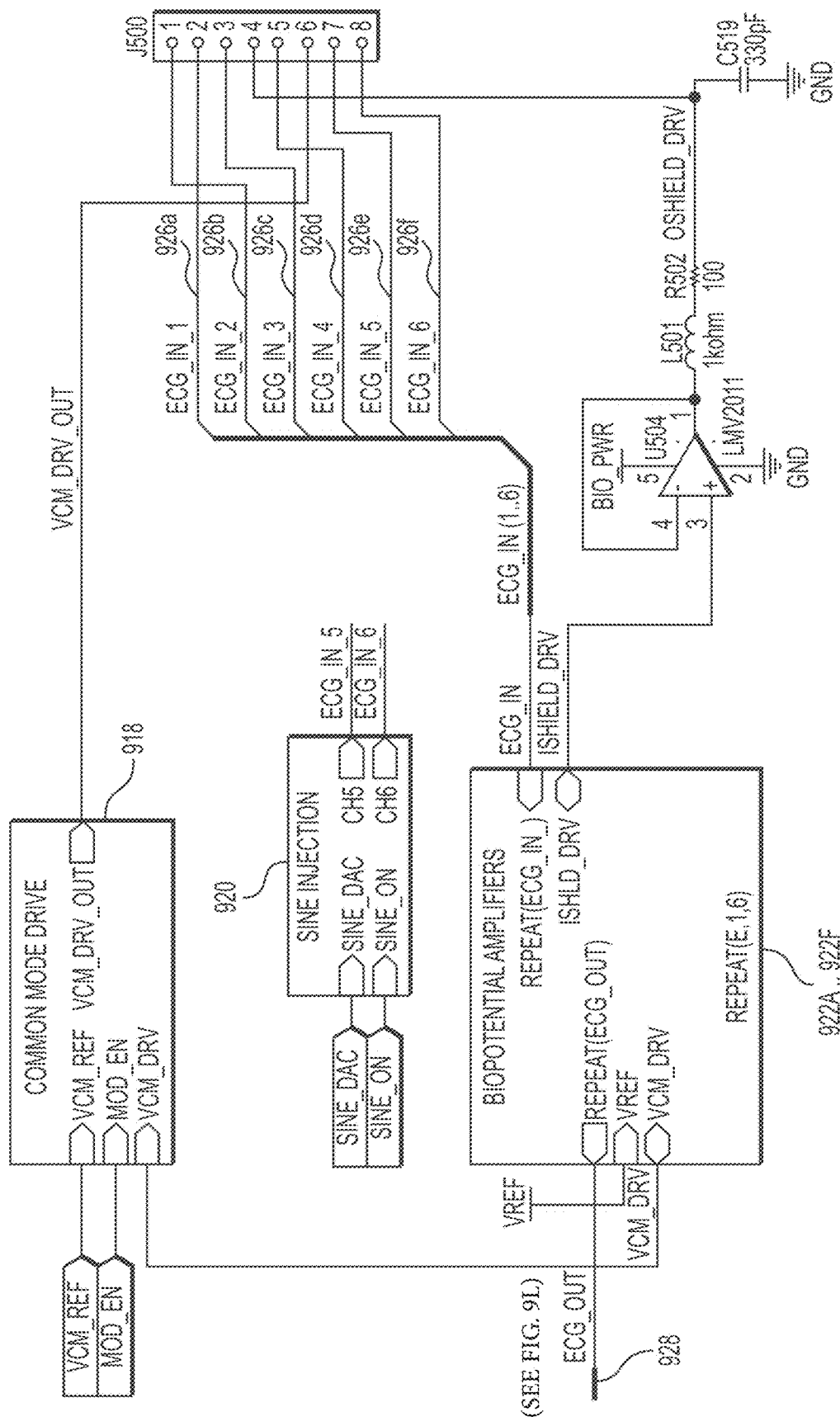
Figure 9M:
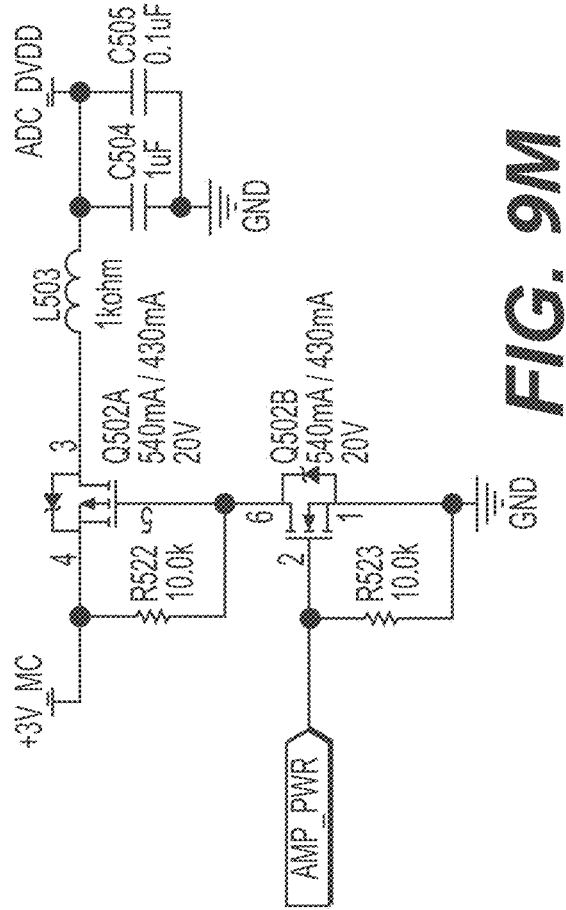
Figure 9N:
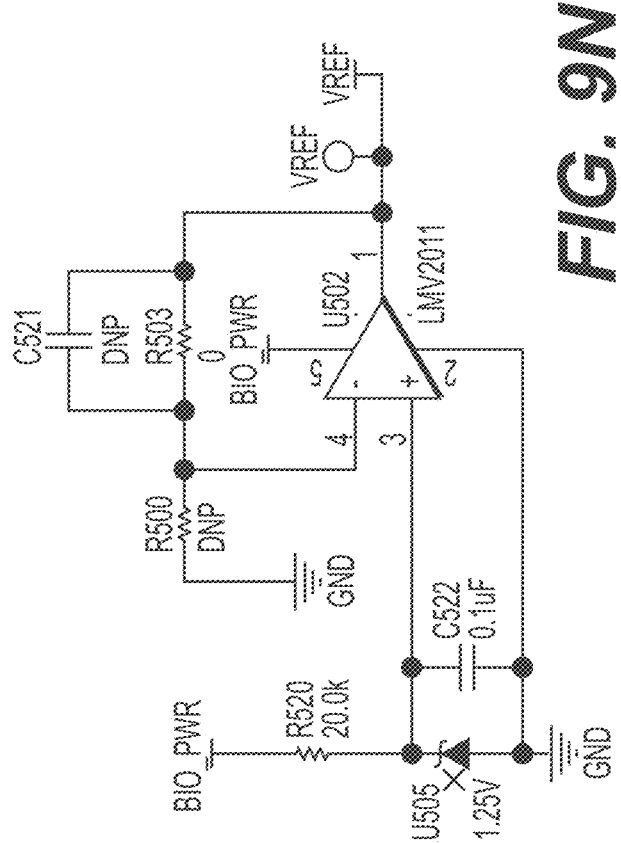
Figure 90:
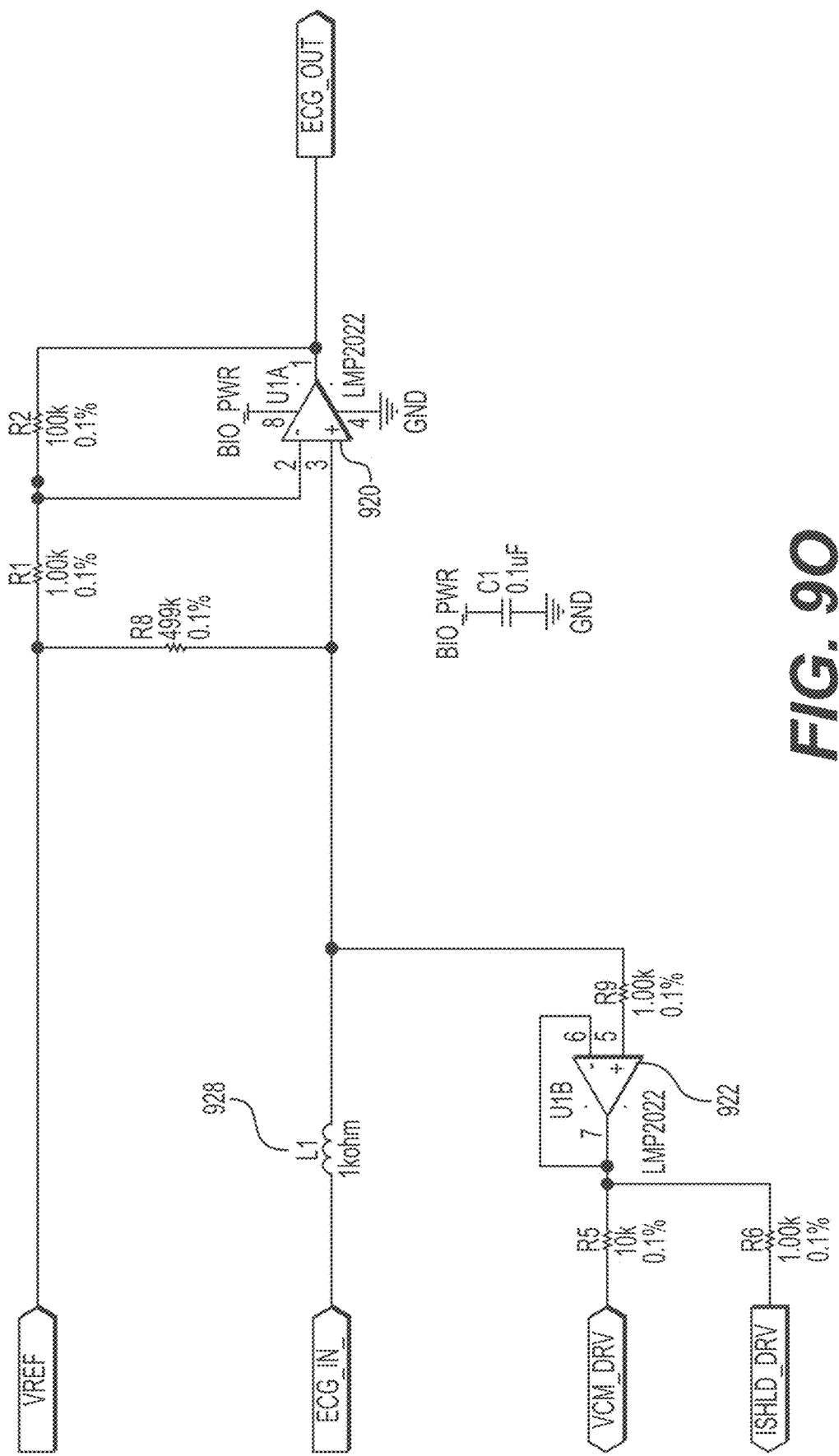
Figure 9P:
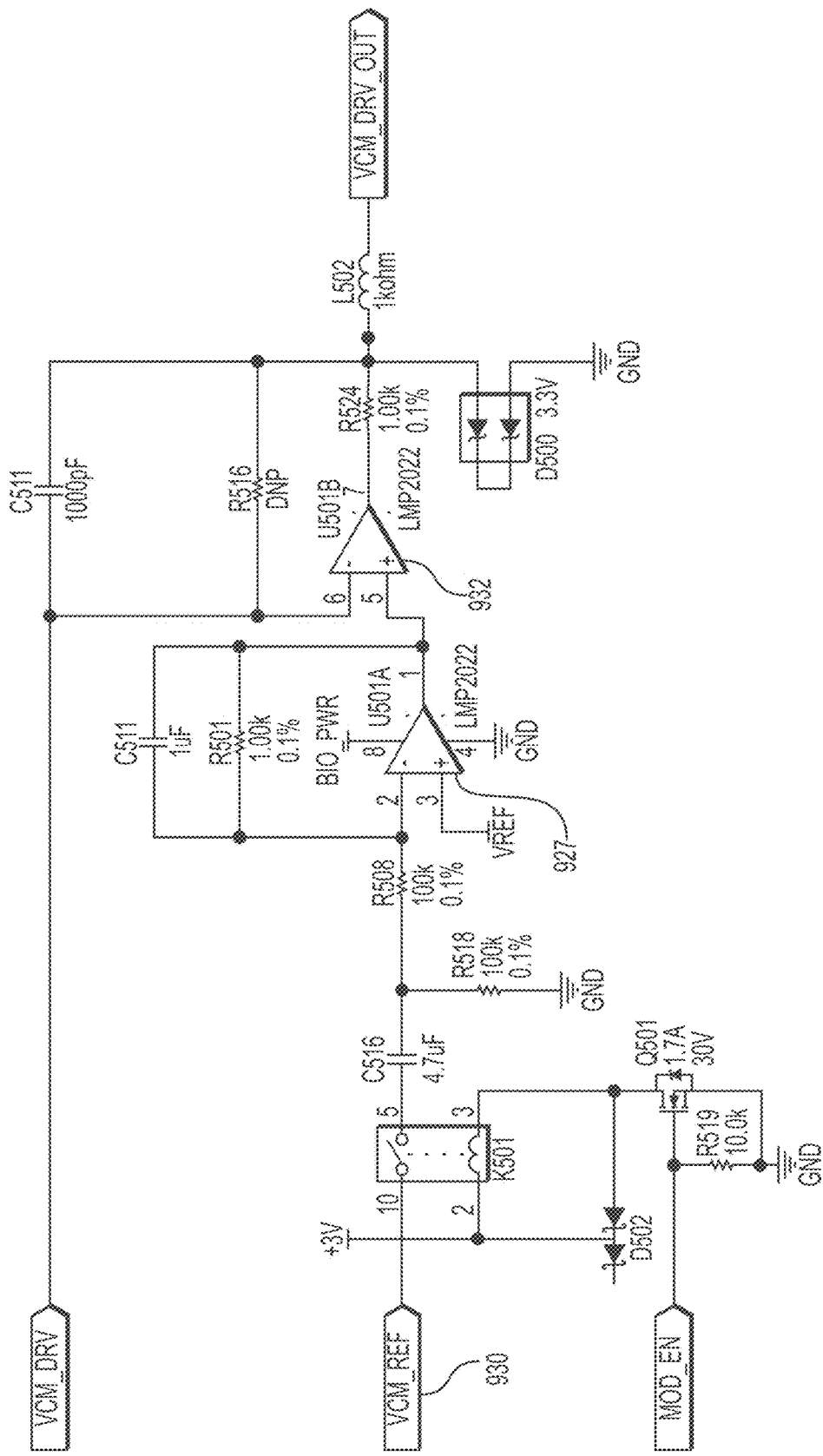
Figure 9Q:
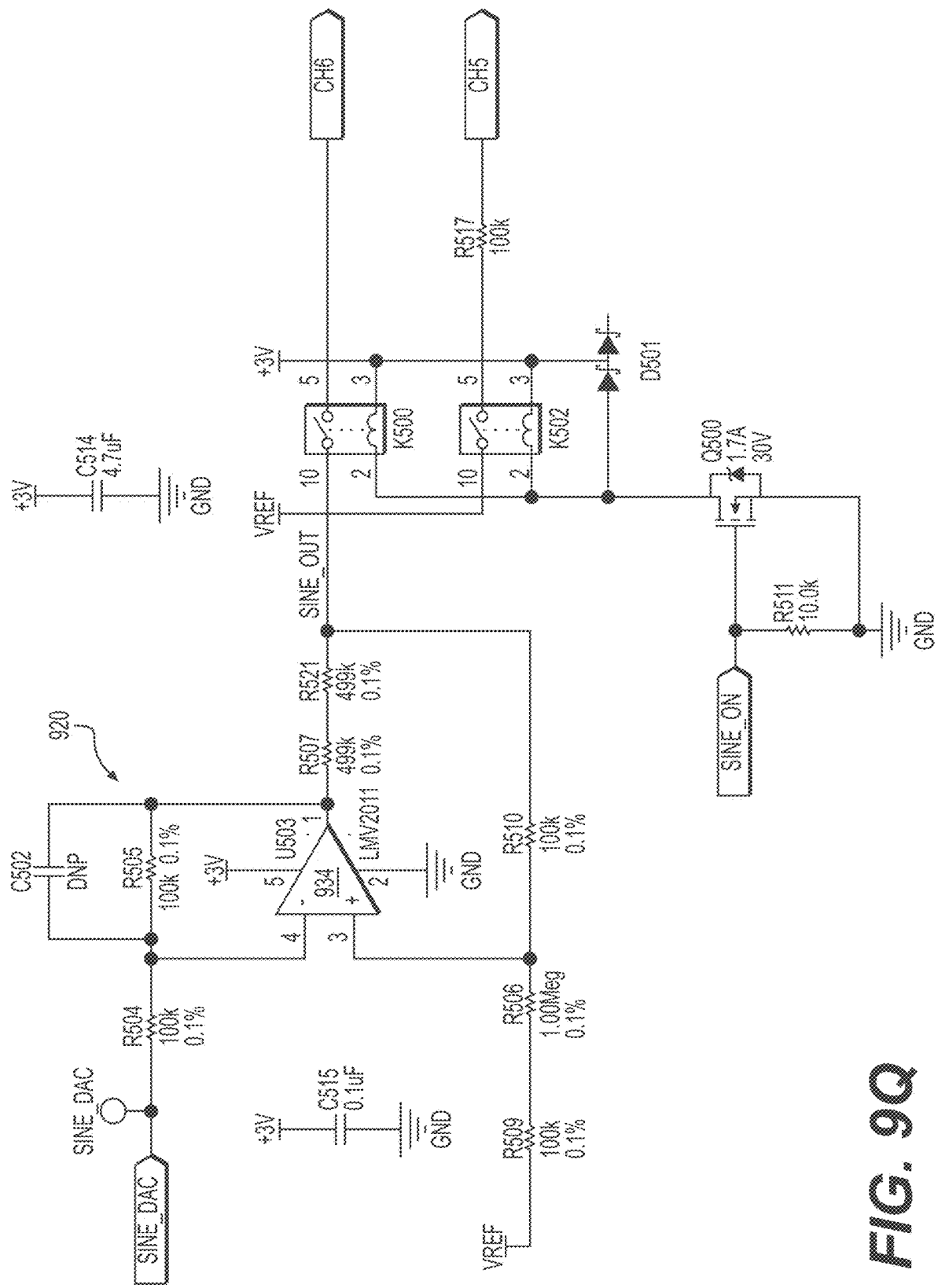
Figure 9R:
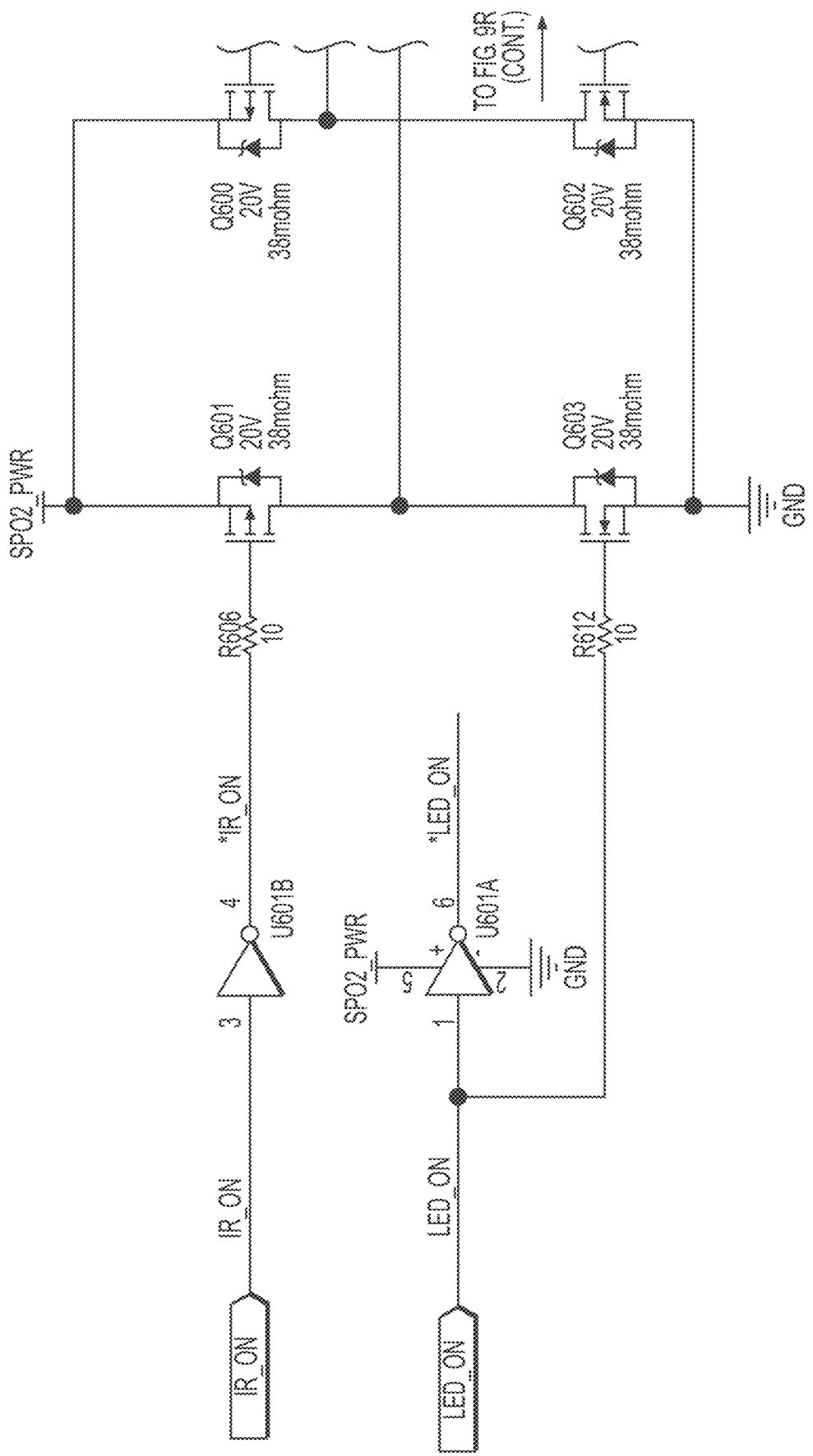
Figure 9R:
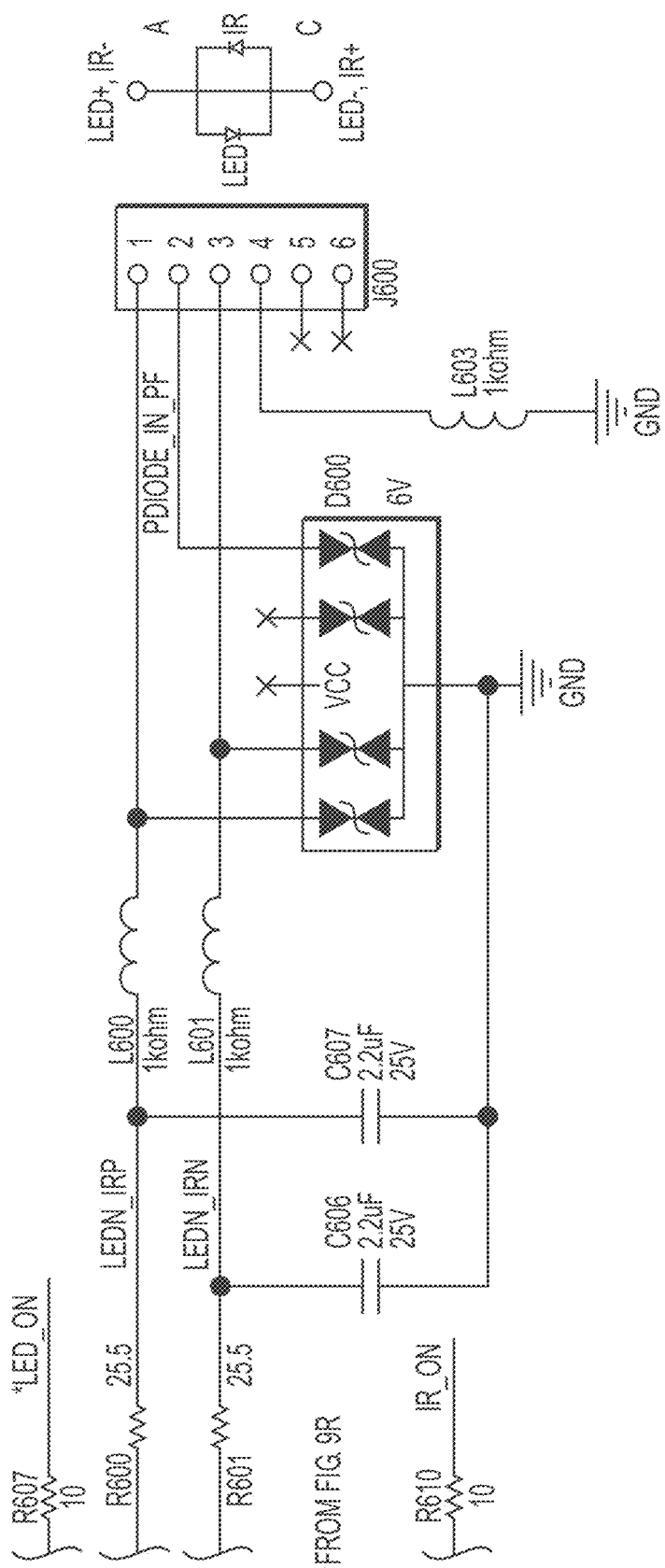
Figure 9S:
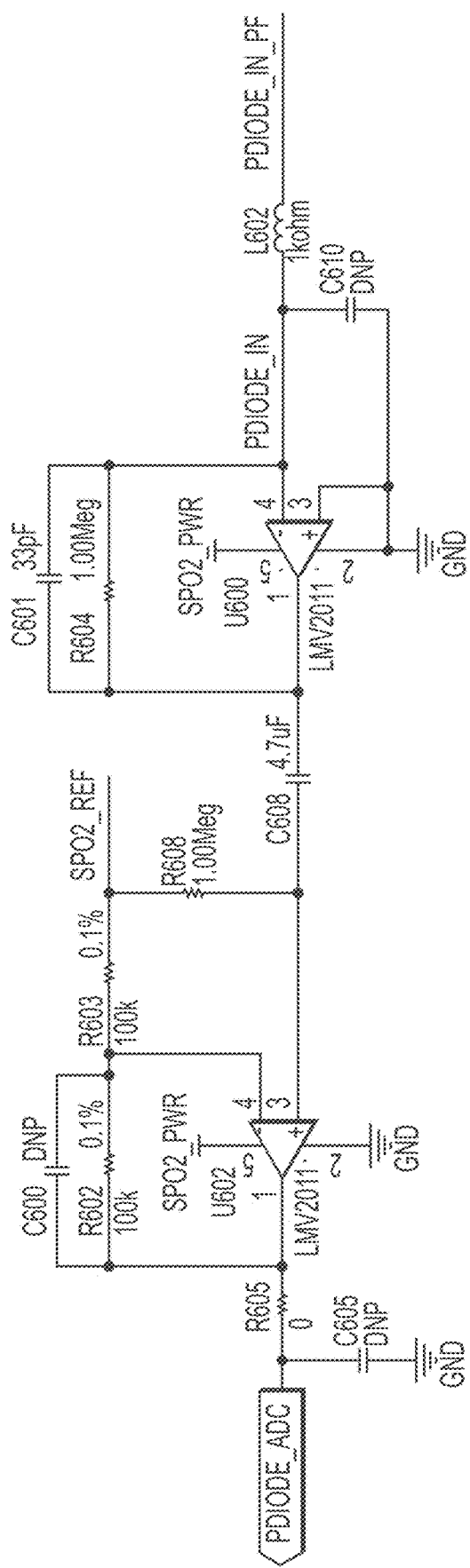
Figure 9T:
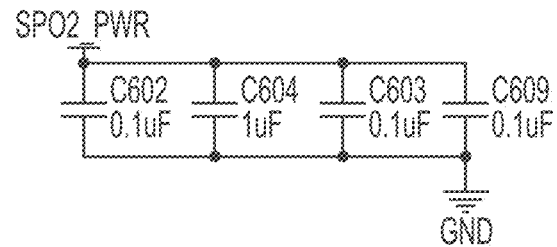
Figure 9U:
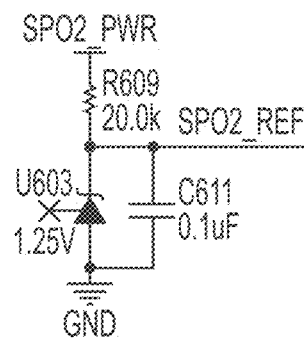
Figure 9V:
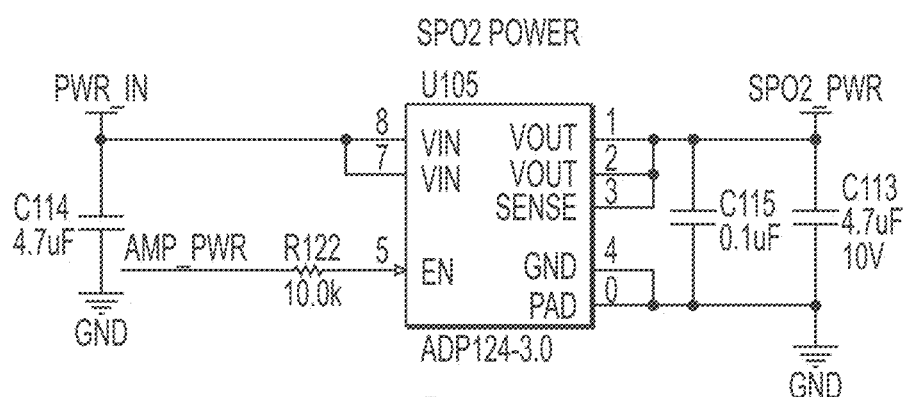

FIGS. 9A-9V, comprising FIGS. 9A, 9B, 9C, 9D, 9E, 9F, 9G, 9H, 9I, 9J, 9K, 9L, 9M, 9N, 9O, 9P, 9Q, 9R, 9S, 9T, 9U, and 9V, are circuit diagrams of a wide-band cardiac phase gradient signal acquisition system in accordance with an illustrative embodiment.

Specifically, FIG. 9A shows a high-level diagram of the system 100. As shown in FIG. 9, the system 100 includes a main controller 118 that couples to a biopotential acquisition circuit 902 that acquires the biopotential signal data associated with wide-band cardiac phase gradient signals and a pulse oximetry circuit 904 that acquires oximetry data. The system 100 further includes a USB interface circuit 906 configured to provide communication to the main controller 118 for testing and development and a MFi interface circuit 908 that provides connectivity to a computing device (e.g., device 606 as described in relation to FIG. 6). The system 100 further includes a power system to provide power to the various circuits and also to provide reference voltage for the analog-to-digital conversion.

FIGS. 9B, 9C, and 9D show detailed diagrams of power circuits. In FIG. 9B, a power circuit to supply power to the system 100 from batteries is shown. The power circuit includes a monitoring and charging circuit. In FIG. 9C, a power circuit for the biosignal acquisition channel is shown. In FIG. 9D, a power circuit for digital circuits is shown.

FIG. 9E shows a detailed diagram of a controller circuit corresponding to the microcontroller 118, the controller circuit include a microcontroller 910 (shown as device "EFM32GG880" 910) and a memory 912 (shown as device "S23ML0G1" 912). The microcontroller "EFM32GG880" is an ARM Cortex CPU platform manufactured by Silicon Labs (Austin, TX). The memory "S23ML0G1" is an 8 GB (gigabyte) NAND Flash memory manufactured by Cypress Semiconductor Corporation (San Jose, CA). The microcontroller operates with the biosignal acquisition channel to receive the biopotential signal data acquired thereat and to locally store the data to the NAND Flash memory for each acquisition.

FIG. 9F shows a detailed diagram of the MFi circuit 908 that includes a microcontroller 914 (shown as device "SiM3U167" 914) that provides an interface to an external computing device. The microcontroller 910 of FIG. 9E, between acquisition of one or more wide-band cardiac phase gradient signal data, retrieves the data (e.g., biosignal data and instrument identification data) stored in the NAND Flash memory and transfers the data to the external computing device through the MFi circuit 908.

FIG. 9G shows a detailed diagram of the USB communication circuit that is used to access the microcontroller 118 (e.g., for testing and development) and that is not available for access by a user during normal runtime operation.

FIGS. 9H, 9I, 9J, and 9K show detailed diagrams of an analog-to-digital conversion circuit that includes an analog-to-digital converter 916 with an integrated ECG front end circuit (shown as device "ADS1294" 916). Specifically, FIG. 9H shows the wiring of the analog-to-digital conversion circuit 916, via the control lines and data lines, with the microcontroller 118 and the biopotential amplifier circuit shown in FIG. 9L. FIGS. 9I, 9J, and 9K each shows the detailed diagram of the capacitive decoupling and filtering of the power plane and ground plane of the analog-to-digital conversion circuit. In some embodiments, the analog-to-digital converter comprises an 8-channel, simultaneous sampling, 24-bit, delta-sigma ($\Delta\Sigma$) analog-to-digital converters (ADCs) with built-in programmable gain amplifiers (PGAs), internal reference, and an onboard oscillator. Other configuration of the analog-to-digital conversion circuit may be used, though the analog-to-digital conversion circuit has at least about 17 bits of resolution, preferably about 24 bits.

FIGS. 9L, 9M, and 9N show a detailed diagram of a biopotential acquisition circuit. In FIG. 9L, a noise reduction circuit 918 (shown as "Common Mode Drive 918") that provides a common-mode reference to the body, a sine injection circuit 920 (shown as "Sine Injection 920") used for impedance measurement, and a biopotential amplifier circuit 922 (shown as "biopotential amplifiers" 922a to 922f) used to acquire the wide-band cardiac phase gradient signals are shown. The biopotential amplifier circuit 922 is coupled to a terminal 924 (shown as "J500 924") that connects to pins of the cable 124.

As shown in FIG. 9L, an active noise reduction system that actively shields the signal-carrying conductor in the cable 124 is used in which the shield of the cable is driven to a potential that is an average of the biopotential signal (shown as "ECG_IN_1" 926a, "ECG_IN_2" 926b, "ECG_IN_3" 926c, "ECG_IN_4" 926d, "ECG_IN_5" 926e, and "ECG_IN_6" 926f) received at each biopotential amplifier circuit 922. As shown and discussed in relation to FIGS. 4 and 5, a shield-equalizing circuit may be used that includes an operational amplifier that injects the signal carried in the conductor (e.g., biopotential signals 926) to individual shields of the cable such that the injected signal approximately matches (e.g., within at least about 90%) the signal carried in the cable.

FIG. 9M and FIG. 9N show detailed diagrams of power conditioning circuits that provide reference voltages to the biopotential amplifier circuits as shown in FIG. 9L and to the biopotential amplifier circuit as shown in FIG. 9H.

FIG. 9O shows a detailed diagram of an example biosignal acquisition channel 922, as shown in connection with FIG. 9L, used to acquire the biopotential signals associated with the wide-band cardiac phase gradient signal. As shown in FIG. 9O, the example BSA instrument acquires measurements from each of the, for example, six, biopotential electrodes on the patient. Each of these voltages is measured relative to a +1.5 VDC reference—the same voltage to which the patient's body is driven by the common mode amplifier during normal operation. An operational amplifiers U1A (shown as "LMP2022" 920) and U1B (shown as "MPL2022" 922) are powered by a single +3 VDC supply. In some embodiments, a single negative −3 VDC supply is used to provide a negative DC common mode output.

As discussed herein, the reference common mode potential can be drive between +1.5 VDC and −1.5 VDC, in some embodiments. When driving the body to a negative voltage (e.g., −0.5 VDC), it is possible to maximize the gain of the input stage and to prevent the DC bias from railing the operational amplifiers into a clipping condition. The gain and the dynamic range of the signal can be expanded when the negative voltage exceeds the DC half-cell potential generated by the surface electrode (e.g., silver chloride electrode). In some embodiments, the DC half-cell potential is about 300 mV.

As shown in FIGS. 9L and 9O, the operational amplifiers U1A 920 (FIG. 9O) directly couples to the terminal 924 (FIG. 9L). To this end, there is a lack of active and passive filters and/or circuit elements that can introduce non-linear distortions and noise into the signal path. A ferrite choke 928 (e.g., ferrite bead) is placed in the signal path to suppress high frequency noise (e.g., radio-frequency noise). It is noted that radio-frequency signals are generally in the MHz range which is several orders of magnitude higher than the biopotential signals of interest, which are in the KHz to hundreds of KHz. At the frequency of interest, the ferrite choke 928 has an impedance of about 1 kΩ.

Referring still to FIG. 9O, amplifier U1A 920, along with resistors R2 and R1, provides a gain of 101. Thus a 1 mV (millivolt) peak-to-peak signal on the non-inverting input of U1A 920 translates to 101 mV peak-to-peak at the output of the amplifier 920. It should be appreciated that other gains can be utilized that provides at least about 15 dB. In some embodiments, the gain is greater than about 20 dB.

Referring to FIG. 9L, the outputs 928 of all six biopotential amplifiers feed a six-channel, simultaneous sampling ADC (as shown in relation to FIG. 9H). The use of a simultaneous sampling ADC minimizes the temporal skew between the biopotential channels. As shown in FIG. 9L, the ADC circuit 916 samples with a resolution of at least about 17 bits (e.g., about 24 bits) over an input range of about 0 V to about 5V. When combined with the input amplifier gain of 101, this provides an overall measurement resolution of about 0.38 uV. The ADC circuit is configured to oversample at eight times the base sampling frequency, or about 8 kSPS, and to average, in computation, the results to provide additional filtering. In some embodiments, the ADC circuit 916 includes internal anti-aliasing filter, e.g., at about 2.7 kHz that prevents aliasing at the full sampling rate of about 8 kSPS, in the absence of external filtering. In other embodiments, the anti-aliasing filter is implemented via processing of the time series data during the analysis of the acquired biopotential signals.

Noise Reduction Circuit

FIG. 9P shows a detailed diagram of an example noise rejection circuit that provides a common-mode reference to the body.

The goal of the noise rejection system is to eliminate environmental noise currents flowing in the patient's body that might interfere with biopotential measurement. Noise may be generated from a variety of environmental sources; including consumer electronics, cell phones, and the local AC power system. Any or all of these may generate voltages at the measurement electrodes that will render a patient's biopotential un-measurable or more difficult to measure.

To combat environmental noise, the BSA Instrument hardware employs a common mode amplifier—operational amplifier, U501B (shown as "LMP2022" 924)—to actively drive the patient's body to a varying potential (e.g., between −1.0 VDC and −2.0 VDC or +1.0 and +2.0 VDC) or a constant potential (e.g., a value between +1.5 VDC or −1.5 VDC) and thus shunt environmental noise currents during normal operation. The inverting terminal of U501A (shown as "LMP2022" 926) receives an analog signal, e.g., from the microcontroller 118 as shown in FIG. 9A, that provides a reference potential (shown as "VCM_REF 930"), and U501B (shown as "LMP2022 932") works make this average match the VCM_REF voltage applied to its non-inverting terminal. Capacitor C500 limits the gain of the amplifier at high frequencies, thus stabilizing its operation.

During normal operation, VCM_REF 930 is, e.g., set to a constant positive +1.5 VDC or negative −1.5 VDC by the BSA Instrument microcontroller 118. However, this voltage can be modulated by the microcontroller in order to provide additional information regarding lead connectivity. Changes in VCM_REF will appear directly on the individual channel amplifier outputs if the reference lead and the channel leads are connected to the patient.

Sine Injection Circuit

FIG. 9Q shows a detailed diagram of an example sine injection circuit 920 (as also shown in relation to FIG. 9L) used for impedance measurement. As shown in FIG. 9Q, the sine injection circuit 920 includes a transconductance amplifier circuit (shown as "U503 934") used to inject current into a patient for thoracic impedance measurement. In some embodiments, the transconductance amplifier circuit includes an operational amplifier that injects a programmable current into a Z-axis of the patient which in turn induces a voltage on the other four biopotential electrodes that can be used to derive a multi-axis impedance computation for the patient's body. In some embodiments, the microcontroller 118 is configured to generate a current waveform that is offset by the reference voltage (V_Ref) generated by the noise reduction circuit.

As shown in FIG. 9Q, resistor R507 sets the transconductance gain of the amplifier to 1 uA/V (micro-Amp per Volt), and resistors R504, R505, and R509 complete the feedback network. Capacitor C502 is available, in some embodiments, for high frequency filtering. Relay K500 is employed to connect the current injection circuit to the patient only when it is to be used, when the microcontroller sets the SINE_ON signal to positive +3V. In some embodiments, the sine injection circuit 920 generates a frequency between about 1 kHz and about 3 kHz and have a maximum amplitude of about 100 μA. The sine injection circuit, in some embodiments, is configured to generate a waveform for a duration of at least about 5 seconds. Other waveform and frequency may be used to determine thoracic impedance.

FIG. 9R-9V, comprising FIGS. 9R, 9S, 9T, 9U, and 9V, are detailed diagrams of the oximetry circuit. The oximetry circuit is configured to operate with a pulse oximeter (PO2) sensor to collect oxygen saturation readings. In some embodiments, the oxygen saturation readings is collected with at least 12 bits of resolution and at a minimum rate of 200 samples per second.

Defibrillation Protection

Referring back to FIG. 9P, the noise reduction circuit of the example BSA instrument is designed to sustain the application of external defibrillation to the patient. As shown in FIG. 9P, in the common mode amplifier circuit, resistor R524 works with Zener diode, D500, to prevent U501B from sustaining damage during external defibrillation.

In some embodiments, in the individual channel amplifiers (e.g. FIG. 9O), the defibrillation protection circuit includes a fast air gap relay that adds little, or no, distortions to the connected signal path and that can survive multiple defibrillator shocks with little, or no, device degradation. In some embodiments, a combined defibrillation, surge, and ESD protector circuit is used. An example combined defibrillation, surge, and ESD protector circuit is the MAX30031 protection devices, manufactured by Maxim Integrated (San Jose, CA).

Example BSA Board

FIG. 10 is a photograph of an example biosignal acquisition ("BSA") board 1000 that includes the wide-band cardiac phase gradient signal acquisition system of FIG. 9 in accordance with an embodiment. As shown in FIG. 10, the BSA board 1000 comprises a conductive shield 1002 that surrounds the mixed-signal circuitries of the biosignal acquisition channel and the analog-to-digital conversion circuits. The inputs and outputs of the BSA board 1000 are combined in a connector 1004 to the cable 124 that connects to the surface electrodes. The BSA board 1000 is connected to a battery 1006 that provides power to the acquisition circuit. The BSA board 1000 includes a USB connector 1008 that provides an interface to the microcontroller 118.

Figure 11:
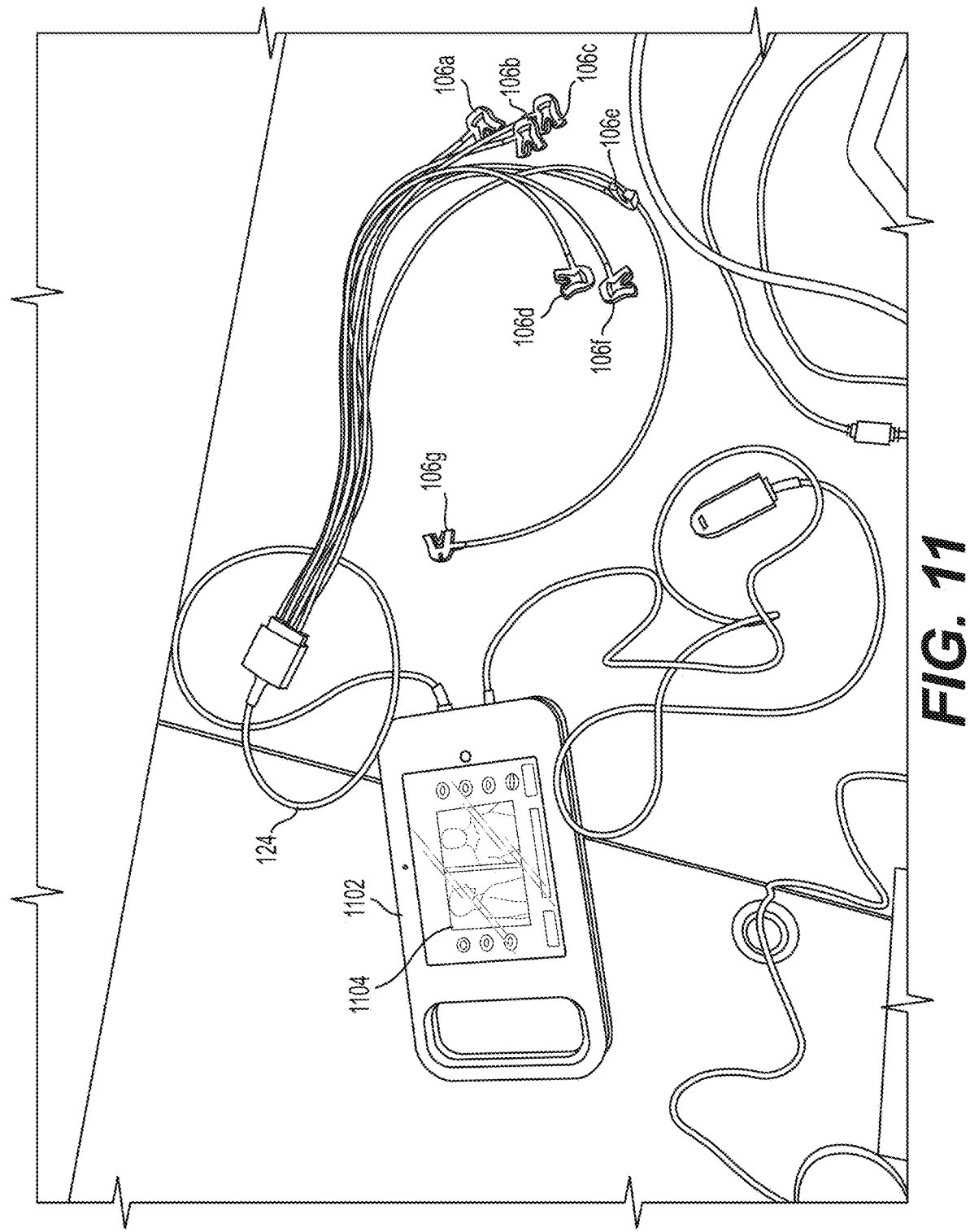
FIG. 11 is a photograph of an example BSA instrument that includes the BSA board of FIG. 10 in accordance with an embodiment.
Figure 12A:
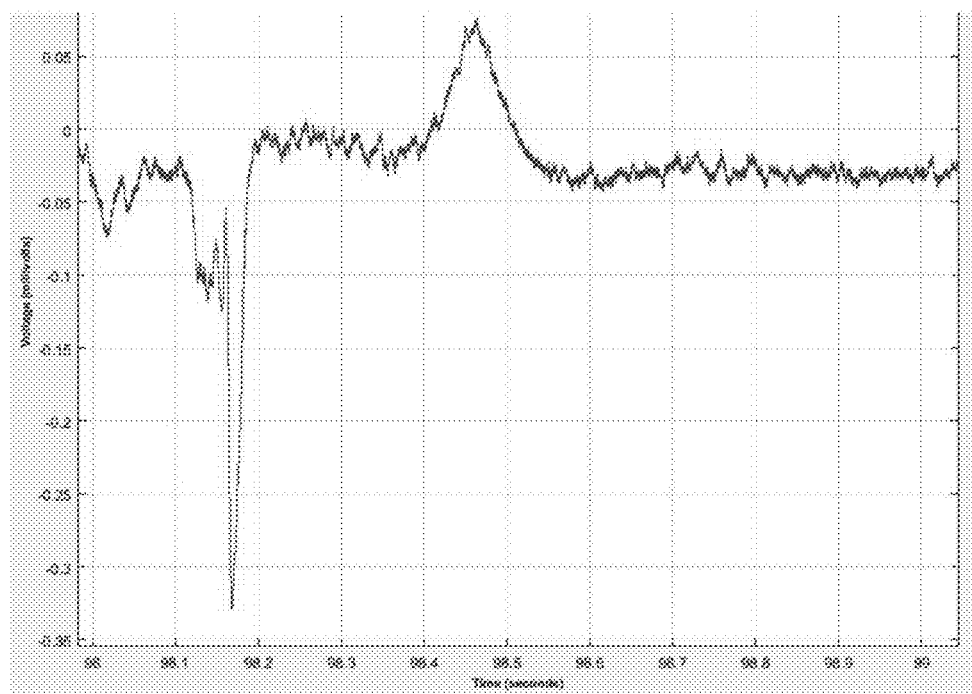
FIGS. 12A, 12B, 12C, 12D, 12E, and 12F, are example biopotential signal data acquired via the example BSA instrument as shown and described in relation to FIG. 10.
Figure 12B:
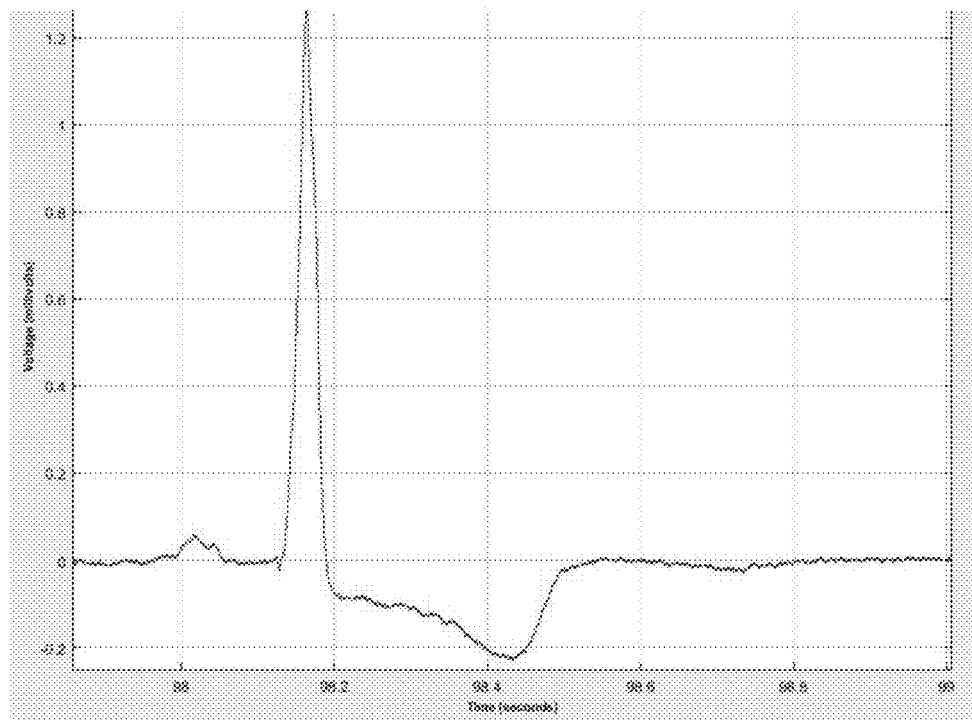
Figure 12C:
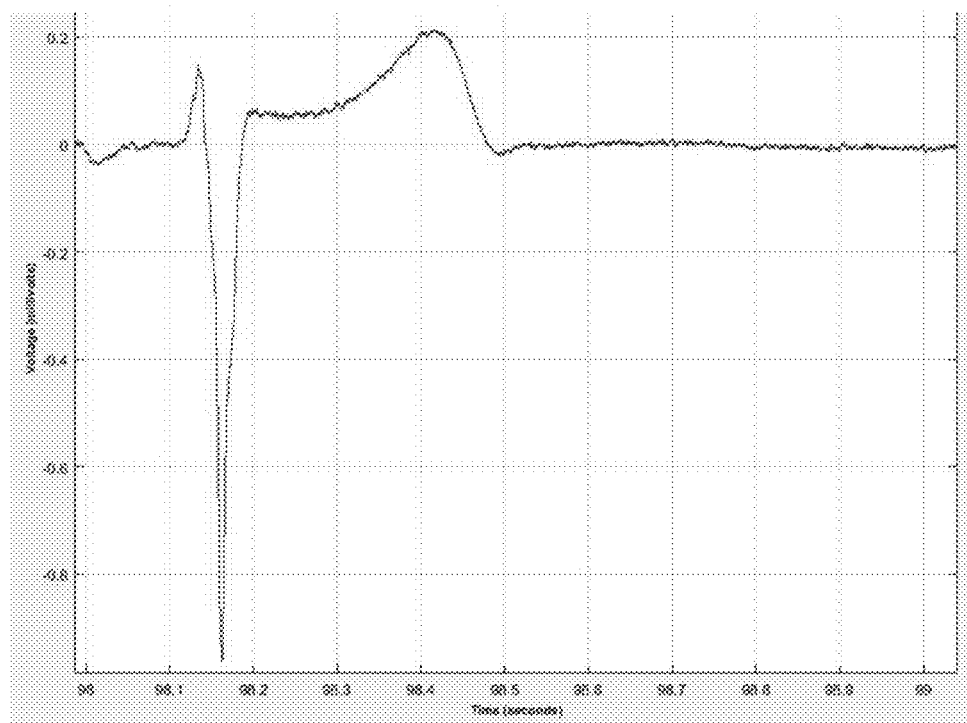
Figure 12D:
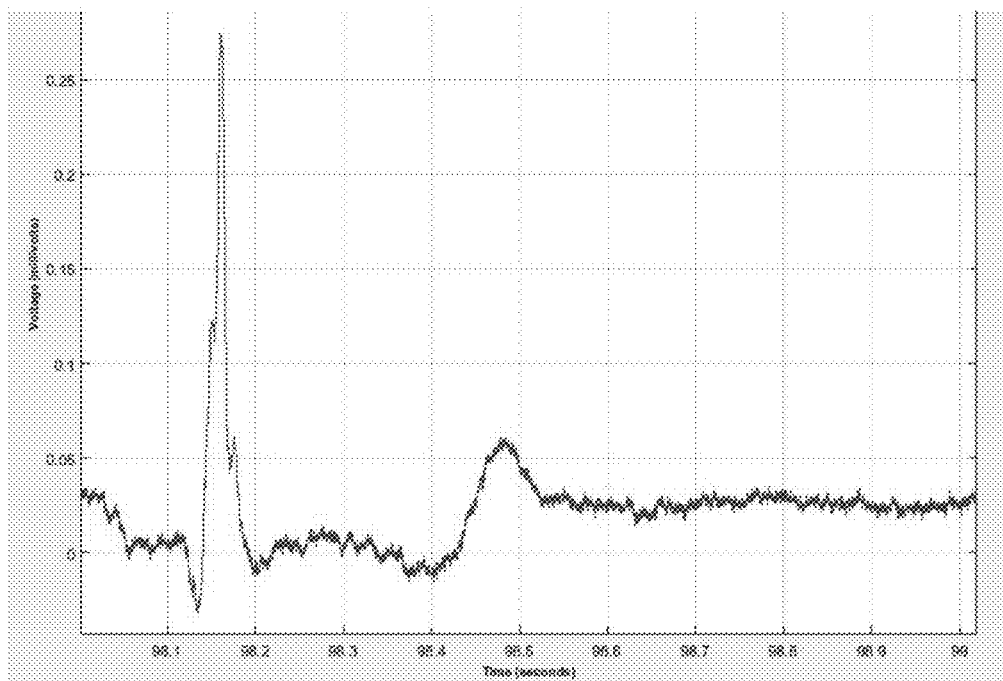
Figure 12E:
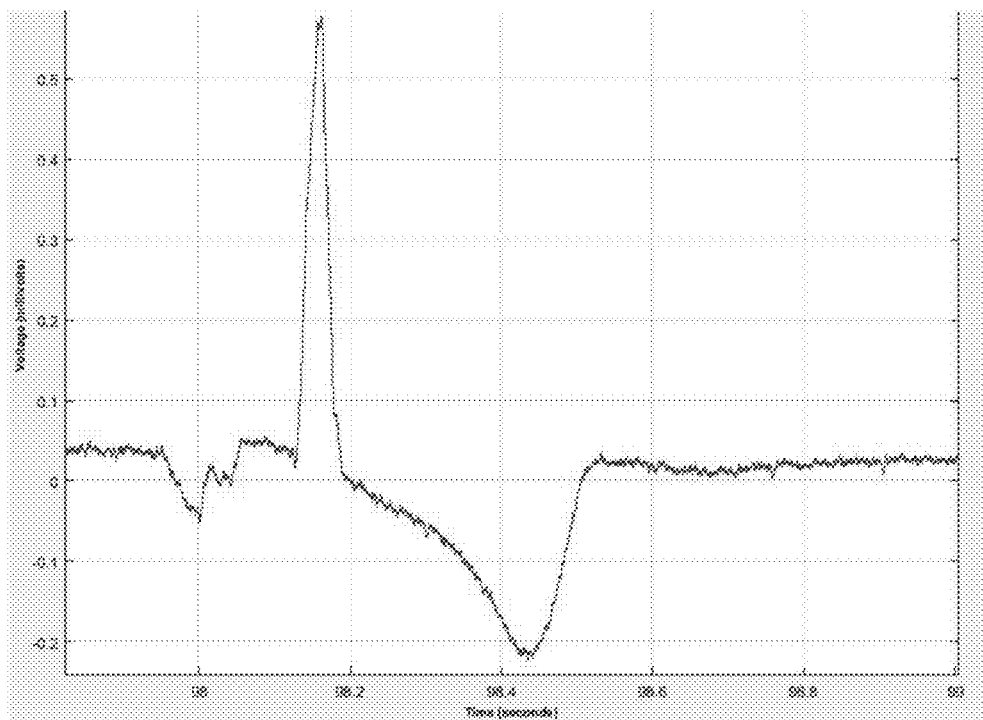
Figure 12F:
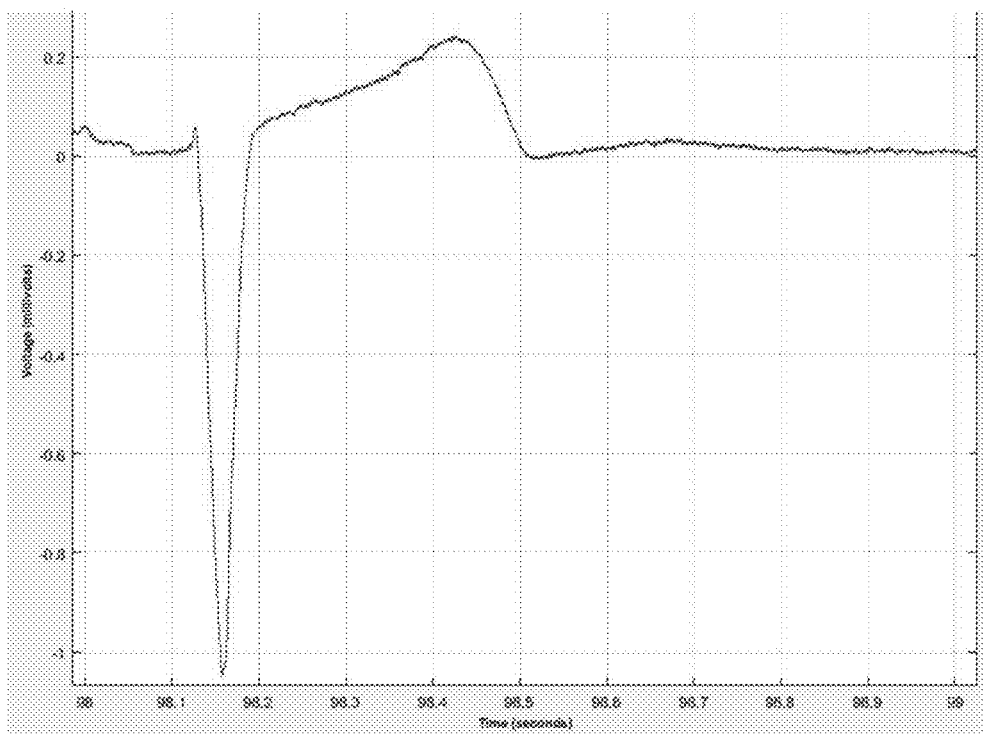

FIG. 11 is a photograph of an example BSA instrument 1100 that includes the BSA board of FIG. 10 in accordance with an embodiment. The BSA system includes a housing 1102 that houses a computing device 1104 (e.g., a portable computing device) that interfaces with the BSA board 1000 (see FIG. 10). The housing 1102 includes the connector 1004 that connects to the cable 124 associated with the surface electrodes (shown as 106a, 106b, 106c, 106d, 106e, 106f, and 106g). As shown in FIG. 11, surface electrodes 106a-106f are used for the acquisition of the wide-band cardiac phase gradient signals and surface electrode 106g is the common-mode reference electrode.

FIG. 12, comprising FIGS. 12A, 12B, 12C, 12D, 12E, and 12F, are example biopotential signal data 116 acquired via the example BSA instrument as shown and described in relation to FIG. 10. The biopotential signal data 116 is shown normalized as time series data and with the common mode potential removed.

Figure 13A:
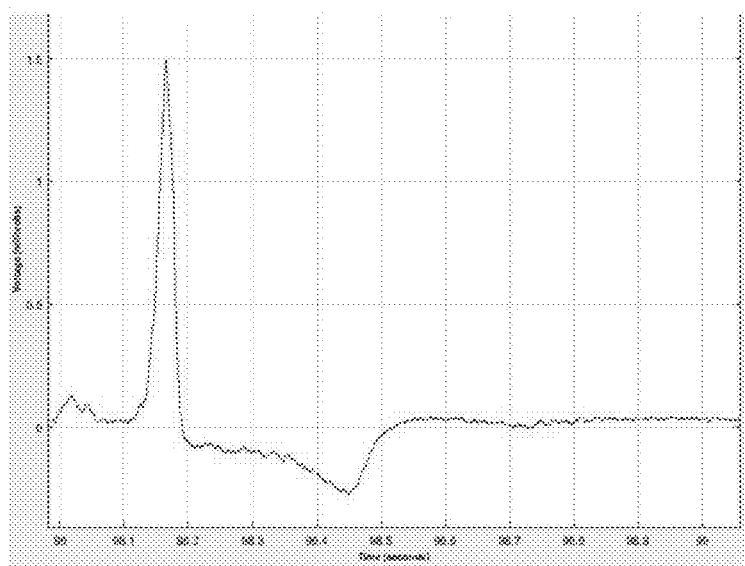
FIGS. 13A, 13B, and 13C, show as an example wide-band cardiac phase gradient signal data generated from the acquired biopotential signal data of FIG. 12.
Figure 13B:
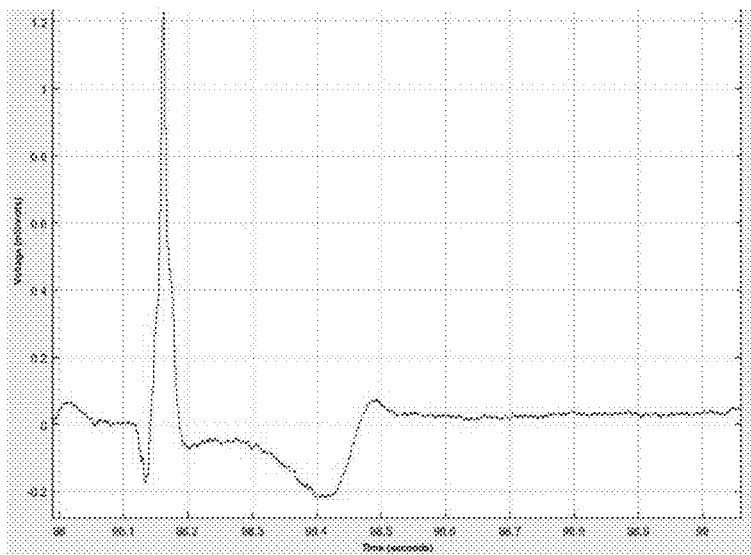
Figure 13C:

FIG. 13, comprising FIGS. 13A, 13B, and 13C, show as an example wide-band cardiac phase gradient signal data generated from the acquired biopotential signal data 116 of FIG. 12. As shown in FIG. 13, the maximum potential of interest is only about a milli-Volt or less with an amplification of 101. The wide-band cardiac phase gradient signal data are generated as differentials of the acquired biopotential signal data. In FIG. 13A, a differential of channel 1 and channel 2 is shown. In FIG. 13B, a differential of channel 3 and 4 is shown. In FIG. 13C, a differential of channel 5 and 6 is shown.

Phase gradient signals are generated from two or more biopotential signals acquired from the body, for example, as a differential between two biopotential signals acquired at two locations on the body. To this end, phase gradient signals can be generated for any given pairing of biopotential signals acquired at various electrodes, in addition to those shown herein, for subsequent analysis in phase space.

Figure 14:
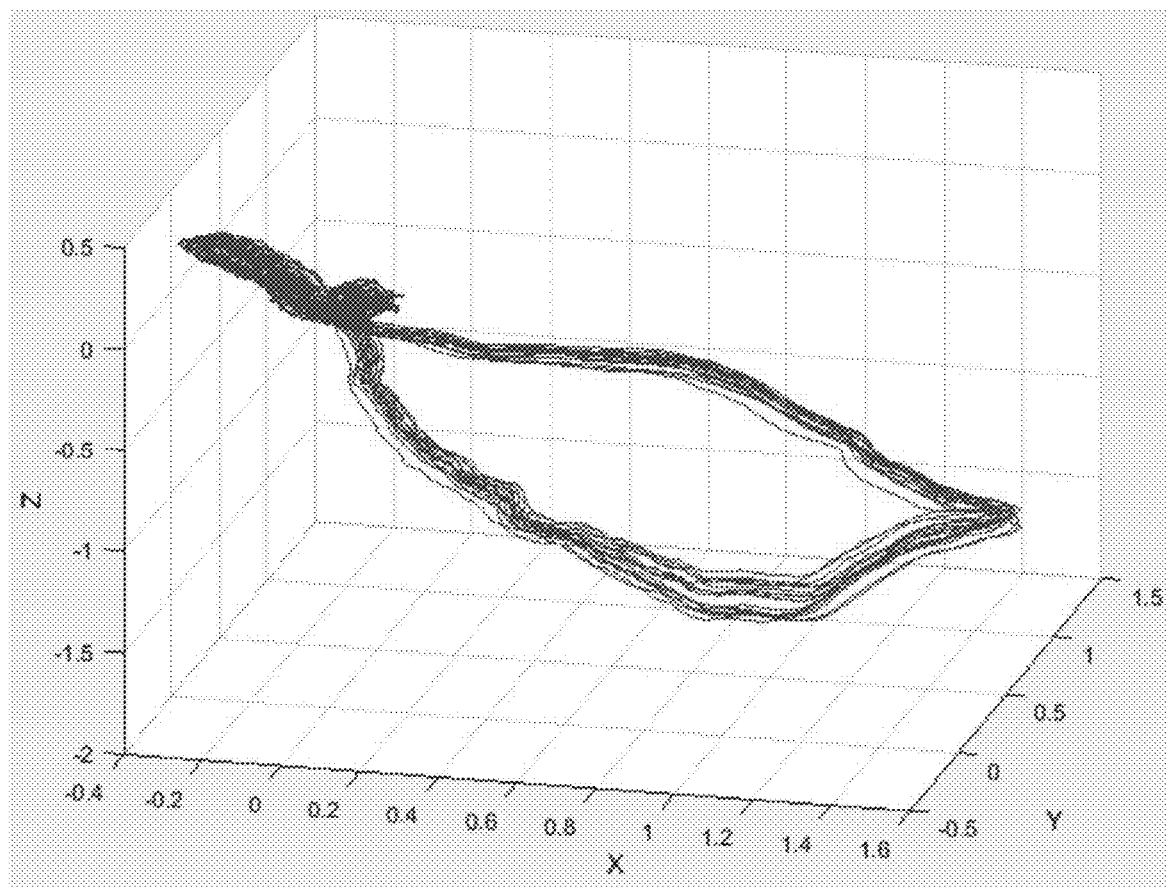
FIG. 14 illustrates an example wide-band cardiac phase gradient signals of FIG. 13 presented in phase space.

FIG. 14 illustrates an example wide-band cardiac phase gradient signal of FIG. 13 presented in phase space. As shown, each of the axes (shown as "X", "Y", and "Z") corresponds to wide-band cardiac phase gradient signal shown in FIGS. 13A, 13B, and 13C.

It should be appreciated that non-linear phase distortions, among other things, as described herein can generate errors in the differential signals, e.g., shown in FIGS. 13A, 13B, and 13C, which shows as non-linear noise in the data in phase space (FIG. 14). To this end, acquisition of wide-band phase gradient signals without non-linear phase distortions can significantly improve the accuracy and precision of subsequent analysis of the wide-band phase gradient signals in phase space.

Examples of the phase space techniques and analyses that can be performed on the wide-band cardiac phase gradient signal are described in above-referenced U.S. Provisional Appl. No. 62/354,668; U.S. application Ser. No. 15/192,639, title "Methods and Systems Using Mathematical Analysis and Machine Learning to Diagnose Disease"; U.S. Publication No. 2015/0216426; U.S. Publication No. 2015/0133803; U.S. Pat. Nos. 8,923,958; 9,289,150, and 9,408,543, each of which is incorporated by reference herein in its entirety.

The wide-band phase gradient signal data generated by the exemplified embodiments may be used, as noted above, as inputs for various phase space techniques and analyses that may in turn be used and performed to generate clinically useful information for assessing the state of the patient's health as well as to, e.g., pinpoint and distinguish disease states and their status as well as for predicting possible disease onset, whether it be in the cardiac or brain fields (such as when wide-band cardiac or cerebral phase gradient signals are used), the oncological field, the prenatal field, or any other medical field in which all or a portion of full spectrum of physiologic signals emitted from the human or other mammalian body could be so used. For example, such clinically useful information may be then further analyzed and transformed into any number of reports, data sets, presentations, etc. (in any number of formats including but not limited to digital formats for presentation via a smartphone or computer, paper report formats, presentation slide formats, or other) for review by a physician and/or presentation to a patient. Such data may be used, for example, by the physician to recommend further testing and/or treatment for the patient. Examples of methods and systems that could be used to collect and process physiologic signals as discussed herein may be found in co-owned and above-referenced U.S. Provisional Patent Application Ser. No. 62/340,410 filed May 23, 2016 and entitled "Method and System for Collecting Phase Signals for Phase Space Tomography Analysis", the entirety of which is incorporated herein by reference. As such, the present embodiments contemplate methods and systems for utilizing the biosignal acquisition instruments described herein to acquire and process any type of mammalian physiological signal into wide-band phase gradient signal data that may be then further processed using various phase space techniques and analyses described herein and for in turn generating data and/or reports based on such techniques and analyses, in any number of formats, that include clinically relevant and useful information for the patient and his/her physician.

Figures 15A, 15B:
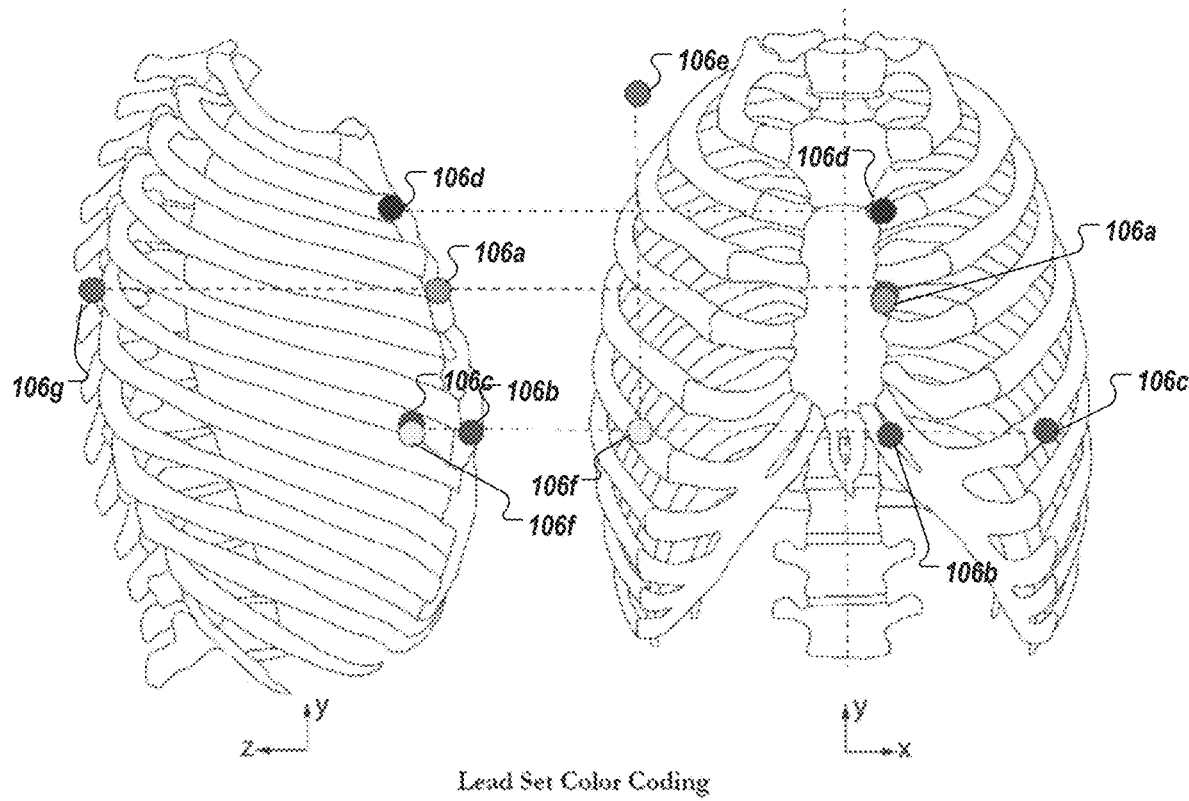
FIGS. 15A and 15B, is a diagram of an example placement of the surface electrodes at the chest and back of a patient to acquire bio-potential signals associated with wide-band cardiac phase gradient signal data of FIG. 13 in accordance with an illustrative embodiment.
Figure 16A:
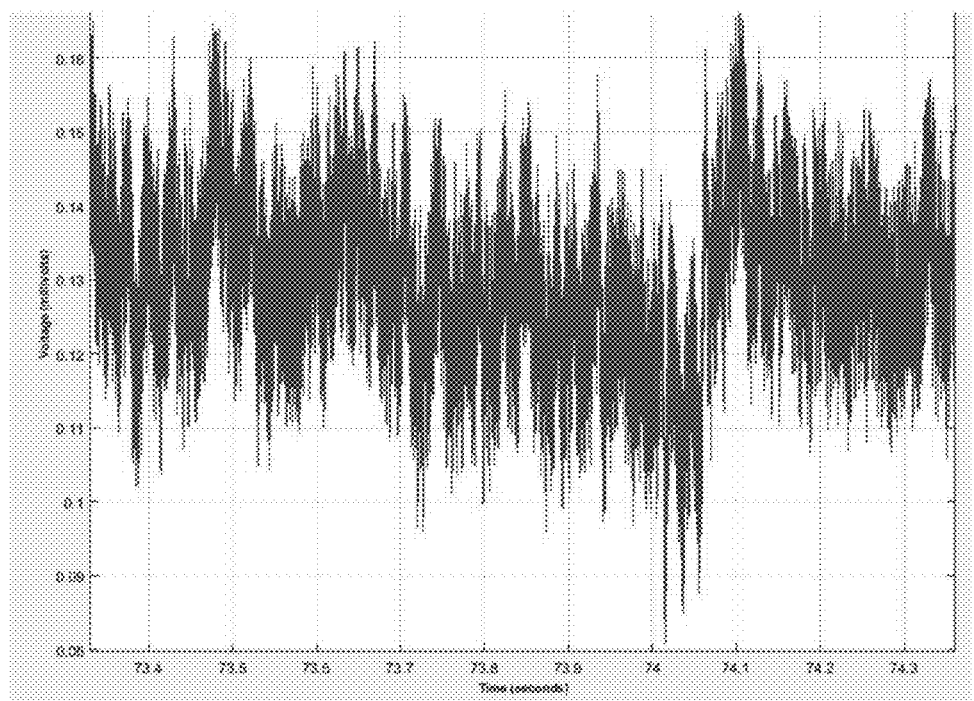
FIGS. 16A, 16B, 16C, 16D, 16E, and 16F, are example biopotential signal data 116 acquired from a head of a patient via the example BSA Instrument as shown and described in relation to FIG. 10.
Figure 16B:
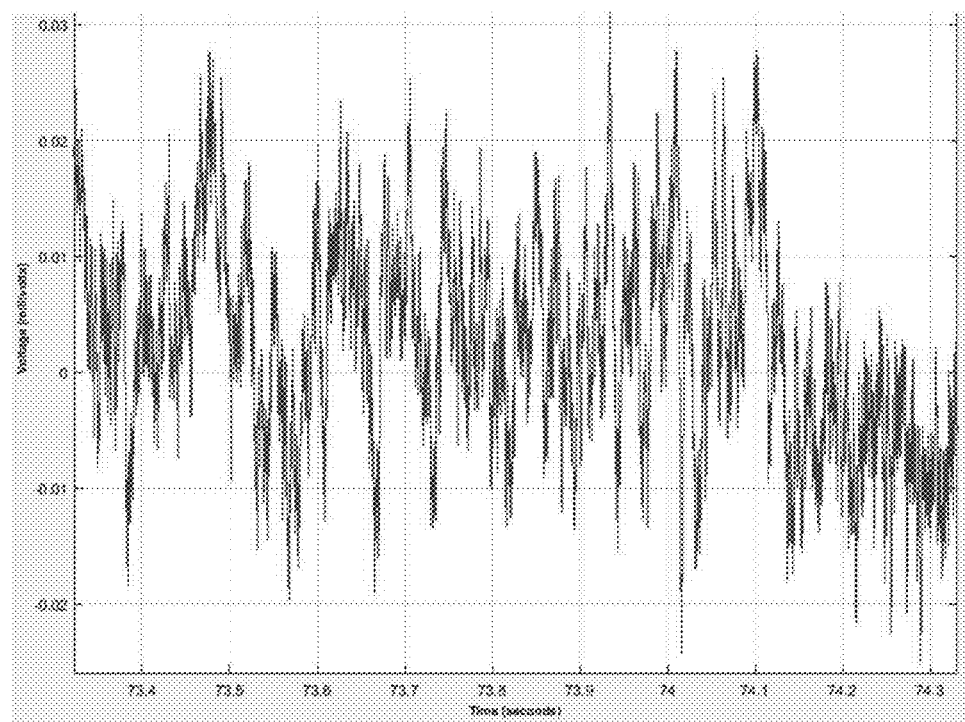
Figure 16C:
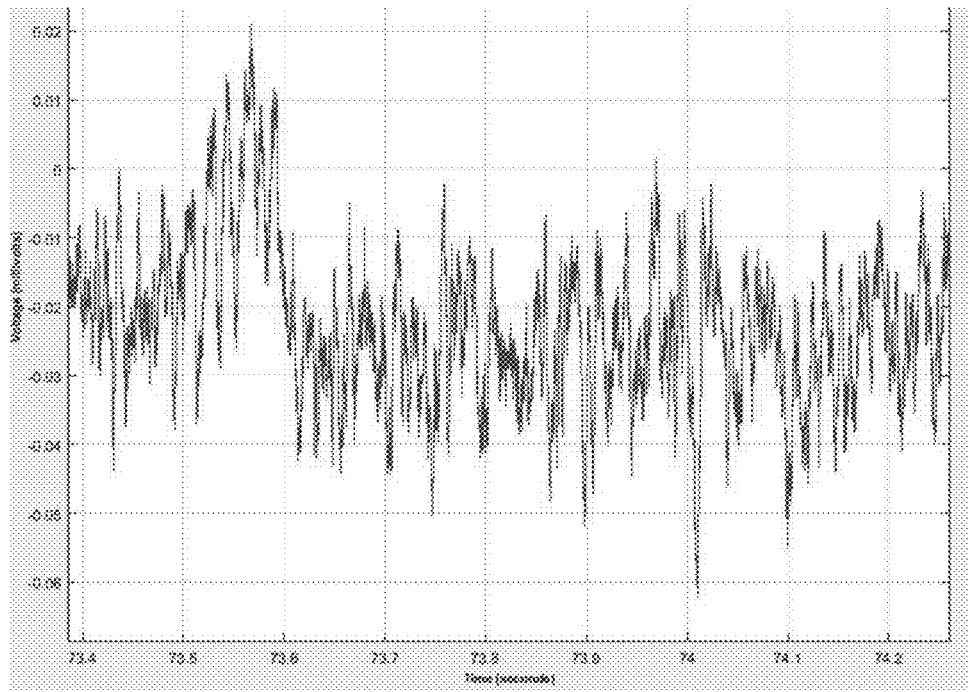
Figure 16D:
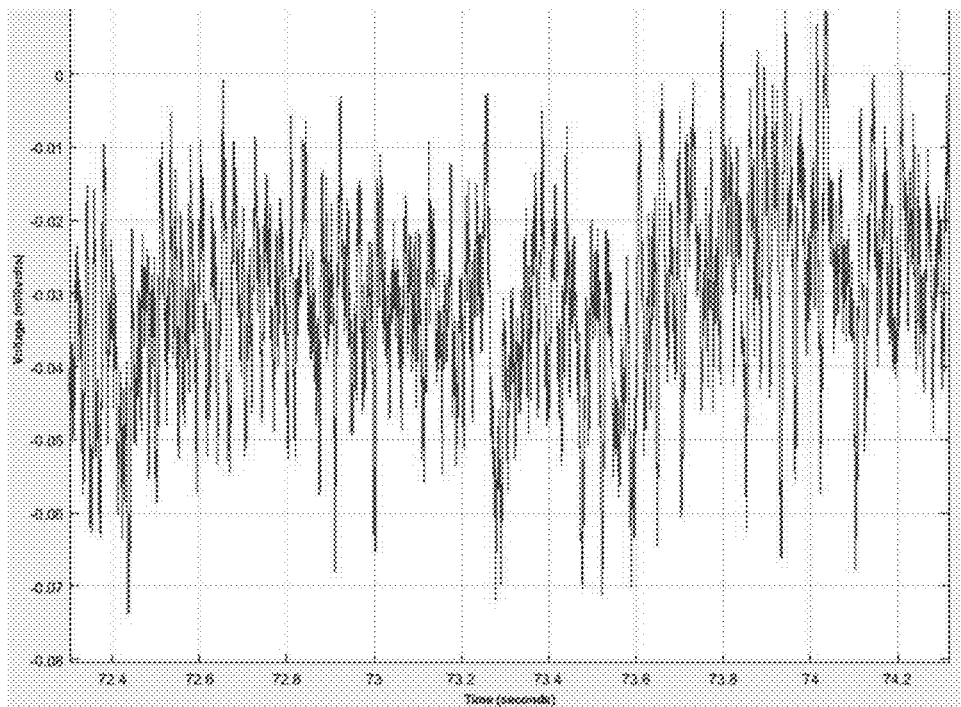
Figure 16E:
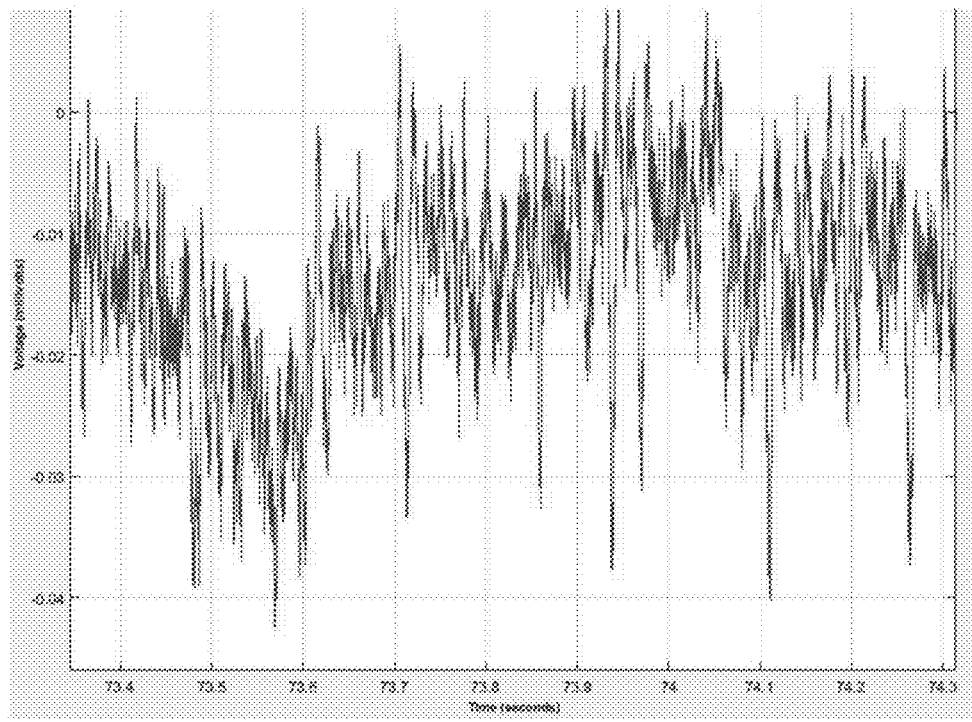
Figure 16F:
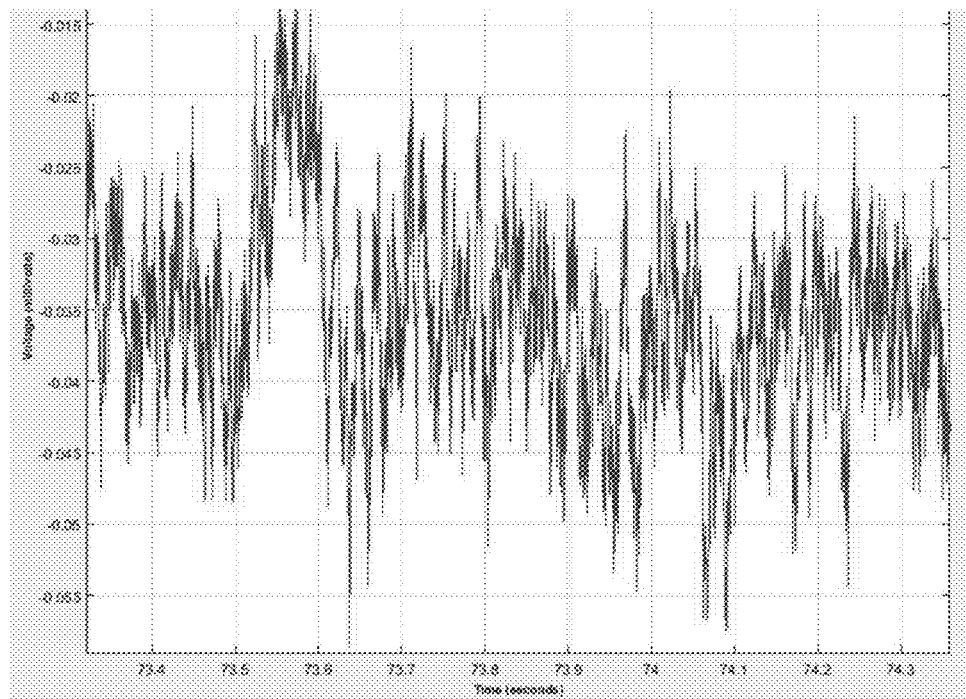

FIG. 15, comprising FIGS. 15A and 15B, is a diagram of an example placement of the surface electrodes 106a-106g at the chest and back of a patient to acquire bio-potential signals associated with wide-band cardiac phase gradient signals in accordance with an illustrative embodiment. FIG. 15A shows a side view of placement of the surface electrodes 106a-106g to the chest and back of the patient. FIG. 15B shows a front view of placement of the surface electrodes 106a-106g to the same. As shown, the surface electrodes are positioned at i) a first location proximal to a Right anterior axillary line corresponding to a 5th intercostal space; ii) a second location proximal to a Left anterior axillary line corresponding to the 5th intercostal space; iii) a third location proximal to a Left sternal border corresponding to a 1st intercostal space; iv) a fourth location proximal to the Left sternal border below the sternum and lateral to a xiphoid process; v) a fifth location proximal to the Left sternal border corresponding to a 3rd intercostal space; vi) a sixth location proximal to a Back directly opposite of the fifth location and left of a spine; and viii) a seventh location proximal to a Right upper quadrant corresponding to a 2nd intercostal space along a Left axillary line.

In addition to acquisition of wide-band cardiac phase gradient signals, the exemplified system 100 may be used to acquire wide-band cerebral phase gradient signals.

FIG. 16, comprising FIGS. 16A, 16B, 16C, 16D, 16E, and 16F, are example biopotential signal data 116 acquired from a head of a patient via the example BSA Instrument as shown and described in relation to FIG. 9. The biopotential signal data 116 is shown normalized as time series data and with the common mode potential removed.

Figure 17A:
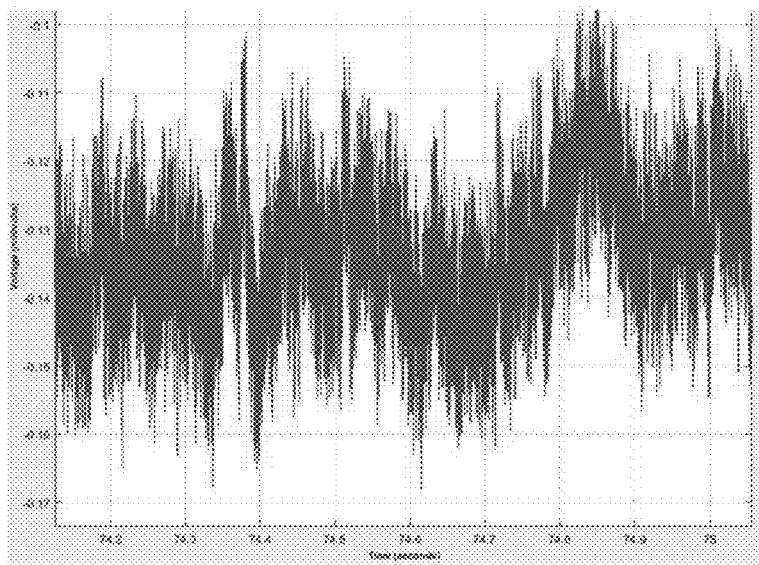
FIGS. 17A, 17B, and 17C, show an example wide-band cerebral phase gradient signal data generated from the acquired biopotential signal data of FIG. 16.
Figure 17B:
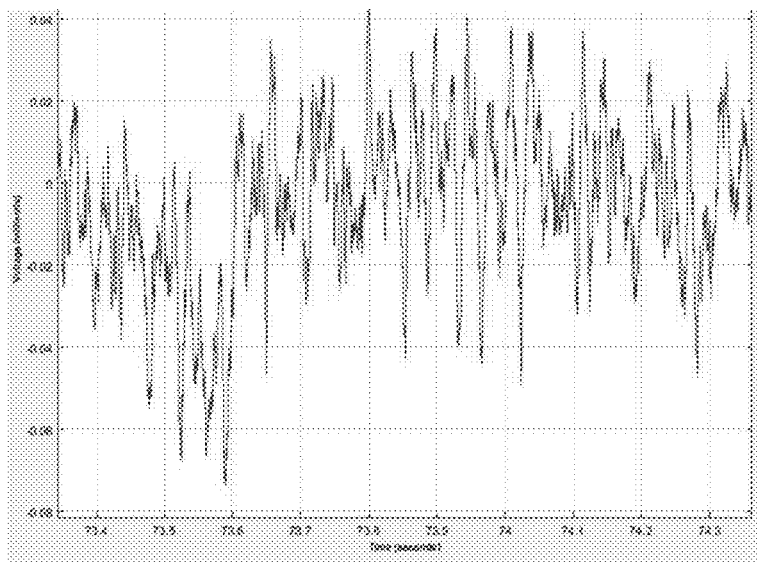
Figure 17C:
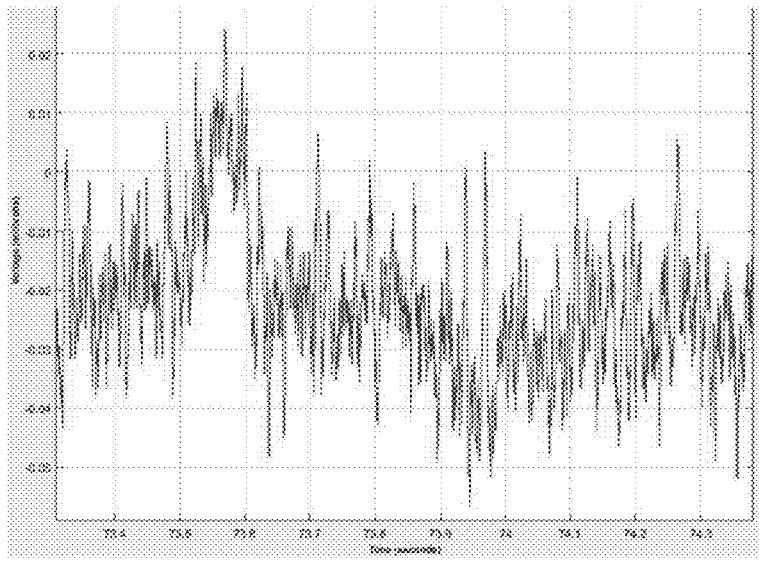

FIG. 17, comprising FIGS. 17A, 17B, and 17C, show an example wide-band cerebral phase gradient signal data generated from the acquired biopotential signal data 116 of FIG. 16. The wide-band cerebral phase gradient signal data are generated as differentials of the acquired biopotential signal data. In FIG. 17A, a differential of channel 1 and channel 2 is shown. In FIG. 17B, a differential of channel 3 and 4 is shown. In FIG. 17C, a differential of channel 5 and 6 is shown.

Figure 18:
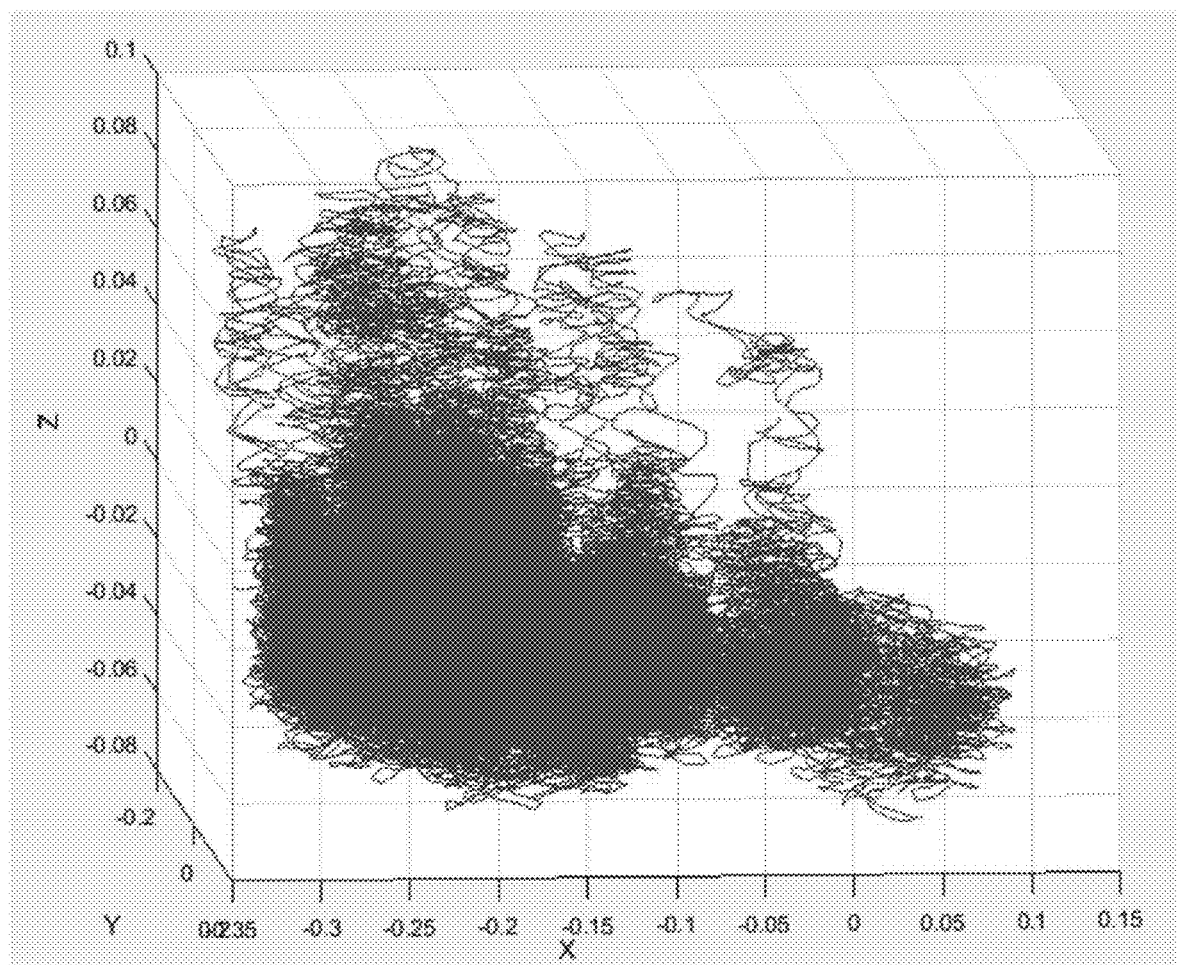
FIG. 18 illustrates an example wide-band cerebral phase gradient signals of FIG. 17 presented in phase space.

FIG. 18 illustrates an example wide-band cerebral phase gradient signal of FIG. 17 presented in phase space. As shown, each of the axes (shown as "X", "Y", and "Z") corresponds to wide-band cerebral phase gradient signal shown in FIGS. 18A, 18B, and 18C.

Figure 19A:
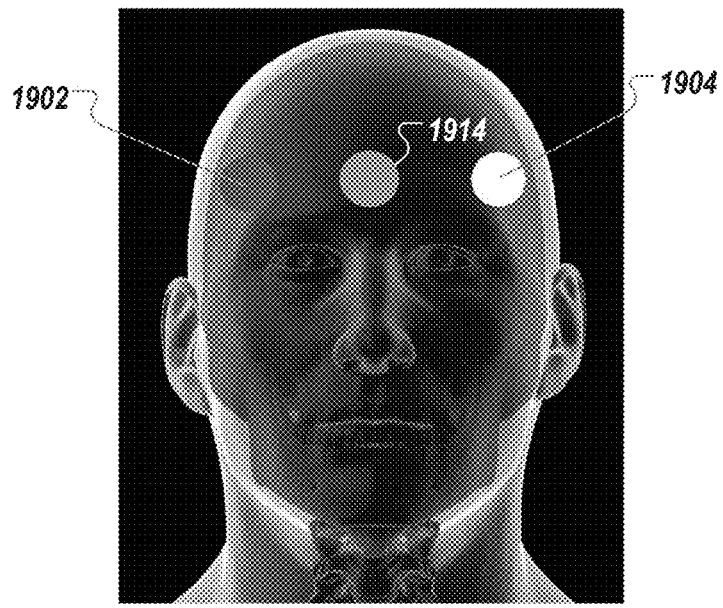
FIGS. 19A, 19B, and 19C, is a diagram of an example placement of the surface electrodes at the head and neck of a patient to acquire biopotential signals associated with wide-band cerebral phase gradient signals in accordance with an illustrative embodiment.
Figure 19B:
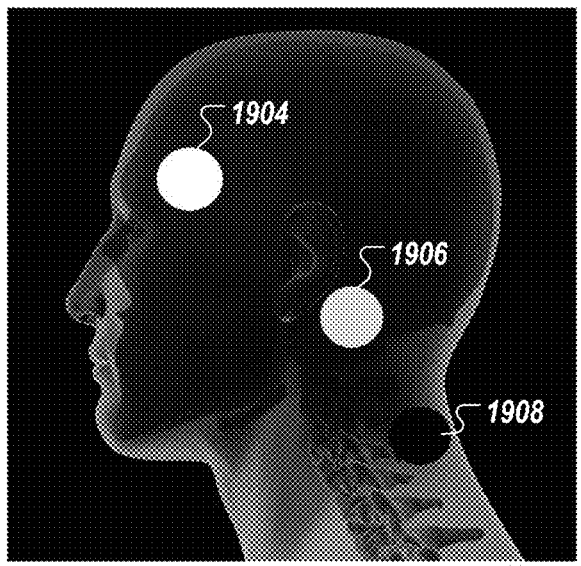
Figure 19C:
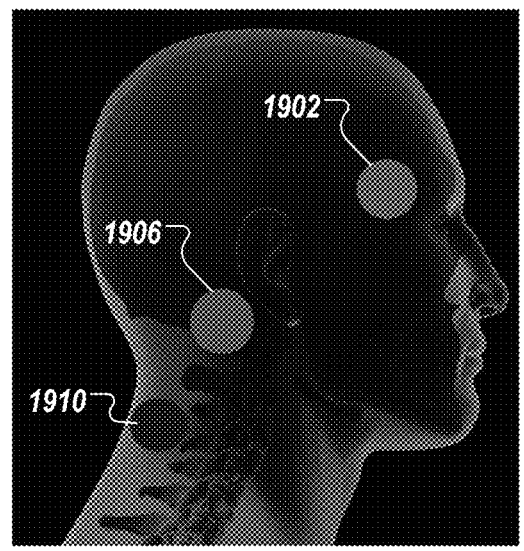

FIG. 19, comprising FIGS. 19A, 19B, and 19C, is a diagram of an example placement of the surface electrodes at the head and neck of a patient to acquire biopotential signals associated with wide-band cerebral phase gradient signals in accordance with an illustrative embodiment. FIG. 19A shows a front view of placement of the surface electrodes 106a-106g to the patient. FIG. 19B and FIG. 19C shows side views of placement of the surface electrodes 106a-106g to the same. As shown, a first set of two surface electrodes (shown as 1902 and 1904) corresponding to a first differential channel is placed at the left and right temple, a second set of two surface electrodes (shown as 1906 and 1908) corresponding to a second differential channel is placed under each ear, and a third set of two surface electrodes (shown as 1910 and 1912) corresponding to a third differential channel is placed at the back of each side of the neck. A seventh surface electrode (shown as 1914) corresponding to common-mode potential output of the system 100 is shown placed at the center.

Figure 20:
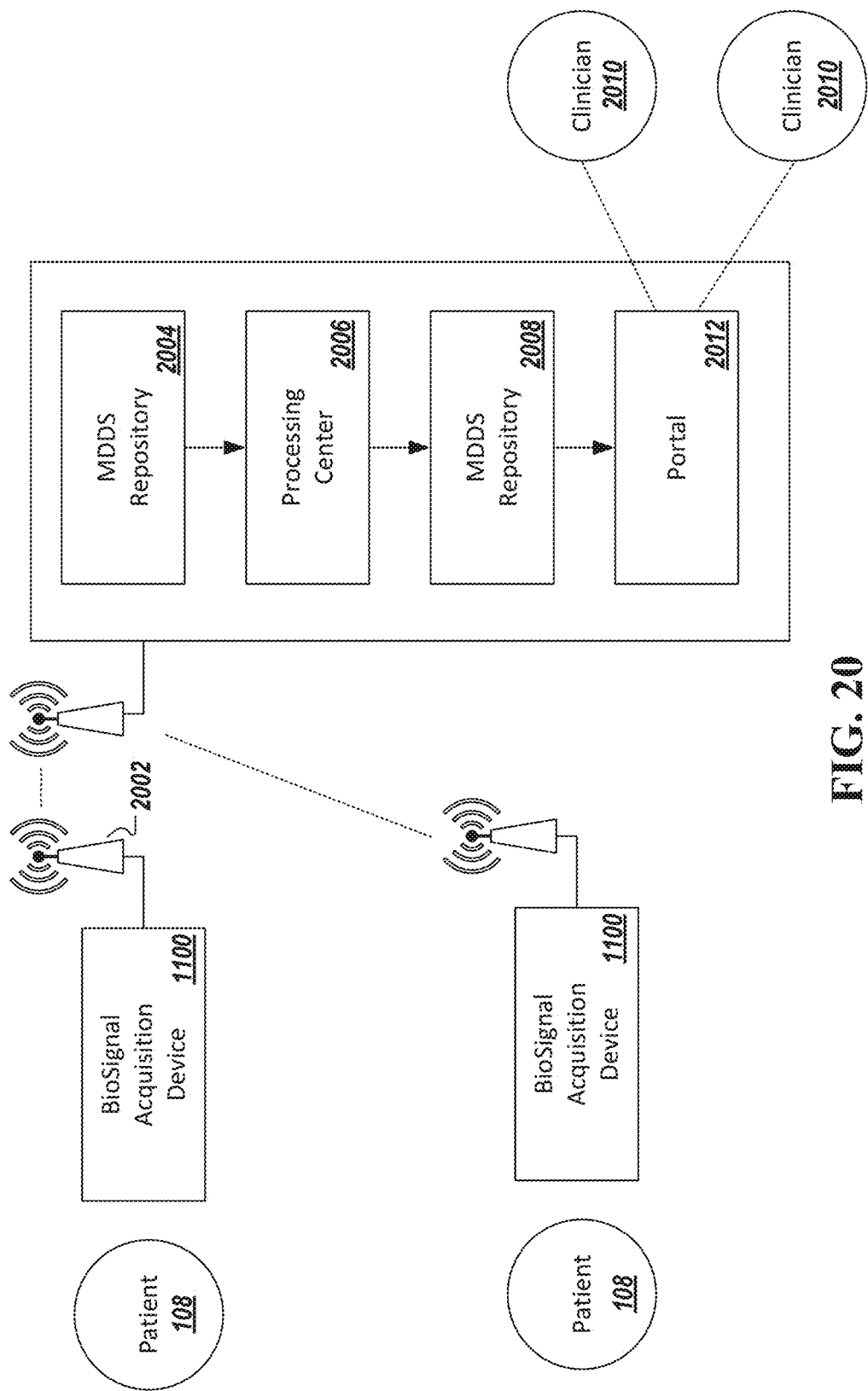
FIG. 20 is an example operation of a BSA instrument in accordance with an illustrative embodiment.

FIG. 20 is an example operation of BSA instrument or device 1100 in accordance with an illustrative embodiment. As shown in FIG. 20, the BSA instrument 1100 is configured to acquire a wide-band cardiac phase gradient signal 116 from a patient 108. Each BSA instrument 1100 is operatively coupled a wireless communication device 2002 that is configured to transmit the acquired wide-band cardiac phase gradient signal data 116 to a data repository 2004 (shown as "MDDS 2004" (Medical Device Data System)) that is connected to a plurality of BSA instrument 100. The wide-band cardiac phase gradient signal data 116 of each BSA instrument 1100 is stored at the repository 2004 and is subsequently analyzed, e.g., by a processing center 2006. The output of the analysis is stored in a diagnosis repository 2008 that is accessible to clinicians, via client devices 2010, from a portal 2012 operatively coupled to the diagnosis repository 2008.

Figure 21:
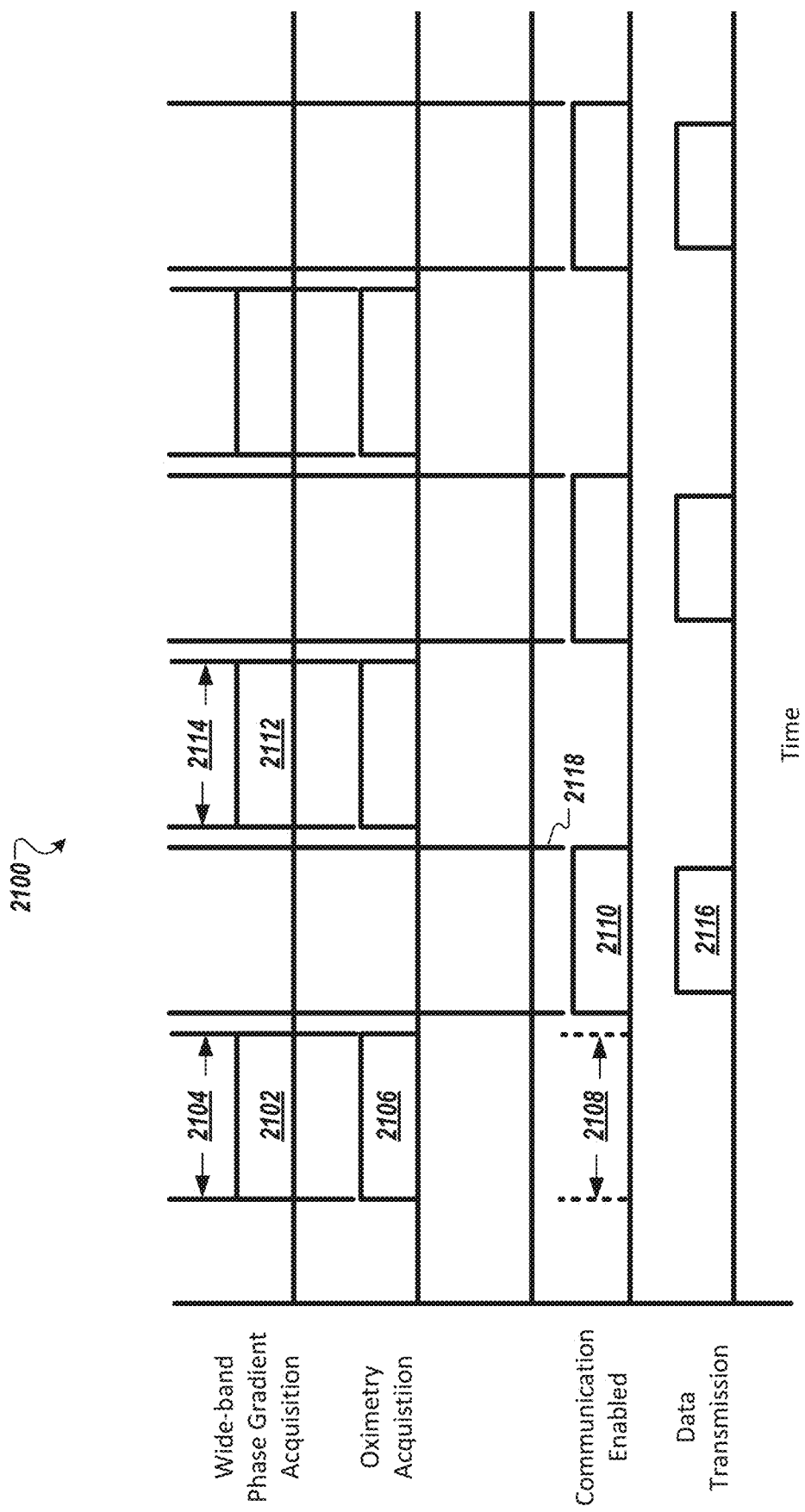
FIG. 21 is a diagram of a method of operating the BSA instrument to reduce interference from self-transmission in accordance with an illustrative embodiment.

FIG. 21 is a diagram of a method 2100 of operating the BSA instrument 1100 to reduce interference from self-transmission in accordance with an illustrative embodiment. Because of the desired high quality acquisition of the signal of interest, namely, the wide-band cardiac phase gradient signal, in some embodiments, the BSA instrument 1100 is configured to coordinate the transmission of the acquired data and the acquisition of the wide-band cardiac phase gradient signal to prevent, or reduce, interference from the wireless communication circuits associated with the BSA instrument 1100. As shown in FIG. 21, acquisition 2102 of biopotential signals associated the wide-band cardiac phase gradient signal is performed at time 2104. In some embodiments, the oximetry measurements 2106 is made concurrently with the same time period. During the acquisition of the wide-band cardiac phase gradient signal, the BSA instrument 1100 is configured to disable the wireless transmitter of the BSA instrument 1100. As shown in FIG. 21, during the time period 2104, the wireless transmitter of the BSA instrument 1100 is disabled (i.e., de-energized) as shown in 2108. After the wide-band cardiac phase gradient signal 2102 has been acquired and stored, the wireless transmitter 2110 of the BSA instrument 1100 is enabled. Prior to the next wide-band cardiac phase gradient signal acquisition 2112 (shown as time period 2114), the previously acquired wide-band cardiac phase gradient signal 2102 is transmitted in data transmission 2116 to a repository. Once transmission 2116 is completed, the wireless transmitter of the BSA instrument 1100 is disabled at time 2118.

Having thus described several embodiments of the present disclosure, it will be rather apparent to those skilled in the art that the foregoing detailed disclosure is intended to be presented by way of example only, and is not limiting. Many advantages for non-invasive method and system for location of an abnormality in a heart have been discussed herein. Various alterations, improvements, and modifications will occur and are intended to those skilled in the art, though not expressly stated herein. These alterations, improvements, and modifications are intended to be suggested hereby, and are within the spirit and the scope of the present disclosure.

In some embodiments, acquisition of biopotential signals associated with wide-band phase gradient signals may be performed at other parts of the body to diagnose various disease and conditions. For example, the exemplified system may be used to acquire biopotential signals associated with wide-band phase gradient signals for oncology. The exemplified system may be used to acquire biopotential signals associated with wide-band phase gradient signals for monitoring pre-natal development.

It is contemplated that the exemplified methods and systems can be used to acquire biosignals from any type of mammals and animals including test animals for research and clinical purposes as well as for the treatment of animals in veterinary purposes.

Additionally, the recited order of the processing elements or sequences, or the use of numbers, letters, or other designations therefore, is not intended to limit the claimed processes to any order except as may be specified in the claims. Accordingly, the present disclosure is limited only by the following claims and equivalents thereto.

What is claimed is:

1. An apparatus comprising:
    a plurality of biosignal acquisition channels configured to acquire biopotential signals of a biopotential signal data set and to convert the acquired biopotential signals without filtering;
    an oxygen saturation acquisition circuit configured to acquire a waveform of a photodiode signal;
    a gain amplifier configured to amplify the photodiode signal received from an associated photodiode configured to be placed on a mammal; and
    an analog-to-digital conversion circuit configured to receive an output of the gain amplifier and sample the amplified photodiode signal to generate an oxygen saturation reading data set,
    wherein the generated oxygen saturation reading data set is analyzed along with the biopotential signal data set acquired concurrently with the oxygen saturation reading data set, to generate an output data set in a report and/or a display, and wherein the output data set is used in a diagnosis of cardiac disease.

2. The apparatus of claim 1, wherein the photodiode signal is a light emitting diode (LED) output and/or an infrared diode output.

3. The apparatus of claim 1, wherein the plurality of biosignal acquisition channels include a first biosignal acquisition channel and a second biosignal acquisition channel.

4. The apparatus of claim 3, wherein the first biosignal acquisition channel comprises:
    a surface electrode configured to be placed on and in proximity to a heart of the mammal;
    a gain amplifier configured to amplify a biopotential signal received from the surface electrode; and
    an analog-to-digital conversion circuit that receives an output of the gain amplifier of the first biosignal acquisition channel and that simultaneously samples the amplified biopotential signal with respect to other biosignal acquisition channels of the plurality of biosignal acquisition channels.

5. The apparatus of claim 4, wherein the plurality of biosignal acquisition channels are further configured to amplify and convert the acquired biopotential signals without the filtering that can cause phase distortion in the respective received biopotential signal above 1 kHz.

6. The apparatus of claim 1, further comprising:
    a housing, the plurality of biosignal acquisition channels and oxygen saturation acquisition circuit being located in the housing.

7. The apparatus of claim 1, wherein the photodiode signal is received from an associated photodiode configured to be placed on a finger of the mammal.

8. The apparatus of claim 1, wherein each of the plurality of biosignal acquisition channels comprises:
    a gain amplifier configured to amplify the received biopotential signal with a gain that provides a measurement resolution, with the analog-to-digital conversion circuit, greater than 0.3 µV per bit.

9. The apparatus of claim 1, comprising:
    a single positive voltage supply, wherein the gain amplifier is powered by the single positive voltage supply.

10. The apparatus of claim 1, wherein the plurality of biosignal acquisition channels comprises a number of channels selected from the group consisting of 2, 3, 4, 5, 6, 7, 8, 9, 10, 11, and 12.

11. The apparatus of claim 1, wherein the analog-to-digital conversion circuit of each of the plurality of biosignal acquisition channels is configured to sample a wide-band cardiac phase gradient signal over a pre-defined voltage range of at least 5 mV at a resolution of less than 2 µV per bit and at a rate greater than 5 kHz, wherein the plurality of biosignal acquisition channels are simultaneously sampled, and wherein each biosignal acquisition channel comprises a signal-to-noise ratio of greater than 15 dB.

12. The apparatus of claim 1, further comprising:
    a defibrillation protection circuit comprising a switching element that does not add thermal noise or avalanche noise to a signal path of a drive circuit, wherein the drive circuit is coupled, at an output thereof, to the defibrillation protection circuit.

13. The apparatus of claim 1, wherein the oxygen saturation reading data set and biopotential signal data set are further analyzed via machine learning algorithms to assess regional flow characteristics of the mammal's heart.

14. The apparatus of claim 1, wherein the oxygen saturation reading data set and biopotential signal data set are analyzed, in phase-associated analysis, to generate the output data set comprising one or more assessments selected from the group consisting of ejection fraction estimation, ischemic burden estimation, and a detection of coronary artery disease.

15. The apparatus of claim 1, further comprising:
    a wireless communication subsystem, wherein the wireless communication subsystem comprises an antenna and a transceiver, wherein the transceiver is configured to transmit, via the antenna, the oxygen saturation reading data set to a remote computing and/or storage device.

16. The apparatus of claim 1, wherein the generated oxygen saturation reading data set and biopotential signal data set are analyzed in phase-associated analysis performed in a phase space domain.

17. The apparatus of claim 1, wherein the oxygen saturation acquisition circuit shares a same power source with the plurality of biosignal acquisition channels.

18. The apparatus of claim 1, wherein the mammal is a human subject.

19. The apparatus of claim 1, wherein the analog-to-digital conversion circuit of each of the plurality of biosignal acquisition channels is configured to sample a wide-band cardiac phase gradient signal over a pre-defined voltage range of at least 5 mV at a resolution of less than 2 μV per bit and at a rate greater than 5 kHz.

20. The apparatus of claim 1, wherein the plurality of biosignal acquisition channels are simultaneously sampled, and wherein each biosignal acquisition channel comprises a signal-to-noise ratio of greater than 15 dB.

21. A method comprising:
  acquiring, by a biosignal acquisition instrument comprising a plurality of biosignal acquisition channels, biopotential signals of a biopotential signal data set and converting the acquired biopotential signals without filtering;
  acquiring, by an oxygen saturation circuit of a measurement system operatively coupled to biosignal acquisition instrument, a waveform of a photodiode signal;
  amplifying, by a gain amplifier of the measurement system, the photodiode signal received from an associated photodiode;
  generating, by an analog-to-digital conversion circuit of the measurement system configured to receive an output of the gain amplifier and sample the amplified photodiode signal, a mammalian oxygen saturation reading data set representing oxygen saturation acquired from the photodiode having been placed on, or in proximity to a mammalian patient; and
  transmitting, by the measurement system, the acquired oxygen saturation reading data set to a storage area network,
  wherein the stored oxygen saturation reading data set is analyzed along with the biopotential signal data set that had been acquired concurrently with the oxygen saturation reading data set, to generate an output data set in a report and/or a display, and wherein the output data set is used in a diagnosis of cardiac disease.

22. The method of claim 21, further comprising:
  retrieving, by an analysis system, the mammalian biopotential signal data set and the mammalian oxygen saturation reading data set from the storage area network, wherein the biopotential signal data set had been acquired concurrently with the oxygen saturation reading data set and the biopotential signal data set was acquired and converted without filtering;
  analyzing, by the analysis system, the retrieved oxygen saturation reading data set and biopotential signal data set to generate the output data set in the report and/or the display.

* * * * *